(12) United States Patent
Toida et al.

(10) Patent No.: US 11,480,877 B2
(45) Date of Patent: *Oct. 25, 2022

(54) RESIST COMPOSITION, METHOD FOR FORMING RESIST PATTERN, AND POLYPHENOL COMPOUND USED THEREIN

(71) Applicant: Mitsubishi Gas Chemical Company, Inc., Tokyo (JP)

(72) Inventors: Takumi Toida, Kanagawa (JP); Masatoshi Echigo, Tokyo (JP); Takashi Sato, Kanagawa (JP); Youko Shimizu, Kanagawa (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/560,458

(22) PCT Filed: Mar. 2, 2016

(86) PCT No.: PCT/JP2016/056333
§ 371 (c)(1),
(2) Date: Sep. 21, 2017

(87) PCT Pub. No.: WO2016/158169
PCT Pub. Date: Oct. 6, 2016

(65) Prior Publication Data
US 2018/0074402 A1 Mar. 15, 2018

(30) Foreign Application Priority Data
Mar. 31, 2015 (JP) .............................. JP2015-073265

(51) Int. Cl.
| | | |
|---|---|---|
| *G03F 7/004* | (2006.01) |
| *G03F 7/038* | (2006.01) |
| *G03F 7/30* | (2006.01) |
| *C07C 39/17* | (2006.01) |
| *C07D 493/04* | (2006.01) |
| *C08G 8/14* | (2006.01) |
| *C08G 10/02* | (2006.01) |
| *C07B 61/00* | (2006.01) |
| *C07D 311/92* | (2006.01) |
| *C08G 61/12* | (2006.01) |
| *C07C 37/20* | (2006.01) |
| *C07C 39/14* | (2006.01) |
| *C07C 39/225* | (2006.01) |
| *C07C 39/42* | (2006.01) |
| *C07D 311/78* | (2006.01) |
| *C07D 311/96* | (2006.01) |
| *G03F 7/20* | (2006.01) |
| *G03F 7/32* | (2006.01) |

(52) U.S. Cl.
CPC ............ *G03F 7/0382* (2013.01); *C07B 61/00* (2013.01); *C07C 37/20* (2013.01); *C07C 39/14* (2013.01); *C07C 39/17* (2013.01); *C07C 39/225* (2013.01); *C07C 39/42* (2013.01); *C07D 311/78* (2013.01); *C07D 311/92* (2013.01); *C07D 311/96* (2013.01); *C08G 8/14* (2013.01); *C08G 10/02* (2013.01); *C08G 61/12* (2013.01); *G03F 7/004* (2013.01); *G03F 7/0045* (2013.01); *G03F 7/038* (2013.01); *G03F 7/2039* (2013.01); *G03F 7/327* (2013.01)

(58) Field of Classification Search
CPC ........ G03F 7/0045; G03F 7/0382; G03F 7/30; C07C 39/17; C07D 493/04; C08G 8/14; C08G 10/02; C08G 2261/71
USPC ........ 430/270.1, 325, 905; 549/382; 568/719
See application file for complete search history.

(56) References Cited

U.S. PATENT DOCUMENTS

| | | |
|---|---|---|
| 2,100,798 A | 11/1937 | Dilthey |
| 2,546,872 A | 3/1951 | Schmid |
| 2,587,437 A | 2/1952 | Bralley |
| 3,947,468 A | 3/1976 | Hall |

(Continued)

FOREIGN PATENT DOCUMENTS

| | | |
|---|---|---|
| CN | 1414031 | 4/2003 |
| CN | 1853141 A | 10/2006 |

(Continued)

OTHER PUBLICATIONS

International Search Report on Patentability for PCT/JP2016/056333 dated May 24, 2016; English translation submitted herewith (7 pages).

(Continued)

*Primary Examiner* — John S Chu
(74) *Attorney, Agent, or Firm* — Fitch, Even, Tabin & Flannery LLP

(57) ABSTRACT

The present invention is a compound represented by the following general formula (1).

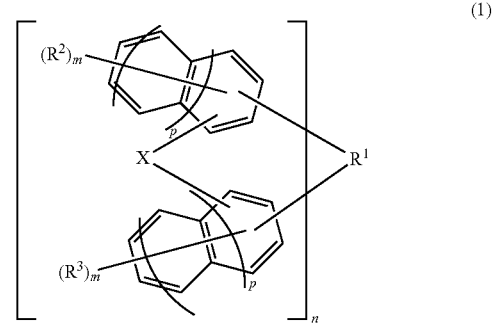

(1)

21 Claims, No Drawings

(56) References Cited

U.S. PATENT DOCUMENTS

| | | | |
|---|---|---|---|
| 4,252,884 A | 2/1981 | Bennett | |
| 4,289,839 A | 9/1981 | Dipippo | |
| 4,482,489 A | 11/1984 | Dipippo | |
| 4,579,758 A | 4/1986 | Dorsch | |
| 5,332,648 A | 7/1994 | Kihara | |
| 5,986,094 A | 11/1999 | Ghoshal | |
| 6,784,228 B2 | 8/2004 | Ogura | |
| 6,794,408 B2 | 9/2004 | Eder | |
| 7,871,751 B2 | 1/2011 | Echigo | |
| 9,122,153 B2* | 9/2015 | Echigo | C07C 39/17 |
| 9,136,121 B2 | 9/2015 | Hatakeyama | |
| 9,274,426 B2 | 3/2016 | Rahman | |
| 9,316,913 B2 | 4/2016 | Echigo | |
| 9,540,339 B2* | 1/2017 | Echigo | C07D 311/96 |
| 9,908,831 B2* | 3/2018 | Echigo | C07D 311/96 |
| 10,303,055 B2 | 5/2019 | Sato | |
| 10,377,734 B2 | 8/2019 | Echigo | |
| 2002/0106909 A1 | 8/2002 | Kato | |
| 2003/0092852 A1 | 5/2003 | Ogura | |
| 2004/0197709 A1 | 10/2004 | Arase | |
| 2005/0074695 A1 | 4/2005 | Nakamura | |
| 2005/0255712 A1 | 11/2005 | Kato | |
| 2007/0059632 A1* | 3/2007 | Oguro | C07D 311/82 430/270.1 |
| 2007/0172759 A1 | 7/2007 | Ogihara | |
| 2007/0232839 A1 | 10/2007 | Yoshitomo et al. | |
| 2007/0275325 A1 | 11/2007 | Hatakeyama | |
| 2008/0113294 A1 | 5/2008 | Echigo | |
| 2008/0138744 A1 | 6/2008 | Hatanaka | |
| 2008/0153031 A1 | 6/2008 | Echigo et al. | |
| 2009/0171061 A1 | 7/2009 | Sue | |
| 2009/0246684 A1 | 10/2009 | Kim | |
| 2009/0261300 A1 | 10/2009 | Watanabe | |
| 2010/0047709 A1* | 2/2010 | Echigo | C07C 37/20 430/270.1 |
| 2010/0099044 A1 | 4/2010 | Hatakeyama | |
| 2010/0104977 A1 | 4/2010 | Hatakeyama | |
| 2010/0136477 A1 | 6/2010 | Ng | |
| 2010/0190107 A1 | 7/2010 | Shibata | |
| 2010/0207516 A1 | 8/2010 | Moriwaki | |
| 2010/0227859 A1 | 9/2010 | Li | |
| 2010/0285407 A1 | 11/2010 | Ogihara | |
| 2010/0316950 A1 | 12/2010 | Oguro | |
| 2011/0177459 A1 | 7/2011 | Ogihara | |
| 2011/0230058 A1 | 9/2011 | Sakamoto et al. | |
| 2011/0274713 A1 | 11/2011 | Burn | |
| 2011/0311920 A1 | 12/2011 | Kinsho | |
| 2012/0064725 A1 | 3/2012 | Kinsho | |
| 2012/0171611 A1 | 7/2012 | Ideno | |
| 2012/0184103 A1 | 7/2012 | Ogihara | |
| 2012/0220112 A1* | 8/2012 | Hatakeyama | G03F 7/0392 438/514 |
| 2012/0228584 A1 | 9/2012 | Wigglesworth | |
| 2013/0004896 A1 | 1/2013 | Echigo et al. | |
| 2013/0056653 A1 | 3/2013 | Hatakeyama | |
| 2013/0056654 A1 | 3/2013 | Hatakeyama et al. | |
| 2013/0084705 A1 | 4/2013 | Nakafuji et al. | |
| 2013/0087529 A1 | 4/2013 | Hatakeyama | |
| 2013/0150627 A1 | 6/2013 | Okada | |
| 2014/0186776 A1 | 7/2014 | Uchiyama | |
| 2014/0248556 A1 | 9/2014 | Kato | |
| 2014/0248561 A1* | 9/2014 | Echigo | C07D 311/96 430/281.1 |
| 2014/0308615 A1* | 10/2014 | Echigo | C07C 39/17 430/281.1 |
| 2014/0319097 A1 | 10/2014 | Kim | |
| 2014/0363768 A1 | 12/2014 | Kinsho et al. | |
| 2014/0363955 A1 | 12/2014 | Hatakeyama et al. | |
| 2014/0363957 A1 | 12/2014 | Hatakeyama | |
| 2014/0363958 A1 | 12/2014 | Hatakeyama | |
| 2015/0030980 A1 | 1/2015 | Echigo et al. | |
| 2015/0037735 A1 | 2/2015 | Yang | |
| 2015/0090691 A1* | 4/2015 | Echigo | C07D 311/96 216/49 |
| 2015/0309403 A1 | 10/2015 | Rahman | |
| 2015/0368224 A1* | 12/2015 | Echigo | C07C 41/01 549/382 |
| 2015/0376157 A1 | 12/2015 | Echigo | |
| 2015/0376158 A1 | 12/2015 | Echigo | |
| 2015/0376202 A1 | 12/2015 | Echigo | |
| 2016/0130243 A1 | 5/2016 | Satou | |
| 2016/0145231 A1 | 5/2016 | Echigo | |
| 2017/0183279 A1* | 6/2017 | Echigo | C07D 311/96 |
| 2017/0349564 A1* | 12/2017 | Toida | C07D 311/78 |
| 2018/0074406 A1 | 3/2018 | Toida et al. | |
| 2018/0208703 A1 | 7/2018 | Okada et al. | |

FOREIGN PATENT DOCUMENTS

| | | |
|---|---|---|
| CN | 101889247 A | 11/2010 |
| CN | 102070595 | 5/2011 |
| CN | 103304385 A | 9/2013 |
| CN | 103733136 A | 4/2014 |
| CN | 103804196 A | 5/2014 |
| CN | 104557552 A | 4/2015 |
| EP | 1275673 | 1/2003 |
| EP | 1300403 | 4/2003 |
| EP | 1666970 | 6/2006 |
| EP | 2743249 | 6/2014 |
| EP | 2743769 | 6/2014 |
| EP | 2743770 A1 | 6/2014 |
| EP | 3279190 A1 | 2/2018 |
| JP | S48049508 A | 7/1973 |
| JP | 62094841 A | 5/1987 |
| JP | S62191850 A | 8/1987 |
| JP | H01283280 | 11/1989 |
| JP | H04217675 | 8/1992 |
| JP | H05-19463 A | 1/1993 |
| JP | H05034913 A | 2/1993 |
| JP | H05134415 A | 5/1993 |
| JP | H05163290 A | 6/1993 |
| JP | 05216235 | 8/1993 |
| JP | H06049402 A | 2/1994 |
| JP | H06242607 A | 9/1994 |
| JP | H07215833 | 8/1995 |
| JP | H1025220 | 1/1998 |
| JP | H10045764 A | 2/1998 |
| JP | H11072925 | 3/1999 |
| JP | 2001042525 | 2/2001 |
| JP | 2002214769 | 7/2002 |
| JP | 2002334869 A | 11/2002 |
| JP | 2002334896 | 11/2002 |
| JP | 2002341542 | 11/2002 |
| JP | 2003-201333 A | 7/2003 |
| JP | 2004177668 A | 6/2004 |
| JP | 2004271838 A | 9/2004 |
| JP | 2005250434 A | 9/2005 |
| JP | 2005266741 A | 9/2005 |
| JP | 2005-326838 A | 11/2005 |
| JP | 2005326868 A | 11/2005 |
| JP | 2005346024 A | 12/2005 |
| JP | 2006-036648 A | 2/2006 |
| JP | 2006098869 | 4/2006 |
| JP | 2006113136 | 4/2006 |
| JP | 2006160663 | 6/2006 |
| JP | 2006-213634 A | 8/2006 |
| JP | 2006259482 A | 9/2006 |
| JP | 2007019294 | 1/2007 |
| JP | 2007199653 | 8/2007 |
| JP | 2007226170 A | 9/2007 |
| JP | 2007226204 A | 9/2007 |
| JP | 2007262398 | 10/2007 |
| JP | 2007-326847 A | 12/2007 |
| JP | 2008065081 | 3/2008 |
| JP | 2008-145539 A | 6/2008 |
| JP | 2008201954 A | 9/2008 |
| JP | 2008239868 | 10/2008 |
| JP | 2009073738 A | 4/2009 |
| JP | 2009098155 A | 5/2009 |
| JP | 2009108313 | 5/2009 |
| JP | 2009-155256 A | 7/2009 |
| JP | 2009-173623 A | 8/2009 |
| JP | 2009300978 | 12/2009 |

(56) References Cited

FOREIGN PATENT DOCUMENTS

| | | |
|---|---|---|
| JP | 2010160189 | 7/2010 |
| JP | 2010170013 | 8/2010 |
| JP | 2010219295 | 9/2010 |
| JP | 2010235643 | 10/2010 |
| JP | 2011-068624 A | 4/2011 |
| JP | 2011-105887 A | 6/2011 |
| JP | 2011150023 | 8/2011 |
| JP | 20121687 | 1/2012 |
| JP | 2012-077295 A | 4/2012 |
| JP | 2012068652 | 4/2012 |
| JP | 2012083731 A | 4/2012 |
| JP | 2012145897 | 8/2012 |
| JP | 2013-068928 A | 4/2013 |
| JP | 2013064978 A | 4/2013 |
| JP | 2013-083939 A | 5/2013 |
| JP | 2013083833 A | 5/2013 |
| JP | 2013087173 A | 5/2013 |
| JP | 2013137524 A | 7/2013 |
| JP | 2013253161 A | 12/2013 |
| JP | 2014196288 A | 10/2014 |
| JP | 2014205746 | 10/2014 |
| JP | 2015-018220 A | 1/2015 |
| JP | 2015-018221 A | 1/2015 |
| JP | 2015-018223 A | 1/2015 |
| JP | 2015087115 A | 5/2015 |
| JP | 2015514691 A | 5/2015 |
| JP | 2015-127821 A | 7/2015 |
| KR | 10-2010-0095563 A | 8/2010 |
| WO | 9736960 | 10/1997 |
| WO | 0214434 | 2/2002 |
| WO | 03017002 | 2/2003 |
| WO | 2004066377 A1 | 8/2004 |
| WO | 2005029189 A1 | 3/2005 |
| WO | 2005111724 | 11/2005 |
| WO | 2006068267 A1 | 6/2006 |
| WO | 2007097457 | 8/2007 |
| WO | 2008053974 A1 | 5/2008 |
| WO | 2008137816 A2 | 11/2008 |
| WO | 2009072465 A1 | 6/2009 |
| WO | 2009119201 A1 | 10/2009 |
| WO | 2009145224 | 12/2009 |
| WO | 2011034062 A1 | 3/2011 |
| WO | 2012165507 A1 | 12/2012 |
| WO | 2013/010102 A2 | 1/2013 |
| WO | 2013/024778 A1 | 2/2013 |
| WO | 2013024777 A1 | 2/2013 |
| WO | 2013024779 A1 | 2/2013 |
| WO | 2013066067 | 5/2013 |
| WO | 2013184755 | 12/2013 |
| WO | 2014050690 | 4/2014 |
| WO | 2014123032 A1 | 8/2014 |
| WO | 2014199660 | 12/2014 |

OTHER PUBLICATIONS

T. Nakayama, M. Nomura, K. Haga, M. Ueda: "A New Three-Component Photoresist Based on Calix[4]resorcinarene Derivative, a Cross-linker, and a Photo-acid Generator" Bull. Chem. Soc. Jpn., 71, 2979 (1998).

International Search Report for PCT/JP2014/051775 dated Feb. 25, 2014 and English translation (4 pages).

U.S. Appl. No. 14/766,658, entitlted "Resist Composition, Method for Forming Resist Pattern, Polyphenol Derivative for Use in The Composition," filed Aug. 7, 2015, which entered the U.S. national phase from International Application No. PCT/JP2014/051775, filed on Jan. 28, 2014, which published as US 2015/0376157 A1 on Dec. 31, 2015.

U.S. Appl. No. 15/539,560, entitled "Compound, Resin, Material for Forming Underlayer Film for Lithography, Underlayer Film for Lithography, Pattern Forming Method, and Purification Method," filed Jun. 23, 2017, which entered the U.S. national phase from International Application No. PCT/JP2015/084907, filed on Dec. 14, 2015, which published as US 2017/0349564 A1 on Dec. 7, 2017.

U.S. Appl. No. 15/560,059, entitled "Compound, Resist Composition, and Method for Forming Resist Pattern Using It," filed Sep. 20, 2017, which entered the U.S. national phase from International Application No. PCT/JP2016/056332, filed on Mar. 2, 2016, which published as US 2018/0074406 A1 on Mar. 15, 2018.

Ahmed Munir et al., The Direct Bradsher Reaction. Part 1. Synthesis of Thiophen Analogues of Linear Polycyclic Hydrocarbons, Journal of the Chemical Society, Perkin Transactions 1,1973, pp. 1099-1103.

Areephong, Jetsuda, et al., "A concise synthesis of functionalized 7-oxa-[5]-helicenes," Tetrahedron Letters, 2004, vol. 45, pp. 3067-3070.

Bentley, K. W and Robinson, R., "A Synthesis of alpha-Anhydrotrimethylbrazilone," Tetrahedron Letters, 1959, vol. 1, Issue 2, pp. 11-14.

Brecher, Jonathan, Graphical Representation Standards for Chemical Structure Diagrams, Pure Appl. Chem., 2008, pp. 277-410, vol. 80, No. 2, Cambridge, Massachusetts.

Cameron, Donald W., et al., "Synthesis of a natural polychloro dinaphthofuran quinone," Tetrahedron Letters, 1980, vol. 21(14), pp. 1385-1386.

Chatterjea, J.N., "Experiments on the Syntheses of Furano Compounds. Part XII. Further Transformations of isoCoumaranone," Journal of the Indian Chemical Society, 1957, vol. 34, Issue 4, pp. 299-305.

Clowes, G. A., et al., "Studies of the Scholl reaction: Oxidative Dehydrogenation involving 1-Ethoxynaphthylenen and Related Compounds," J Chem. Soc (C) 2519-2526 (1968).

Dann, von Otto, and Hofmann, Hans, Synthese von ()-Brasilin, Justus Liebigs Annalen der Chemie, 1963, vol. 667, Issue 1, pp. 116-125.

English Translation of JP H01-283280 A, Nov. 14, 1989.

Ghodratbeigi Mohsen et al., "Design, modeling and synthesis of molecular tweezers with self-assembly Properties," Journal of Molecular Structure, 2011, vol. 990, No. 1, pp. 140-151.

Hagihara K. et al., "The effect of Ti-addition on plastic deformation and fracture behavior of directionally solidified NliAl/Cr(Mo) eutetic alloys," Intermetallics, 2006, vol. 14, No. 10, pp. 1326-1331.

International Search Report dated Feb. 25, 2014 for PCT/JP2012/051775 and English translation of the same (4 pages).

International Search Report dated Feb. 9, 2016, for PCT/JP2015/084907 and English translation of the same (7 pages).

International Search Report dated Mar. 25, 2014 for International Application No. PCT/JP2014/052524 with English Translation (8 pages).

International Search Report dated May 13, 2014 for International Application No. PCT/JP2014/052530 with English Translation (8 pages).

International Search Report dated Oct. 23, 2012 issued in International Application No. PCT/JP2012/070304.

International Search Report dated Sep. 11, 2012 for International Application No. PCT/JP2012/070305 with English Translation (5 pages).

International Search Report on Patentability for PCT/JP2016/056332 dated May 31, 2016; English translation submitted herewith (11 pages).

JHA Amitabh and BEAL Jennifer, "Convenient synthesis of 12H-benzo[a]xanthenes from 2-tetralone," Tetrahedron Letters, 2004, vol. 45, No. 49, pp. 8999-9001.

Journal of the Chemical Society, p. 5336-5341 (Nov. 1963).

Machine English Translation of JP 2008-239868 A, Oct. 9, 2008.

Nature, 161:930-931 (1948).

Nishiyama Tomihiro et al., Antioxidant activities of fused heterocyclic compounds, xanthene-2,7-diols with BHT or Catechol skeleton, Polymer Degradation and Stability, 1998, vol. 62, No. 3, pp. 529-534.

Ohishi Takeshi. Tetrahedron Letters 42 (2001) 2493-2496.

Osman A-M, Reactions Between Chloro-p-benzoquinones and Beta-Naphtol, Journal of Organic Chemistry, 1957, vol. 22, pp. 342-344.

Percec, Virgil, et al., Synthesis of Aromatic Polyethers by Scholl Reaction. I. Poly(1,1'-Dinaphthyl Ether Phenyl Sulfone)s and Poly(1,1'-Dinaphthyl Ether Phenyl Ketone)s, Journal of Polymer Science: Part A: Polymer Chemistry, 1988, vol. 26, pp. 783-805.

(56) References Cited

OTHER PUBLICATIONS

Percec, Virgil, et al., "Synthesis of Aromatic Polyethers by Scholl Reaction. VI. Aromatic Polyethers by Cation-Radical Polymerization of 4,4'-, 3,3'-, and 2-2'-Bis(1-naphthoxy)biphenyls and of 1,3-Bis(1-naphthoxy)benzene," Macromolecules, 1992, vol. 25(1), pp. 64-74.
Protiva, Miroslav, et al., "Potential metabolites or tricyclic neuroleptics" 3,7-dimethoxy and 7,8-dimethoxy derivatives of 10-{4-methylpiperazino )-10,11-dihydrodibenzo[b,f]thiepin, Collection of Czechoslovak Chemical Communications, 1981, vol. 46, pp. 1808-1817.
Protiva, Miroslav et al., Potential metabolites of tricyclic neuroleptics: 2,8-dihydroxy and 3,8-dihydroxy derivatives of 10-(4-methylpiperazino)-10,11-dihydrodibenzo[b,fJthiepin, Part CXXXIII in the series Neurotropic and Psychotropic Agents, Collection of Czechoslovak Chemical Communications, 1979, vol. 44, No. 10, pp. 2987-2996.
Shinji Okazaki et al., "New Trends of Photoresists", CMC Publishing Co., Ltd., Sep. 2009, p. 211-259.
Singh Ritesh and Panda Gautam, "Scandium triflate-catalyzed one-pot domino approach towards general and efficient syntheses of unsymmetrical 9-substituted xanthene derivatives," Organic & Biomolecular Chemistry, 2010, vol. 8, No. 5, pp. 1097-1105.
Sirkecioglu Okan et al., A Novel Synthesis of 14-(Hydroxymethylalkyl) Derivatives of Dibenzoxanthenes and 3,3-Dimethyl-4-(2-hydroxy-1-naphthyl)benzo[fJchroman, Journal of Heterocyclic Chemistry, Mar. 1, 1998, vol. 35, No. 2, pp. 457-460.
Sirringhaus Henning et al., Dibenzothienobisbenzothiophene—a novel fused-ring oligomer with high field-effect mobility, Journal of Materials Chemistry, 1999, vol. 9, pp. 2095-2101.
Tian-jun Liu, Ke-shen Zhang, Yong-jun Chen, Dong Wang and Chao-jun Li, "Chiral Conjugated Oligomer Based on 1, 1'-Binol With 3, 3 '-Acetylene-Phenylene-Acetylene Spacer", Chinese Journal of Polymer Science, Mar. 8, 2001, vol. 19, No. 5, p. 521-526.
Written Opinion of the International Searching Authority issued in International Application No. PCT/JP2012/070304 (including translation), dated Oct. 23, 2012.
Massif, Cedrik, et al. "New insights into the water-solubilisation of fluorophores by post-synthetic 'click' and Sonogashira reactions," Organic & Biomolecular Chemistry, vol. 10, No. 22, Apr. 2012, pp. 4430-4336.
Burnett, James C., et al. "Novel small molecule inhibitors of botulinum neurotoxin A metalloprotease activity," Biochemical and Biophysical Research Communications, vol. 310, No. 1, Oct. 2003, pp. 84-93.
European Journal of Medicinal Chemistry, published bi-monthly, Ejmcs, 13(4): 381-385 (1978).
Skandinavisches Archiv fuer Physiologie, 43: 215-243 (1923).
International Preliminary Report on Patentability issued in International Application No. PCT/JP2012/070304.
Luo, Junfei et al., "Salicylic acids as readily available starting materials for the synthesis of meta-substituted biaryls," ChemComm, 2015, vol. 51, pp. 3127-3130.
Hannuksela, Miska M. et al., "Hook for scalable extensions: video parameter set," Joint Collaborative Team on Video Coding (JCT-VC) of ITU-T SG 16 WP 3 and ISO/IEC JTC 1/SC 29/WG 11, May 2012, pp. 1-6.
U.S. Appl. No. 15/759,076, entitled "Compound, Resin, Resist Composition or Radiation-Sensitive Composition, Resist Pattern Formation Method, Method for Producing Amorphous Film, Underlayer Film Forming Material For Lithography, Composition for Underlayer Film Formation for Lithography, Method for Forming Circuit Pattern, and Purification Method," filed Mar. 9, 2018, which entered the U.S. national phase from International Application No. PCT/JP2016/076392, filed on Sep. 8, 2016, which published as US 2019/0056657 A1 on Feb. 21, 2019.

\* cited by examiner

RESIST COMPOSITION, METHOD FOR FORMING RESIST PATTERN, AND POLYPHENOL COMPOUND USED THEREIN

CROSS-REFERENCE TO RELATED APPLICATIONS

This application is a U.S. national phase application filed under 35 U.S.C. § 371 of International Application PCT/JP2016/056333, filed on Mar. 2, 2016, designating the United States, which claims priority from Japanese Application Number 2015-073265, filed Mar. 31, 2015, which are hereby incorporated herein by reference in their entirety.

FIELD OF THE INVENTION

The present invention relates to a compound having a specific structure. Also, the present invention relates to a resist composition containing the compound and a method for forming a resist pattern using it. Moreover, the present inventions relates to a method for purifying the compound.

BACKGROUND OF THE INVENTION

Conventional typical resist materials are polymer based resist materials capable of forming amorphous thin films. Examples include polymer based resist materials such as polymethyl methacrylate, polyhydroxy styrene with an acid dissociation reactive group, and polyalkyl methacrylate. A line pattern of about 45 to 100 nm is formed by irradiating a resist thin film made by coating a substrate with a solution of such a polymer based resist material with ultraviolet, far ultraviolet, electron beam, extreme ultraviolet (EUV), and X-ray or the like.

However, because polymer based resist materials have a molecular weight as large as about 10,000 to 100,000 and also wide molecular weight distribution, in lithography using a polymer based resist material, roughness occurs on a fine pattern surface; the pattern dimension becomes difficult to be controlled; and the yield decreases. Therefore, there is a limitation in miniaturization with lithography using a conventional polymer based resist material. In order to make a finer pattern, various low molecular weight resist materials have been proposed.

For example, an alkaline development type negative type radiation-sensitive composition (see, for example, Patent Literatures 1 and 2) using a low molecular weight polynuclear polyphenolic compound as a main component has been suggested; and as a candidate of a low molecular weight resist material having high heat resistance, an alkaline development type negative type radiation-sensitive composition (see, for example, Patent Literature 3 and Non Patent Literature 1) using a low molecular weight cyclic polyphenolic compound as a main component has been suggested as well.

Also, as a base compound of a resist material, a polyphenol compound is known to be capable of imparting high heat resistance despite a low molecular weight and useful for improving the resolution and roughness of a resist pattern (see, for example, Non Patent Literature 2). Also, various polyphenols are used as raw materials of thermoplastic resins such as polycarbonate and polyarylate, raw materials of thermosetting resins such as epoxy resins, curing agents, modifiers, and the like (see, for example, Patent Literatures 4 to 5).

Moreover, as resin raw materials and resin curing agents, fluorene compounds with a cardo structure that have various improved properties (such as optical properties, heat resistance, water resistance, moisture resistance, chemical resistance, electrical properties, mechanical properties, and dimensional stability) due to substitution with polyhydroxyphenol or the like are known (see, for example, Patent Literatures 6 to 9).

CITATION LIST

Patent Literature

Patent Literature 1: Japanese Patent Application Laid-Open No. 2005-326838
Patent Literature 2: Japanese Patent Application Laid-Open No. 2008-145539
Patent Literature 3: Japanese Patent Application Laid-Open No. 2009-173623
Patent Literature 4: Japanese Patent Application Laid-Open No. 2006-213634
Patent Literature 5: Japanese Patent Application Laid-Open No. 2007-326847
Patent Literature 6: Japanese Patent Application Laid-Open No. 2006-36648
Patent Literature 7: Japanese Patent Application Laid-Open No. 2009-155256
Patent Literature 8: Japanese Patent Application Laid-Open No. 2011-68624
Patent Literature 9: Japanese Patent Application Laid-Open No. 2011-105887

Non Patent Literature

Non Patent Literature 1: T. Nakayama, M. Nomura, K. Haga, M. Ueda: Bull. Chem. Soc. Jpn., 71, 2979 (1998)
Non Patent Literature 2: Shinji Okazak et al., "New Trends of Photoresists", CMC Publishing Co., Ltd., September 2009, pp. 211-259

SUMMARY OF INVENTION

However, the heat resistances of the compositions of Patent Literatures 1 and 2 are not sufficient, and the shapes of the obtained resist patterns are likely to be poor. The solubilities of the compositions of Patent Literature 3 and Non Patent Literature 1 in safe solvents used in a semiconductor production process are not sufficient, also their sensitivities are not sufficient, the shapes of the obtained resist patterns in some cases are poor, and thus a further improvement of low molecular weight resist materials is desired.

Also, Patent Literatures 4 and 5 and Non Patent Literature 2 are silent on solubility, the heat resistances of the described compounds are still not sufficient, and a further improvement of various properties such as heat resistance, water resistance, chemical resistance, electrical properties, and mechanical properties is required.

Moreover, properties such as heat resistance of the alcohol compounds of Patent Literatures 6 to 9 are not sufficient, and an alcohol compound having more improved heat resistance is desired.

An object of the present invention is to provide a resist composition which has good storage stability and thin film formability and high sensitivity and can impart a good shape to a resist pattern, and a method for forming a resist pattern using the resist composition.

Another object of the present invention is to provide a compound having high solubility in a safe solvent.

The inventors have, as a result of devoted examinations to solve the above problems, found out that a compound having a specific structure has high solubility in a safe solvent and that a resist composition containing the compound has good storage stability and thin film formability and can impart a shape to a resist pattern, and reached the present invention.

More specifically, the present invention is as follows.

[1] A compound represented by the following general formula (1):

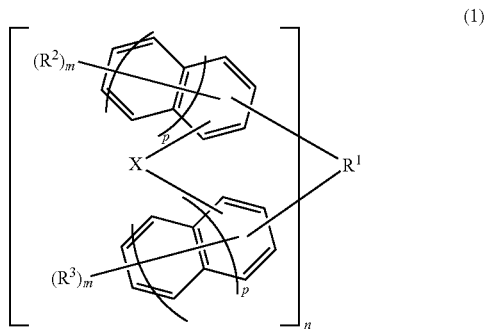

wherein each X is independently an oxygen atom, a sulfur atom, or not a crosslink; $R^1$ is a single bond or a 2n-valent group of 1 to 30 carbon atoms; $R^2$ and $R^3$ are each independently a halogen atom, a linear, branched, or cyclic alkyl group of 1 to 10 carbon atoms, an aryl group of 6 to 10 carbon atoms, an alkenyl group of 2 to 10 carbon atoms, an alkoxy group of 1 to 30 carbon atoms, a thiol group, or a hydroxy group; each m is independently an integer of 0 to 7, provided that at least one m is an integer of 1 to 7; each p is independently 0 or 1; and n is an integer of 1 to 4; provided that at least one selected from the group consisting of $R^1$, $R^2$, and $R^3$ is a group containing an iodine atom, and at least one $R^2$ and/or at least one $R^3$ is one or more selected from a hydroxy group and a thiol group.

[2] The compound according to [1], wherein X is an oxygen atom in the above general formula (1).

[3] The compound according to [1] or [2], wherein at least one $R^2$ is a hydroxy group, and at least one $R^3$ is a hydroxy group, in the above general formula (1).

[4] The compound according to any of [1] to [3], wherein one $R^2$ is a hydroxy group, and one $R^3$ is a hydroxy group, in the above general formula (1).

[5] The compound according to any of [1] to [4], wherein p is 1, and n is 1, in the above general formula (1).

[6] The compound according to [1], wherein the compound represented by the above general formula (1) is a xanthene compound represented by the following general formula (2):

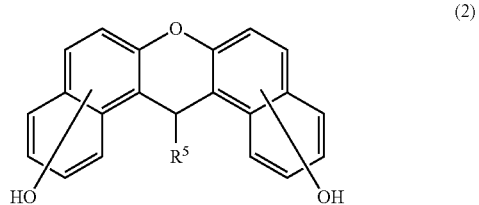

wherein $R^5$ is a halogen atom, a linear, branched, or cyclic alkyl group of 1 to 10 carbon atoms, an aryl group of 6 to 10 carbon atoms, an alkenyl group of 2 to 10 carbon atoms, and an alkoxy group of 1 to 30 carbon atoms, provided that $R^5$ is a monovalent group comprising an iodine atom.

[7] The compound according to [1], wherein the compound represented by the above general formula (1) is a xanthene compound represented by the following general formula (3):

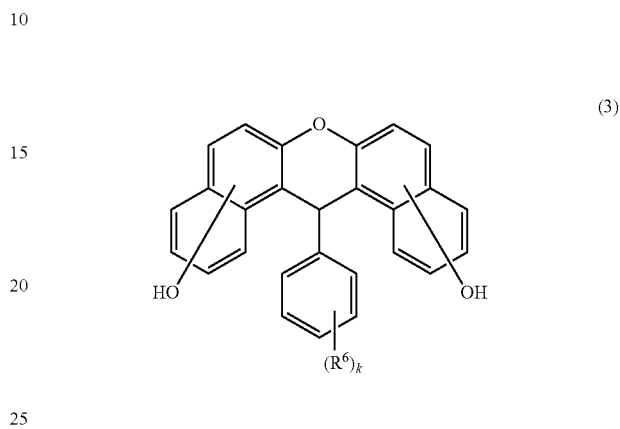

wherein each $R^6$ is independently a halogen atom, a linear, branched, or cyclic alkyl group of 1 to 10 carbon atoms, an aryl group of 6 to 10 carbon atoms, an alkenyl group of 2 to 10 carbon atoms, an alkoxy group of 1 to 30 carbon atoms, a thiol group, or a hydroxy group, and k is an integer of 1 to 5, provided that at least one $R^6$ is a monovalent group comprising an iodine atom.

[8] The compound according to [1], wherein the compound represented by the above general formula (1) is a xanthene compound represented by the following formula (3-1).

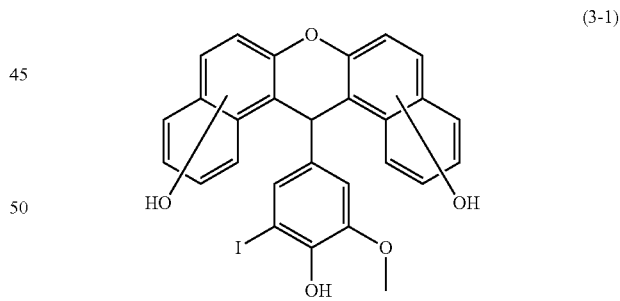

[9] A resin obtained by using the compound according to any of [1] to [8] as a monomer.

[10] The resin according to [9] obtained by reacting the compound according to any of [1] to [8] with a crosslinking compound.

[11] The resin according to [10], wherein the crosslinking compound is an aldehyde, a ketone, a carboxylic acid, a carboxylic acid halide, a halogen-containing compound, an amino compound, an imino compound, an isocyanate, or an unsaturated hydrocarbon group-containing compound.

[12] A resin having a structure represented by the following general formula (Z):

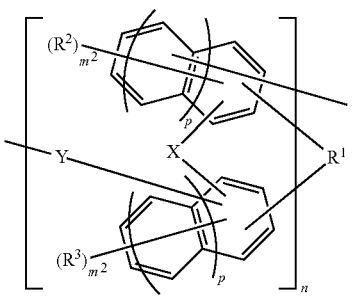

(Z)

wherein each X is independently an oxygen atom, a sulfur atom, or not a crosslink; $R^1$ is a single bond or a 2n-valent group of 1 to 30 carbon atoms; $R^2$ and $R^3$ are each independently a halogen atom, a linear, branched, or cyclic alkyl group of 1 to 10 carbon atoms, an aryl group of 6 to 10 carbon atoms, an alkenyl group of 2 to 10 carbon atoms, an alkoxy group of 1 to 30 carbon atoms, a thiol group, or a hydroxy group; each Y is independently a single bond or a linear or branched alkylene group of 1 to 20 carbon atoms; each $m^2$ is independently an integer of 0 to 6, provided that at least one $m^2$ is an integer of 1 to 6; each p is independently 0 or 1; and n is an integer of 1 to 4; provided that at least one selected from the group consisting of $R^1$, $R^2$, and $R^3$ is a group comprising an iodine atom, and at least one $R^2$ and/or at least one $R^3$ is one or more selected from a hydroxy group and a thiol group.

[13] A resist composition comprising the compound according to any of [1] to [8] and/or the resin according to any of [9] to [12].

[14] The resist composition according to [13], further comprising a solvent.

[15] The resist composition according to [13] or [14], further comprising an acid generating agent.

[16] The resist composition according to any of [13] to [15], further comprising an acid crosslinking agent.

[17] A method for forming a resist pattern, comprising the steps of coating a substrate with the resist composition according to any of [13] to [16], thereby forming a resist film; exposing the formed resist film; and developing the exposed resist film.

[18] A method for producing the compound according to [1], comprising the step of reacting a compound represented by the following general formula (4) with an aldehyde of 1 to 19 carbon atoms in the presence of an acid catalyst, wherein at least one selected from the group consisting of $R^7$ in the following general formula (4) and the aldehyde comprises an iodine atom:

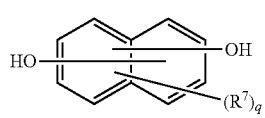

(4)

wherein each $R^7$ is independently a halogen atom or an alkyl group of 1 to 4 carbon atoms, and q is an integer of 0 to 5.

[19] A method for producing the xanthene compound according to [6], comprising the step of reacting a compound represented by the following general formula (5) with an aldehyde of 1 to 19 carbon atoms in the presence of an acid catalyst, wherein the aldehyde comprises an iodine atom.

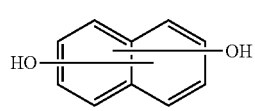

(5)

[20] A purification method comprising the steps of:
obtaining a solution (A) by dissolving the compound according to any of [1] to [8] or the resin according to any of [9] to [12] in a solvent; and
extracting impurities in the compound or the resin by bringing the obtained solution (A) into contact with an acidic aqueous solution (a first extraction step), wherein
the solvent used in the step of obtaining the solution (A) comprises an organic solvent that does not inadvertently mix with water.

[21] The purification method according to [20], wherein
the acidic aqueous solution is an aqueous mineral acid solution or an aqueous organic acid solution;
the aqueous mineral acid solution is one or more aqueous mineral acid solutions selected from the group consisting of hydrochloric acid, sulfuric acid, nitric acid, and phosphoric acid; and
the aqueous organic acid solution is one or more aqueous organic acid solutions selected from the group consisting of acetic acid, propionic acid, oxalic acid, malonic acid, succinic acid, fumaric acid, maleic acid, tartaric acid, citric acid, methanesulfonic acid, phenolsulfonic acid, p-toluenesulfonic acid, and trifluoroacetic acid.

[22] The purification method according to [20] or [21], wherein the organic solvent that does not inadvertently mix with water is one or more organic solvents selected from the group consisting of toluene, 2-heptanone, cyclohexanone, cyclopentanone, methyl isobutyl ketone, propylene glycol monomethyl ether acetate, and ethyl acetate.

[23] The purification method according to any of [20] to [22], comprising the step of extracting impurities in the compound or the resin by further bringing a solution phase comprising the compound or the resin into contact with water after the first extraction step (a second extraction step).

The compound of the present invention has high solubility in a safe solvent, and with the compound of the present invention, it is possible to provide a resist composition which has good storage stability and thin film formability and imparts a good shape to a resist pattern, and a method for forming a resist pattern using the composition.

DESCRIPTION OF EMBODIMENTS

Hereinafter, an embodiment of the present invention will be described (hereinafter, referred to as "present embodiment"). The present embodiment is given in order to illustrate the present invention. The present invention is not limited to only the present embodiment.

[Compound]

The compound of the present embodiment is represented by the following general formula (1).

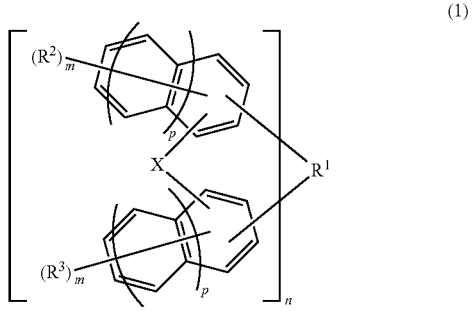

(1)

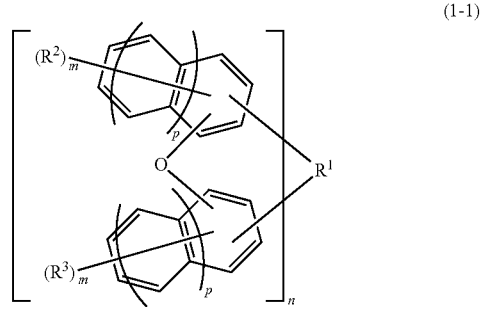

(1-1)

In the above general formula (1), each X is independently an oxygen atom, a sulfur atom, or not a crosslink, and each aromatic ring is bonded to any position via this X. $R^1$ is a single bond or a 2n-valent group of 1 to 30 carbon atoms, and each aromatic ring is bonded to any position via this $R^1$. Herein, the 2n-valent group may have an alicyclic hydrocarbon group, a double bond, a hetero atom, or an aromatic group of 6 to 30 carbon atoms. $R^2$ and $R^3$ are each independently a monovalent substituent selected from the group consisting of a halogen atom, a linear, branched, or cyclic alkyl group of 1 to 10 carbon atoms, an aryl group of 6 to 10 carbon atoms, an alkenyl group of 2 to 10 carbon atoms, an alkoxy group of 1 to 30 carbon atoms, a thiol group, and a hydroxy group, and m $R^2$ and m $R^3$ are bonded to any positions of the aromatic rings. Herein, at least one selected from the group consisting of $R^1$, $R^2$, and $R^3$ is a group containing an iodine atom, and at least one $R^2$ and/or at least one $R^3$ is one or more selected from a hydroxy group and a thiol group. Also, each m is independently an integer of 0 to 7, provided that at least one m is an integer of 1 to 7. Each p is independently 0 or 1, and n is an integer of 1 to 4.

The "at least one selected from the group consisting of $R^1$, $R^2$, and $R^3$" means "at least one group selected from the group consisting of $R^1$, $R^2$, and $R^3$", and does not mean "at least one kind of group selected from the group consisting of $R^1$, $R^2$, and $R^3$".

The above 2n-valent group refers to an alkylene group of 1 to 30 carbon atoms (n=1), an alkanetetrayl group of 1 to 30 carbon atoms (n=2), an alkanehexayl group of 2 to 30 carbon atoms (n=3), or an alkaneoctayl group of 3 to 30 carbon atoms (n=4). Examples of the 2n-valent group include hydrocarbon groups having a linear, branched, or cyclic structure.

Also, the 2n-valent group may have an alicyclic hydrocarbon group, a double bond, a hetero atom, or an aromatic group of 6 to 30 carbon atoms. Herein, the alicyclic hydrocarbon group also includes bridged alicyclic hydrocarbon groups.

Herein, the compound represented by the above formula (1) is preferably a compound in which X is an oxygen atom from the viewpoint of the supply of raw materials and the suppression of device contamination during resist film exposure, and, specifically, is preferably a compound represented by the following formula (1-1).

In the above formula (1-1), $R^1$, $R^2$, $R^3$, m, n, and p are as defined in the description of the above formula (1).

Also, from the viewpoint of solubility in an organic solvent, it is preferable for the compound represented by the above general formula (1) that at least one $R^2$ is a hydroxy group and at least one $R^3$ is a hydroxy group, and, specifically, a compound represented by, for example, the following formula (1-2) is more preferable.

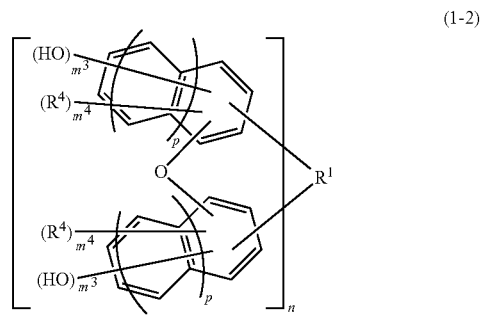

(1-2)

In the above formula (1-2), $R^1$, p, and n are as defined in the description of the above formula (1), and $R^4$ is as defined for $R^2$ in the description of the above formula (1) except that the hydroxy group is excluded. Also, at least one selected from the group consisting of $R^1$ and $R^4$ is a group containing an iodine atom. Each $m^3$ is independently an integer of 1 to 6, each $m^4$ is independently an integer of 0 to 5, and $m^3+m^4$ is an integer of 1 to 6.

From the viewpoint of further solubility in an organic solvent, it is more preferable for the compound represented by the above general formula (1) that one $R^2$ is a hydroxy group and one $R^3$ is a hydroxy group, and, specifically, a compound represented by, for example, the following formula (1-3) is more preferable.

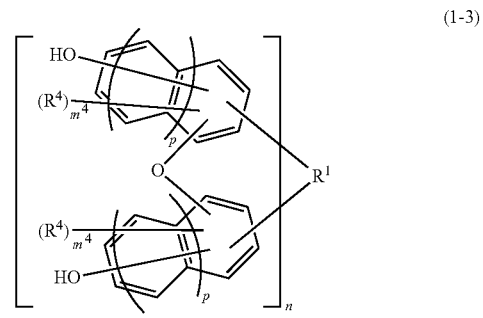

(1-3)

In the above formula (1-3), $R^1$, p, and n are as defined in the description of the above formula (1), and $R^4$ and $m^4$ are as defined in the description of the above formula (1-2). Also, at least one selected from the group consisting of $R^1$ and $R^4$ is a group containing an iodine atom.

Also, from the viewpoint of having a low molecular weight, it is particularly preferable for the compound represented by the above formula (1) to have p=1 and n=1 in the above formula (1), and, specifically, a compound represented by, for example, the following formula (1-4) is particularly preferable.

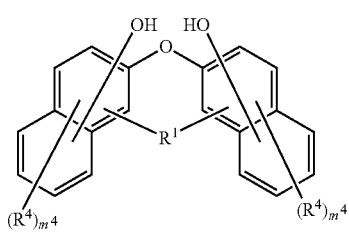

(1-4)

In the above formula (1-4), $R^1$ is as defined in the description of the above formula (1), and $R^4$ and $m^4$ are as defined in the description of the above formula (1-2). Also, at least one selected from the group consisting of $R^1$ and $R^4$ is a group containing an iodine atom.

Also, it is particularly preferable that the compound represented by the above formula (1) is a xanthene compound represented by the following formula (2) from the viewpoint of heat resistance.

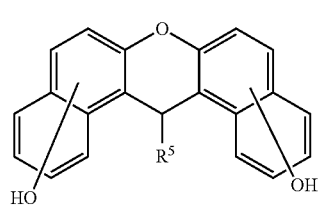

(2)

In the above formula (2), $R^5$ is a halogen atom, a linear, branched, or cyclic alkyl group of 1 to 10 carbon atoms, an aryl group of 6 to 10 carbon atoms, an alkenyl group of 2 to 10 carbon atoms, and an alkoxy group of 1 to 30 carbon atoms, provided that $R^5$ is a monovalent group containing an iodine atom.

Specific examples of the compound represented by the above general formula (1) include, but not limited to, the followings.

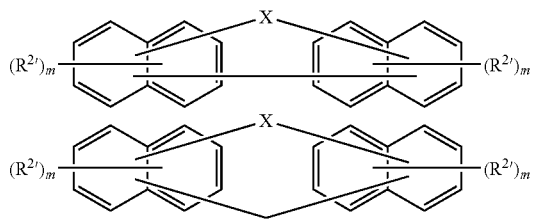

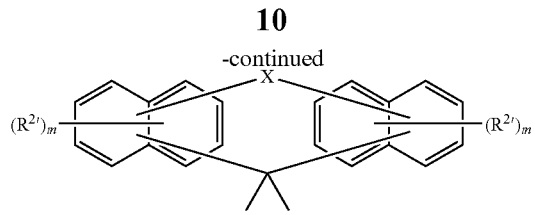

In the above formulae, X is as defined in the description of the above formula (1) and is preferably an oxygen atom from the viewpoint of the suppression of device contamination during resist film exposure; $R^{2'}$ is the same as $R^2$ defined in the description of the above formula (1), provided that at least one $R^{2'}$ is a monovalent group containing an iodine atom; and each m is independently an integer of 1 to 6.

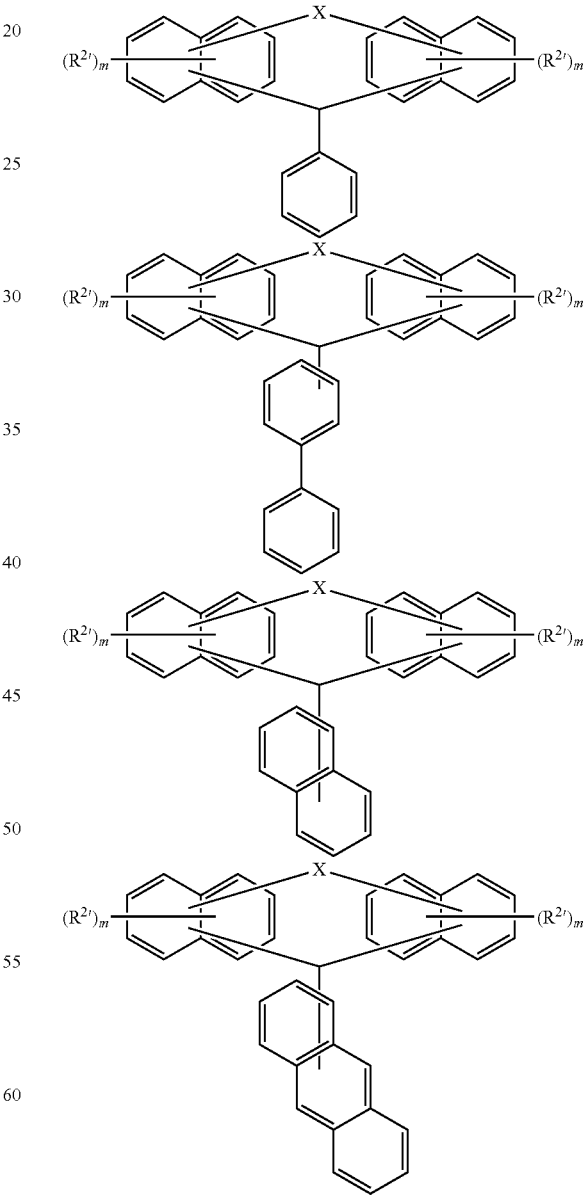

In the above formulae, X is as defined in the description of the above formula (1) and is preferably an oxygen atom from the viewpoint of the suppression of device contamination during resist film exposure; $R^{2'}$ is the same as $R^2$ defined in the description of the above formula (1), provided that at least one $R^{2'}$ is a monovalent group containing an iodine atom; and each m is independently an integer of 1 to 6.

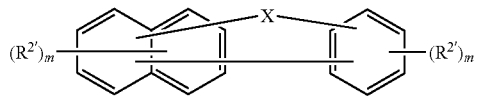

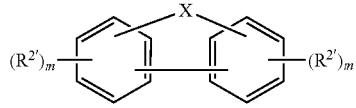

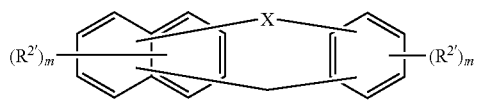

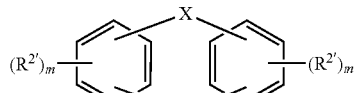

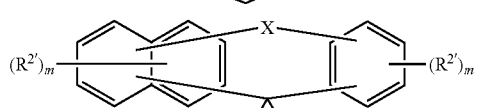

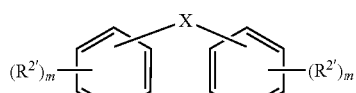

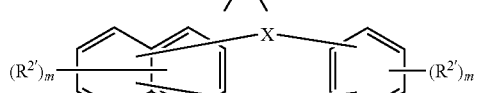

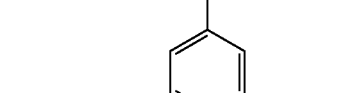

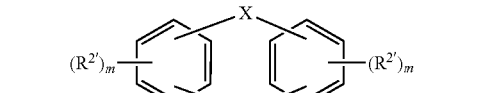

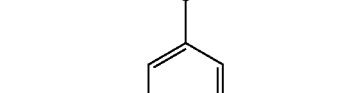

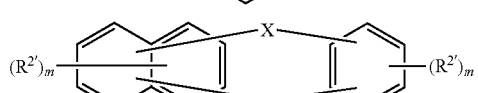

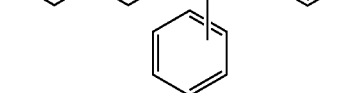

-continued

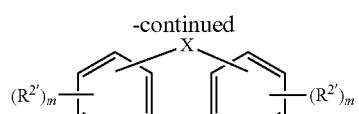

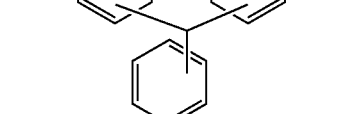

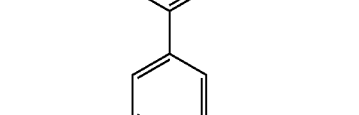

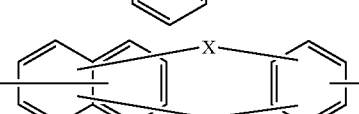

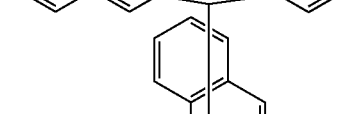

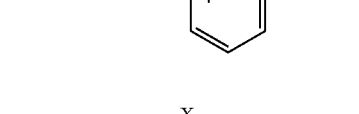

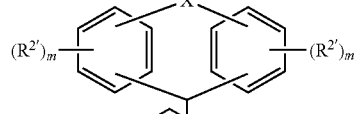

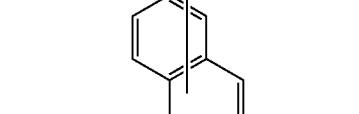

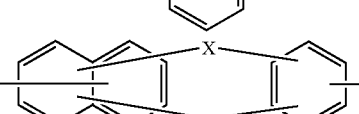

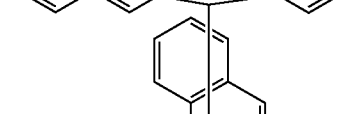

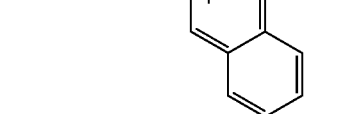

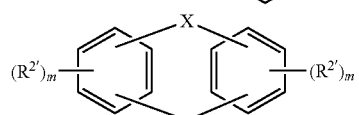

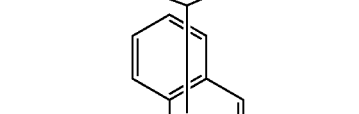

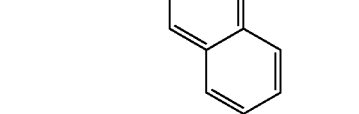

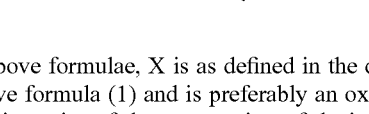

In the above formulae, X is as defined in the description of the above formula (1) and is preferably an oxygen atom from the viewpoint of the suppression of device contamination during resist film exposure; $R^{2'}$ is the same as $R^2$ defined in the description of the above formula (1), provided that at least one $R^{2'}$ is a monovalent group containing an iodine atom; and each m is independently an integer of 1 to 4.

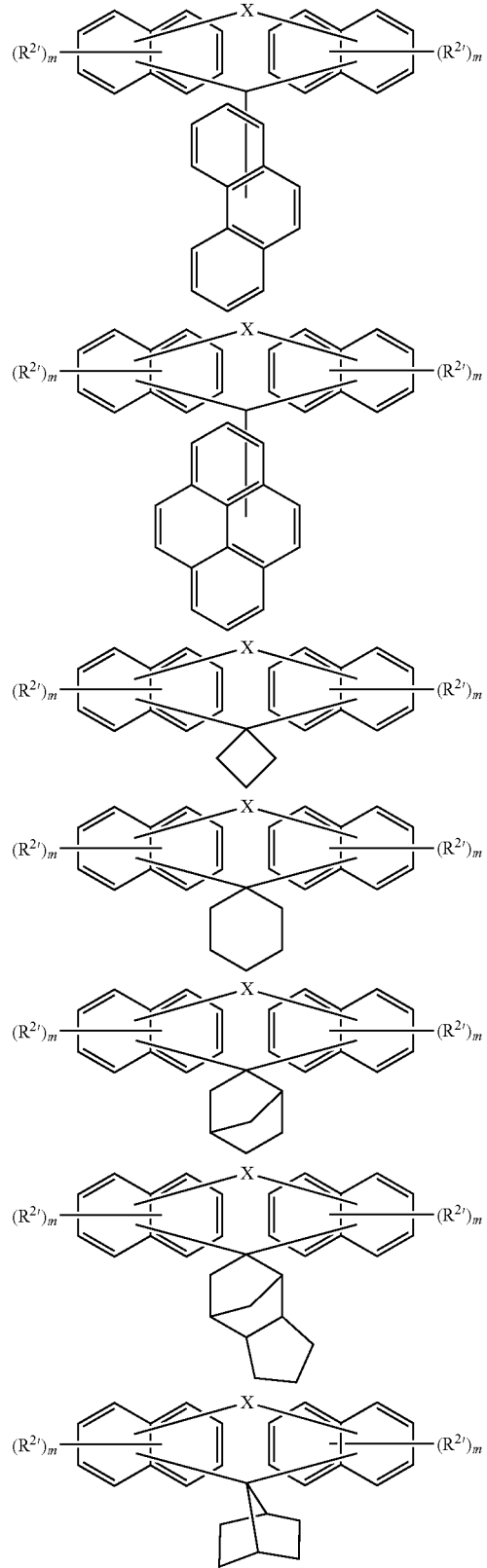

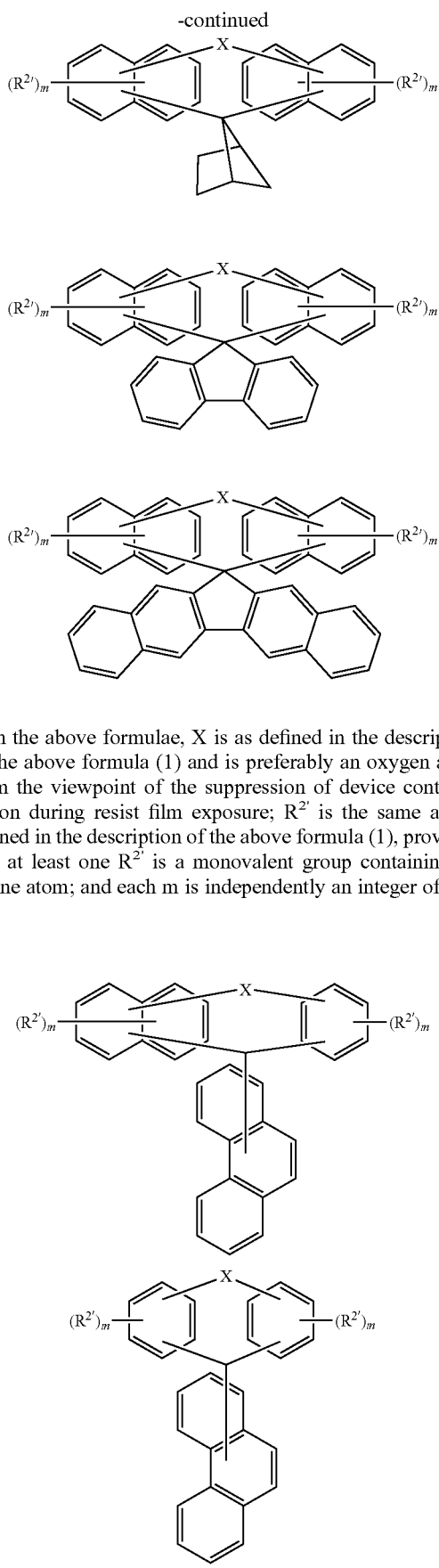

In the above formulae, X is as defined in the description of the above formula (1) and is preferably an oxygen atom from the viewpoint of the suppression of device contamination during resist film exposure; $R^{2'}$ is the same as $R^2$ defined in the description of the above formula (1), provided that at least one $R^{2'}$ is a monovalent group containing an iodine atom; and each m is independently an integer of 1 to 6.

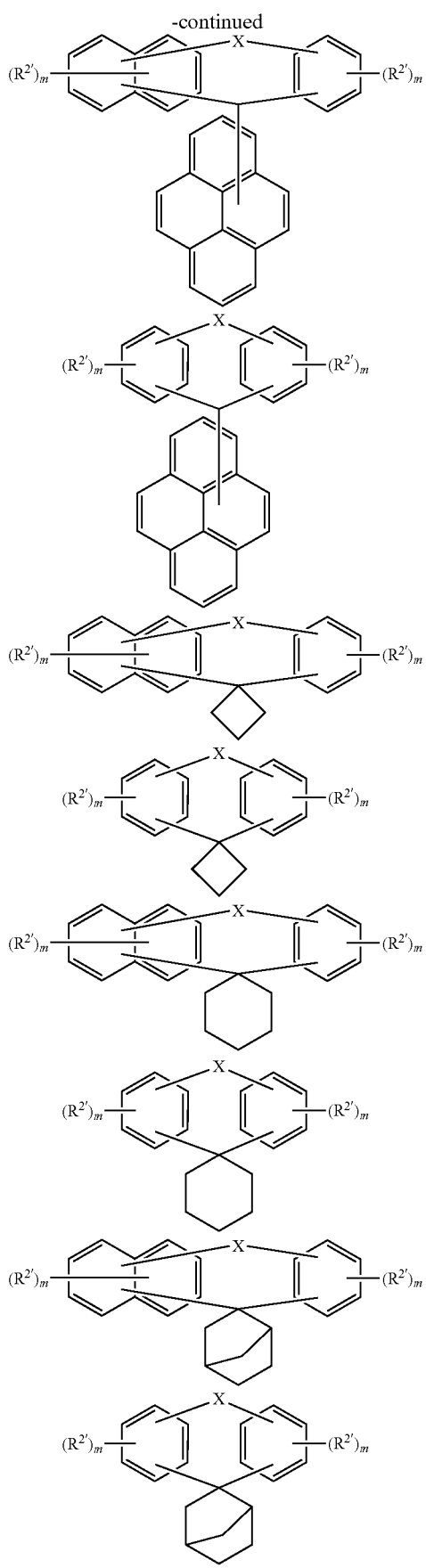
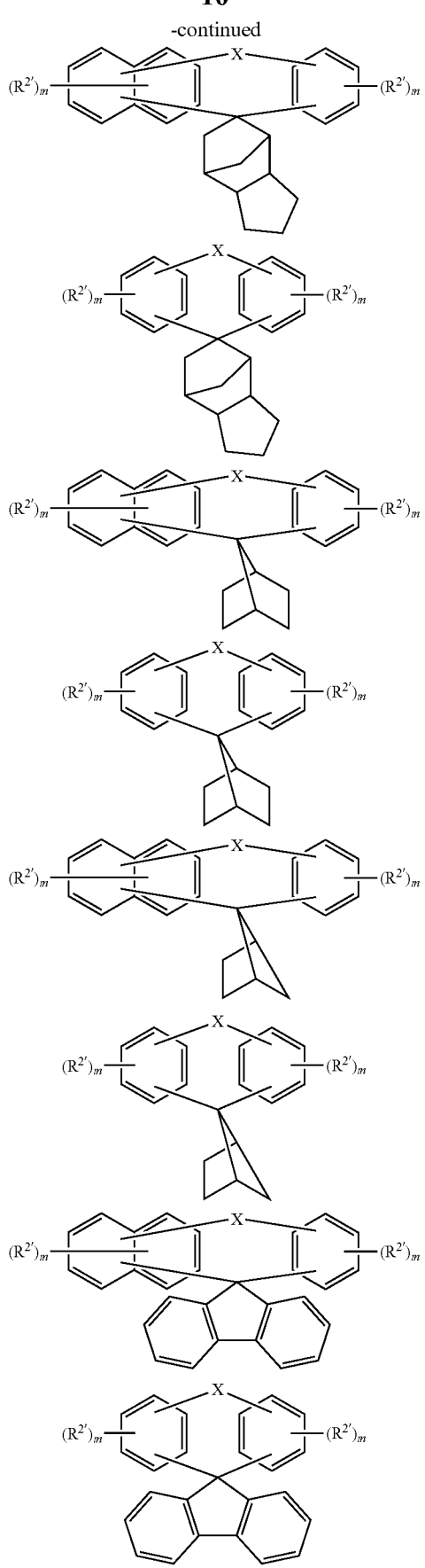

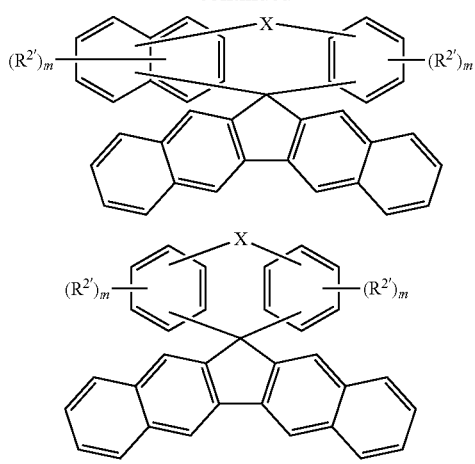

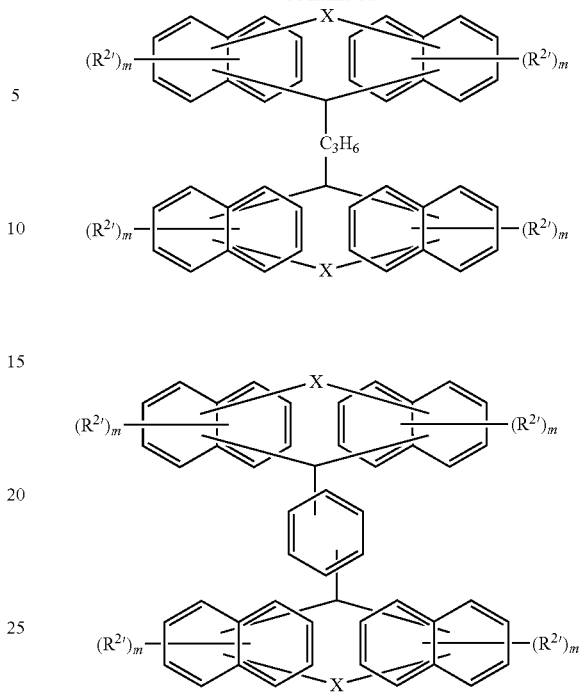

In the above formulae, X is as defined in the description of the above formula (1) and is preferably an oxygen atom from the viewpoint of the suppression of device contamination during resist film exposure; $R^{2'}$ is the same as $R^2$ defined in the description of the above formula (1), provided that at least one $R^{2'}$ is a monovalent group containing an iodine atom; and each m is independently an integer of 1 to 4.

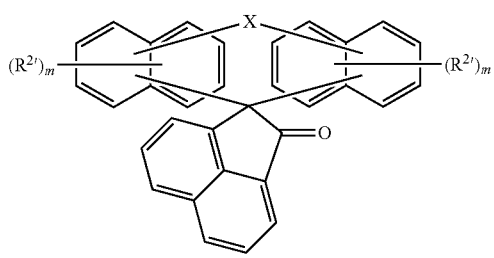

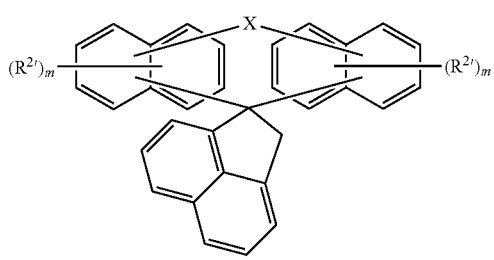

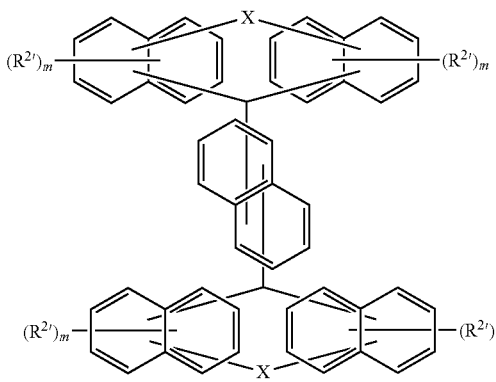

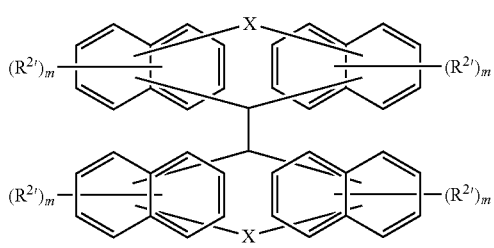

In the above formulae, X is as defined in the description of the above formula (1) and is preferably an oxygen atom from the viewpoint of the suppression of device contamination during resist film exposure; $R^{2'}$ is the same as $R^2$ defined in the description of the above formula (1), provided that at least one $R^{2'}$ is a monovalent group containing an iodine atom; and each m is independently an integer of 1 to 6.

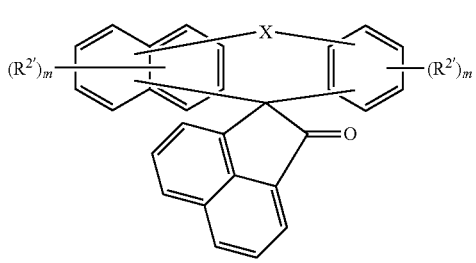

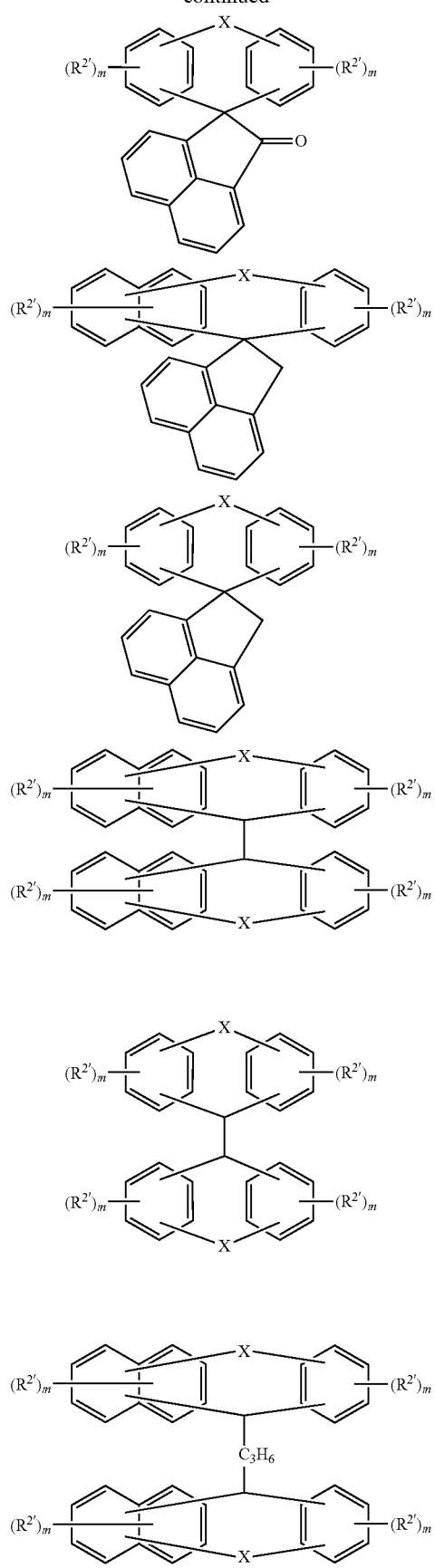
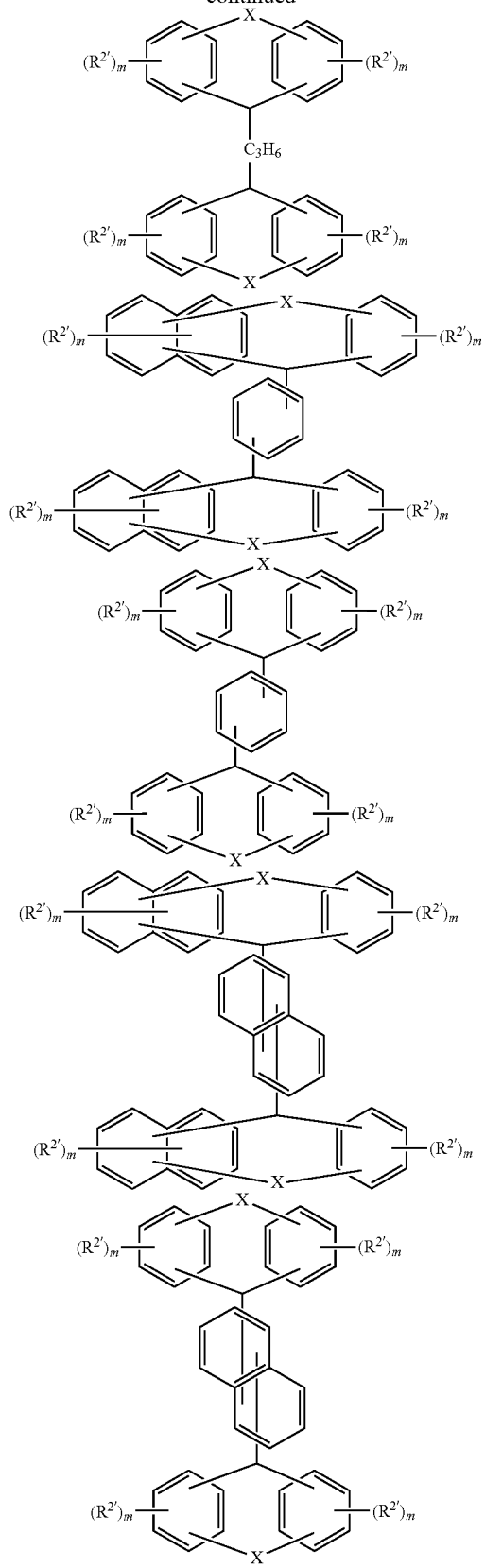
In the above formulae, X is as defined in the description of the above formula (1) and is preferably an oxygen atom from the viewpoint of the suppression of device contamination during resist film exposure; $R^{2'}$ is the same as $R^2$ defined in the description of the above formula (1), provided that at least one $R^{2'}$ is a monovalent group containing an iodine atom; and each m is independently an integer of 1 to 4.

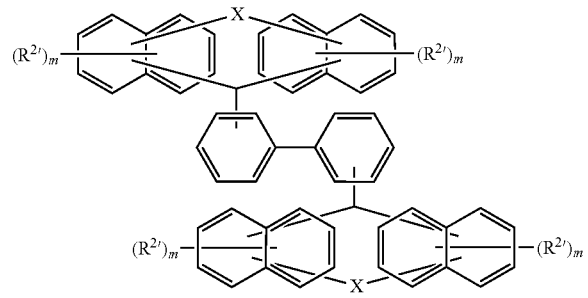

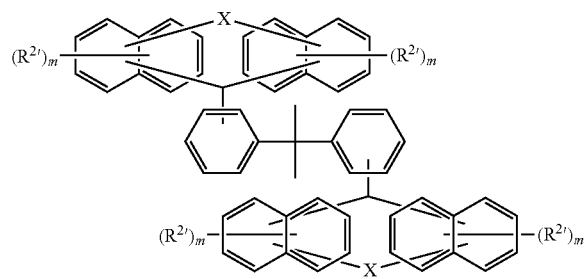

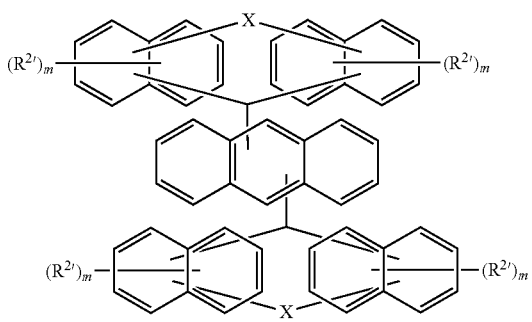

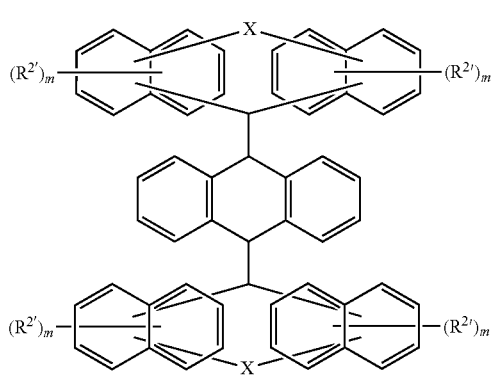

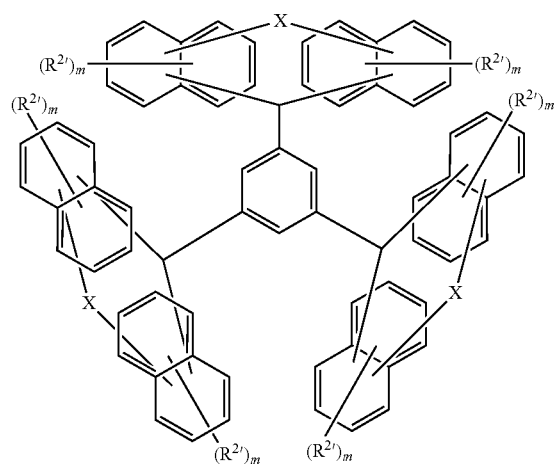

In the above formulae, X is as defined in the description of the above formula (1) and is preferably an oxygen atom from the viewpoint of the suppression of device contamination during resist film exposure; $R^{2'}$ is the same as $R^2$ defined in the description of the above formula (1), provided that at least one $R^{2'}$ is a monovalent group containing an iodine atom; and each m is independently an integer of 1 to 6.

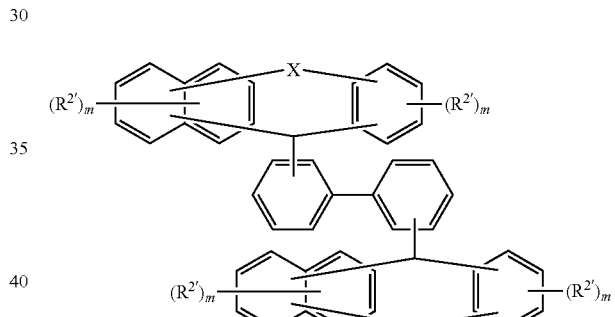

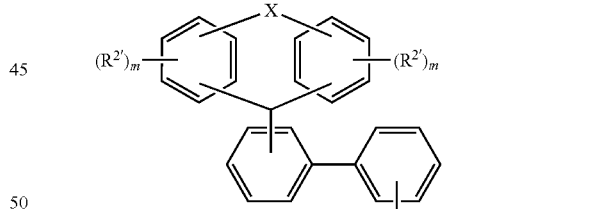

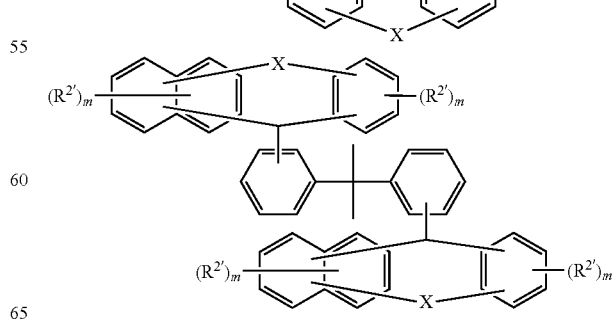

-continued

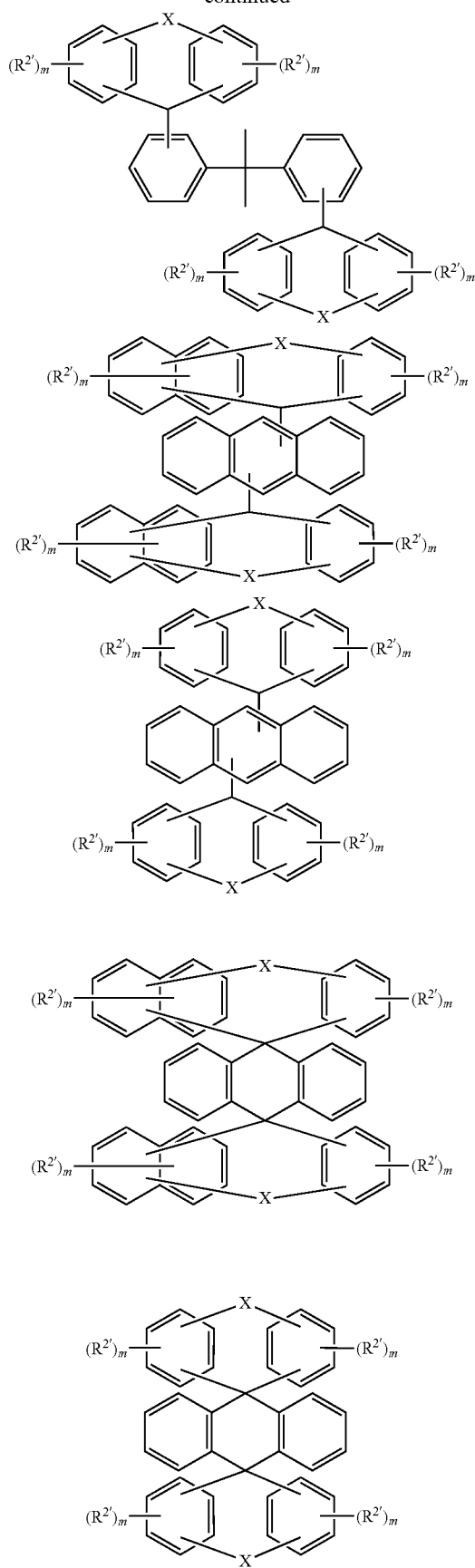

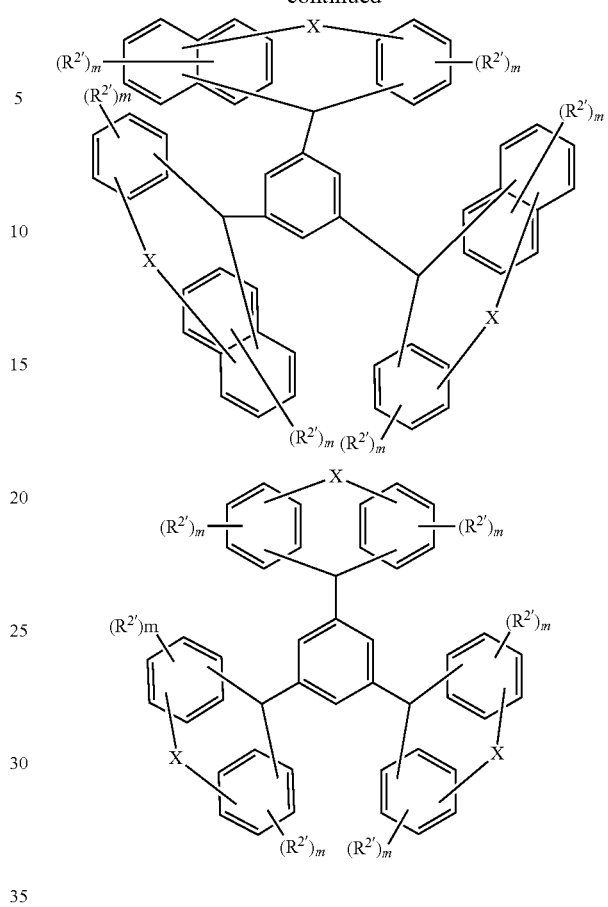

In the above formulae, X is as defined in the description of the above formula (1) and is preferably an oxygen atom from the viewpoint of the suppression of device contamination during resist film exposure; $R^{2'}$ is the same as $R^2$ defined in the description of the above formula (1), provided that at least one $R^{2'}$ is a monovalent group containing an iodine atom; and each m is independently an integer of 1 to 4.

Specific examples of the compound represented by the above formula (1) further include, but not limited to, the followings.

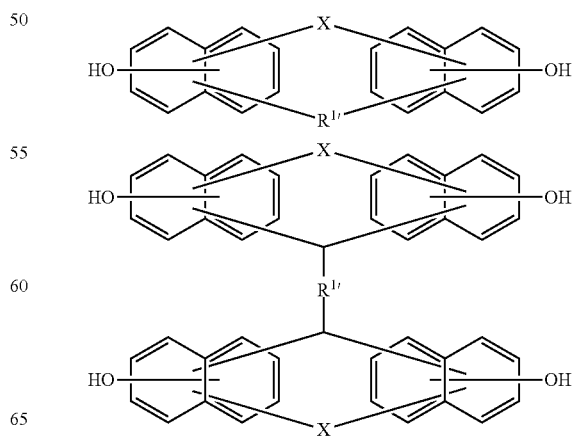

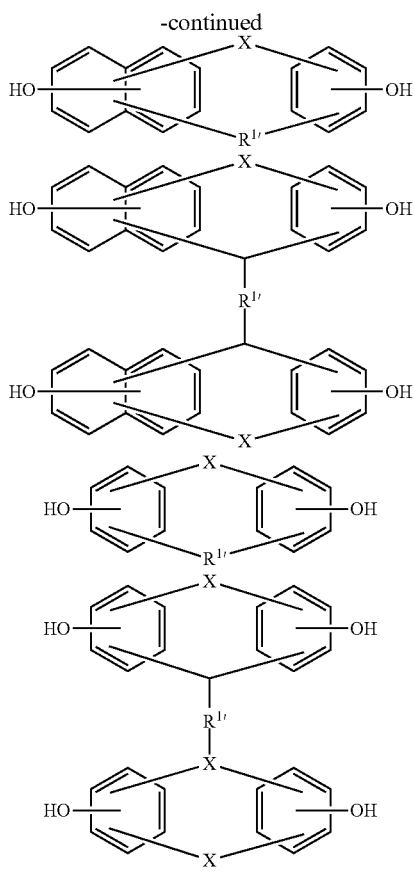

In the above formulae, X is as defined in the description of the above formula (1) and is preferably an oxygen atom from the viewpoint of the suppression of device contamination during resist film exposure; and $R^{1'}$ is the same as $R^1$ defined in the description of the above formula (1), provided that at least one $R^{1'}$ is a divalent group containing an iodine atom.

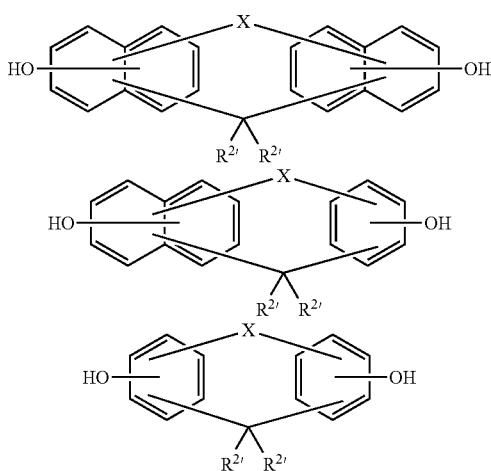

In the above formulae, X is as defined in the description of the above formula (1) and is preferably an oxygen atom from the viewpoint of the suppression of device contamination during resist film exposure; and $R^{2'}$ is the same as $R^2$ defined in the description of the above formula (1), provided that at least one $R^{2'}$ is a monovalent group containing an iodine atom.

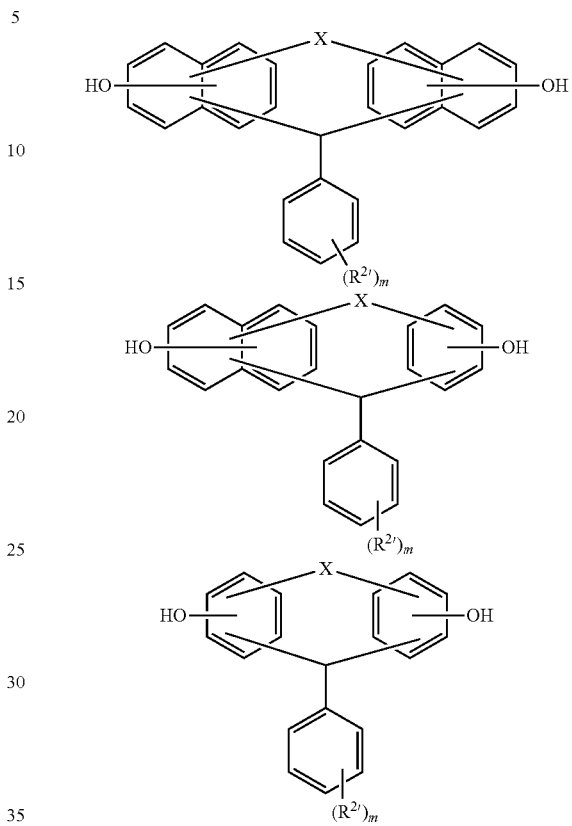

In the above formulae, X is as defined in the description of the above formula (1) and is preferably an oxygen atom from the viewpoint of the suppression of device contamination during resist film exposure; $R^{2'}$ is the same as $R^2$ defined in the description of the above formula (1), provided that at least one $R^{2'}$ is a monovalent group containing an iodine atom; and m is an integer of 1 to 5.

Especially, a xanthene compound represented by the following general formula (3) is preferable. Such a xanthene compound has higher solubility in a safe solvent, and thus a resist composition can be obtained which has better storage stability and thin film formability and imparts a better shape to a resist pattern.

(3)

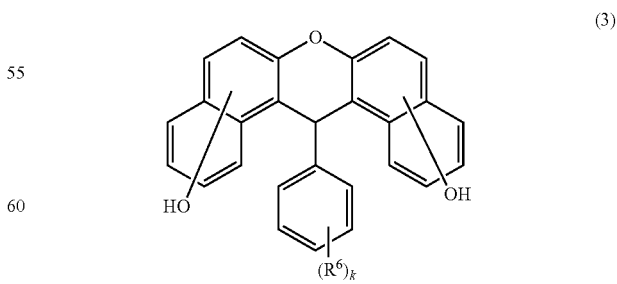

In the above general formula (3), each $R^6$ is independently a halogen atom, a linear, branched, or cyclic alkyl group of 1 to 10 carbon atoms, an aryl group of 6 to 10 carbon atoms, an alkenyl group of 2 to 10 carbon atoms, an alkoxy group of 1 to 30 carbon atoms, a thiol group, or a hydroxy group, and k is an integer of 1 to 5, provided that at least one $R^6$ is a monovalent group containing an iodine atom.

In particular, a xanthene compound represented by the following general formula (3-1) is preferable. Such a xanthene compound has even higher solubility in a safe solvent, and thus a resist composition can be obtained which has extremely good storage stability and thin film formability and imparts an extremely good shape to a resist pattern.

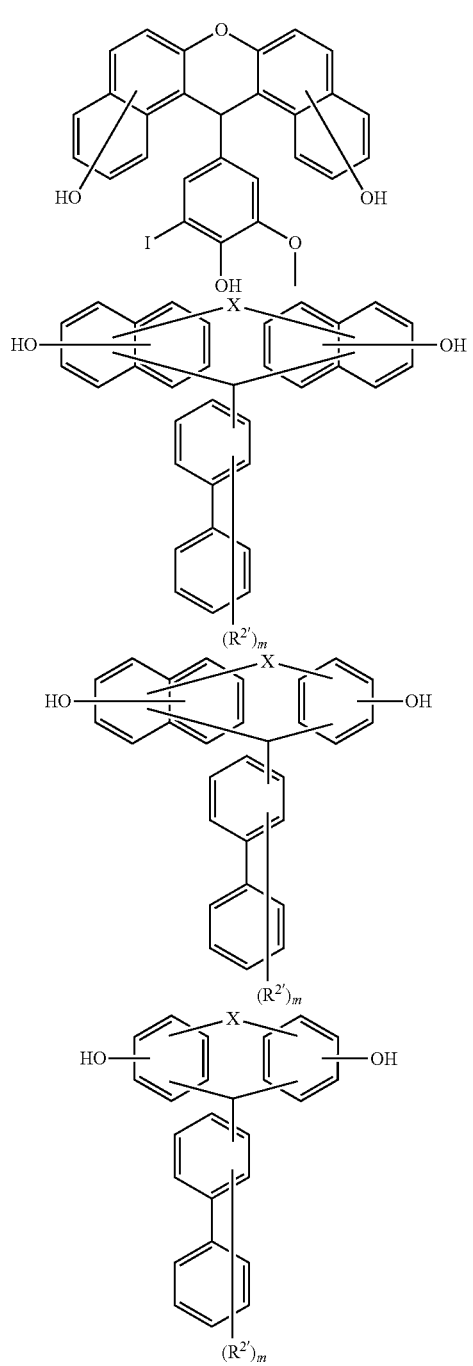

(3-1)

In the above formulae, X is as defined in the description of the above formula (1) and is preferably an oxygen atom from the viewpoint of the suppression of device contamination during resist film exposure; $R^{2'}$ is the same as $R^2$ defined in the description of the above formula (1), provided that at least one $R^{2'}$ is a monovalent group containing an iodine atom; and m is an integer of 1 to 9.

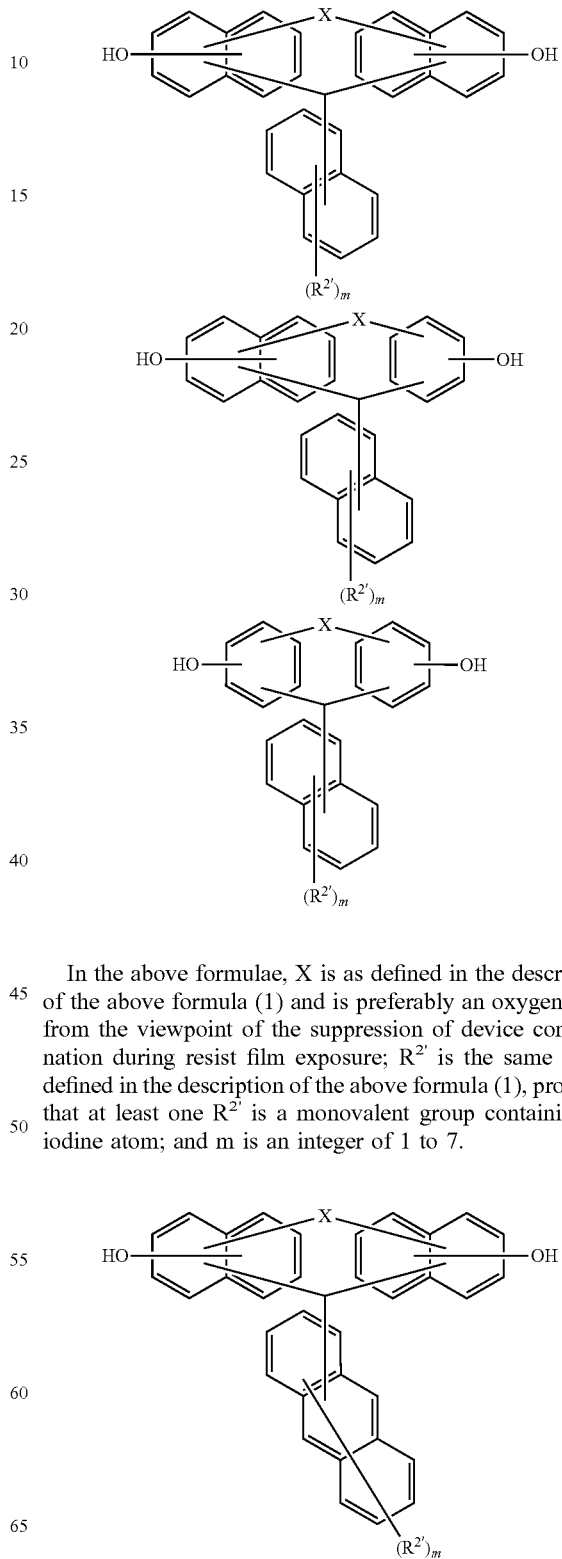

In the above formulae, X is as defined in the description of the above formula (1) and is preferably an oxygen atom from the viewpoint of the suppression of device contamination during resist film exposure; $R^{2'}$ is the same as $R^2$ defined in the description of the above formula (1), provided that at least one $R^{2'}$ is a monovalent group containing an iodine atom; and m is an integer of 1 to 7.

-continued

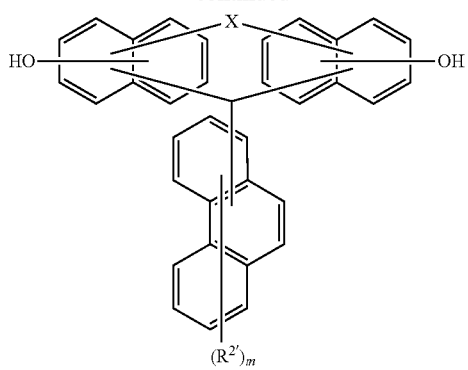

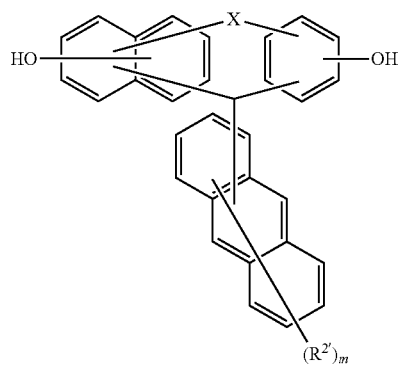

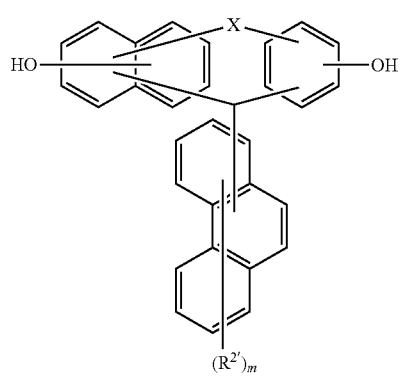

-continued

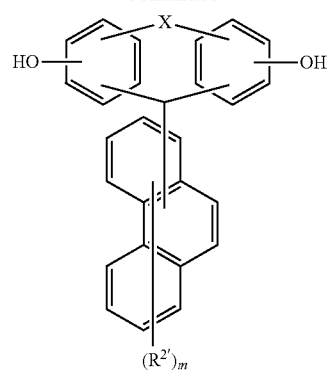

In the above formulae, X is as defined in the description of the above formula (1) and is preferably an oxygen atom from the viewpoint of the suppression of device contamination during resist film exposure; $R^{2'}$ is the same as $R^2$ defined in the description of the above formula (1), provided that at least one $R^{2'}$ is a monovalent group containing an iodine atom; and m is an integer of 1 to 9.

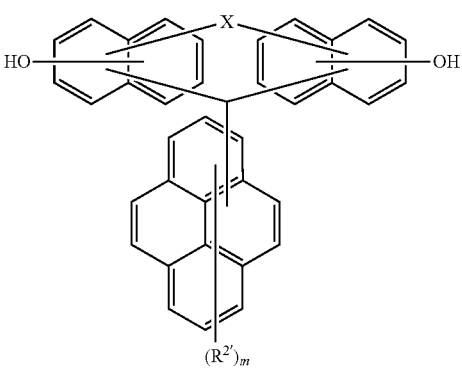

-continued

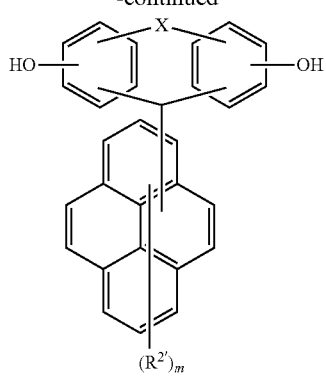

In the above formulae, X is as defined in the description of the above formula (1) and is preferably an oxygen atom from the viewpoint of the suppression of device contamination during resist film exposure; $R^{2'}$ is the same as $R^2$ defined in the description of the above formula (1), provided that at least one $R^{2'}$ is a monovalent group containing an iodine atom; and m is an integer of 1 to 9.

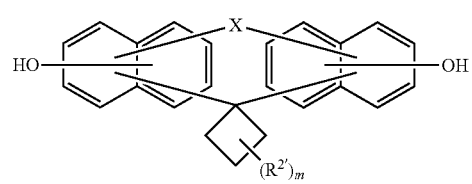

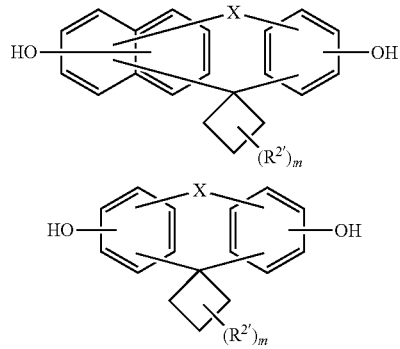

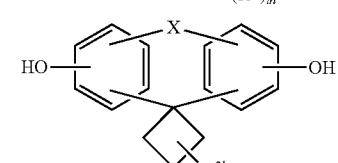

In the above formulae, X is as defined in the description of the above formula (1) and is preferably an oxygen atom from the viewpoint of the suppression of device contamination during resist film exposure; $R^{2'}$ is the same as $R^2$ defined in the description of the above formula (1), provided that at least one $R^{2'}$ is a monovalent group containing an iodine atom; and m is an integer of 1 to 6.

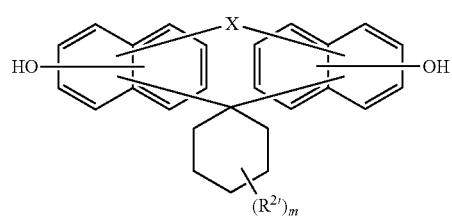

-continued

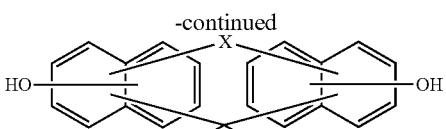

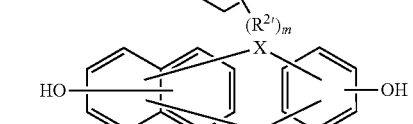

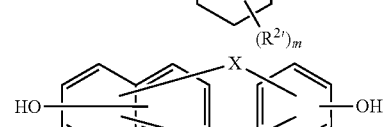

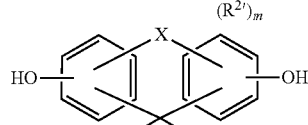

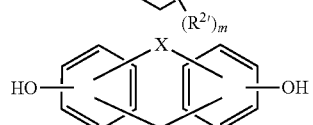

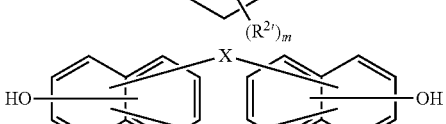

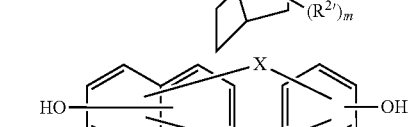

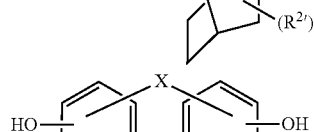

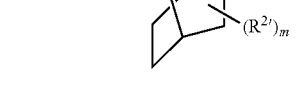

In the above formulae, X is as defined in the description of the above formula (1) and is preferably an oxygen atom from the viewpoint of the suppression of device contamination during resist film exposure; $R^{2'}$ is the same as $R^2$ defined in the description of the above formula (1), provided that at least one $R^{2'}$ is a monovalent group containing an iodine atom; and m is an integer of 1 to 10.

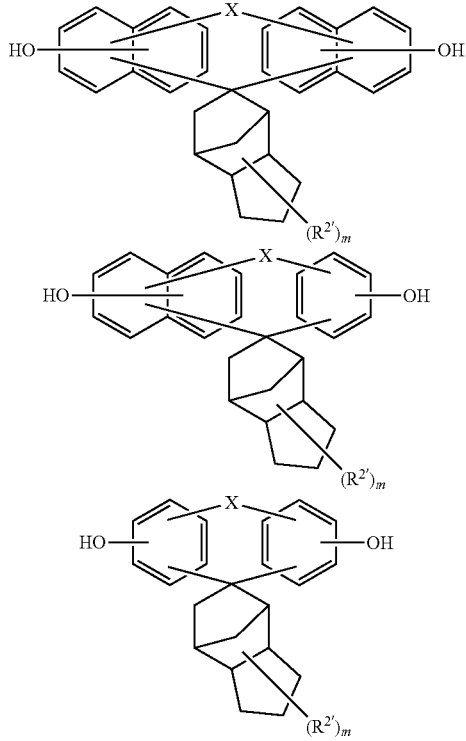

In the above formulae, X is as defined in the description of the above formula (1) and is preferably an oxygen atom from the viewpoint of the suppression of device contamination during resist film exposure; $R^{2'}$ is the same as $R^2$ defined in the description of the above formula (1), provided that at least one $R^{2'}$ is a monovalent group containing an iodine atom; and m is an integer of 1 to 14.

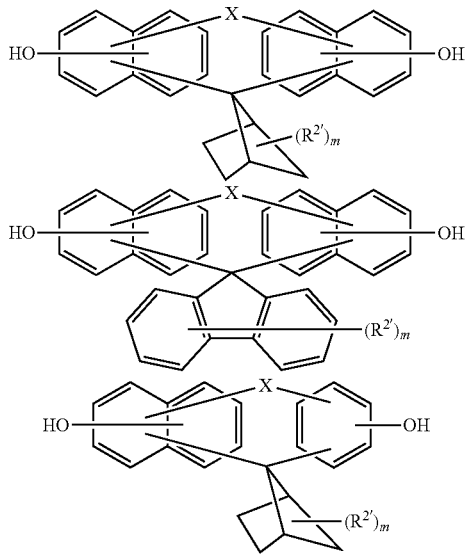

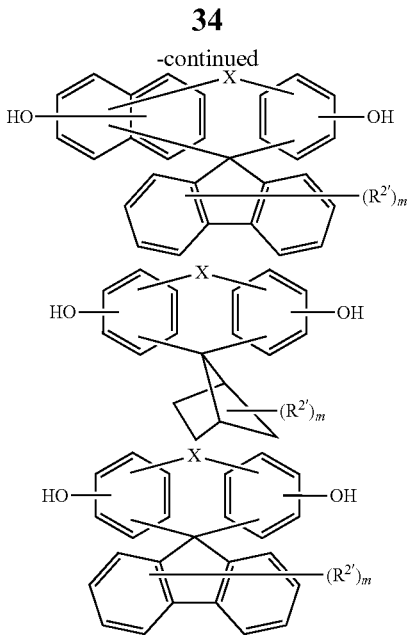

In the above formulae, X is as defined in the description of the above formula (1) and is preferably an oxygen atom from the viewpoint of the suppression of device contamination during resist film exposure; $R^{2'}$ is the same as $R^2$ defined in the description of the above formula (1), provided that at least one $R^{2'}$ is a monovalent group containing an iodine atom; and m is an integer of 1 to 8.

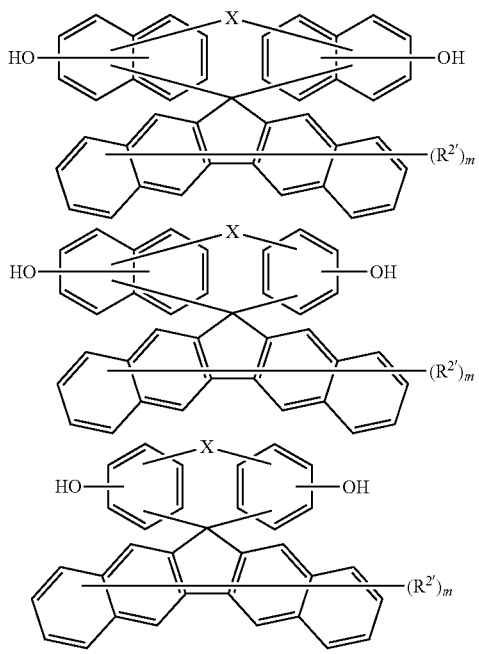

In the above formulae, X is as defined in the description of the above formula (1) and is preferably an oxygen atom from the viewpoint of the suppression of device contamination during resist film exposure; $R^{2'}$ is the same as $R^2$ defined in the description of the above formula (1), provided that at least one $R^{2'}$ is a monovalent group containing an iodine atom; and m is an integer of 1 to 12.

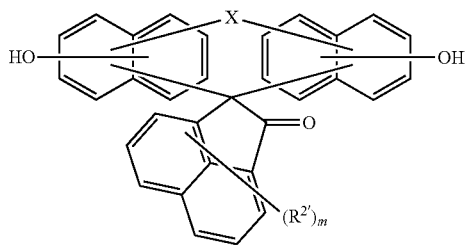

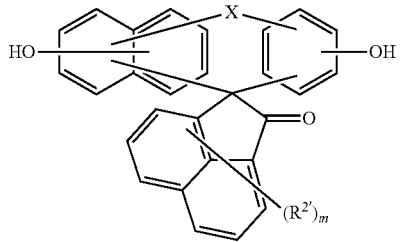

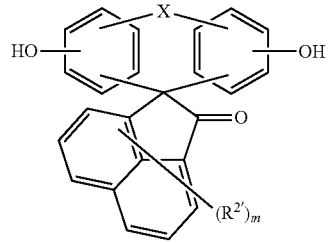

In the above formulae, X is as defined in the description of the above formula (1) and is preferably an oxygen atom from the viewpoint of the suppression of device contamination during resist film exposure; $R^{2'}$ is the same as $R^2$ defined in the description of the above formula (1), provided that at least one $R^{2'}$ is a monovalent group containing an iodine atom; and m is an integer of 1 to 6.

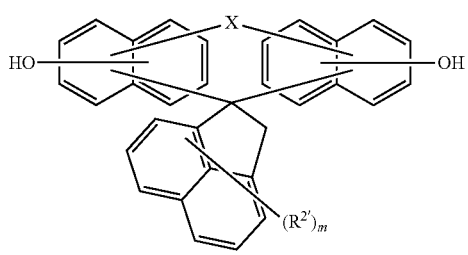

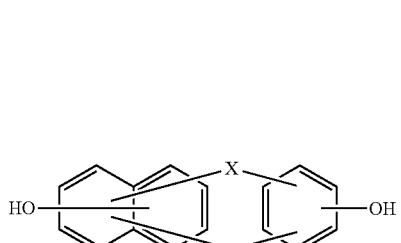

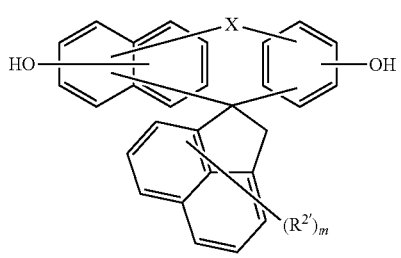

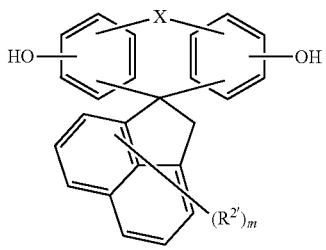

In the above formulae, X is as defined in the description of the above formula (1) and is preferably an oxygen atom from the viewpoint of the suppression of device contamination during resist film exposure; $R^{2'}$ is the same as $R^2$ defined in the description of the above formula (1), provided that at least one $R^{2'}$ is a monovalent group containing an iodine atom; and m is an integer of 1 to 8.

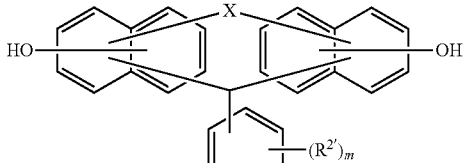

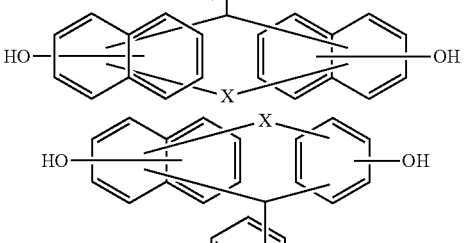

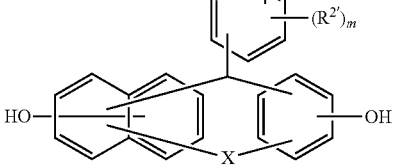

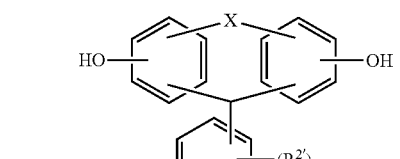

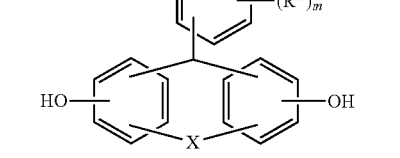

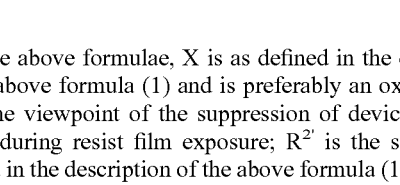

In the above formulae, X is as defined in the description of the above formula (1) and is preferably an oxygen atom from the viewpoint of the suppression of device contamination during resist film exposure; $R^{2'}$ is the same as $R^2$ defined in the description of the above formula (1), provided that at least one $R^{2'}$ is a monovalent group containing an iodine atom; and m is an integer of 1 to 4.

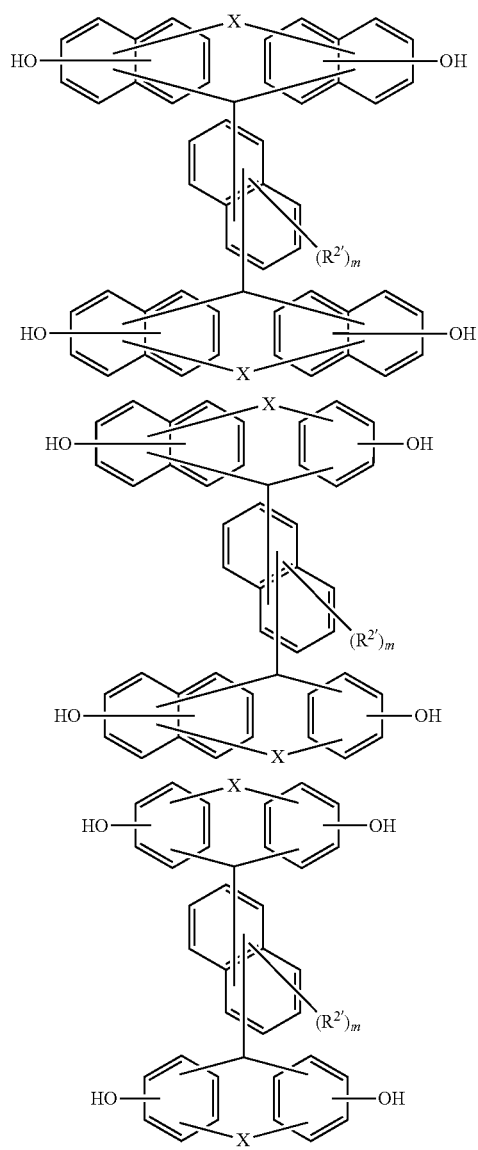

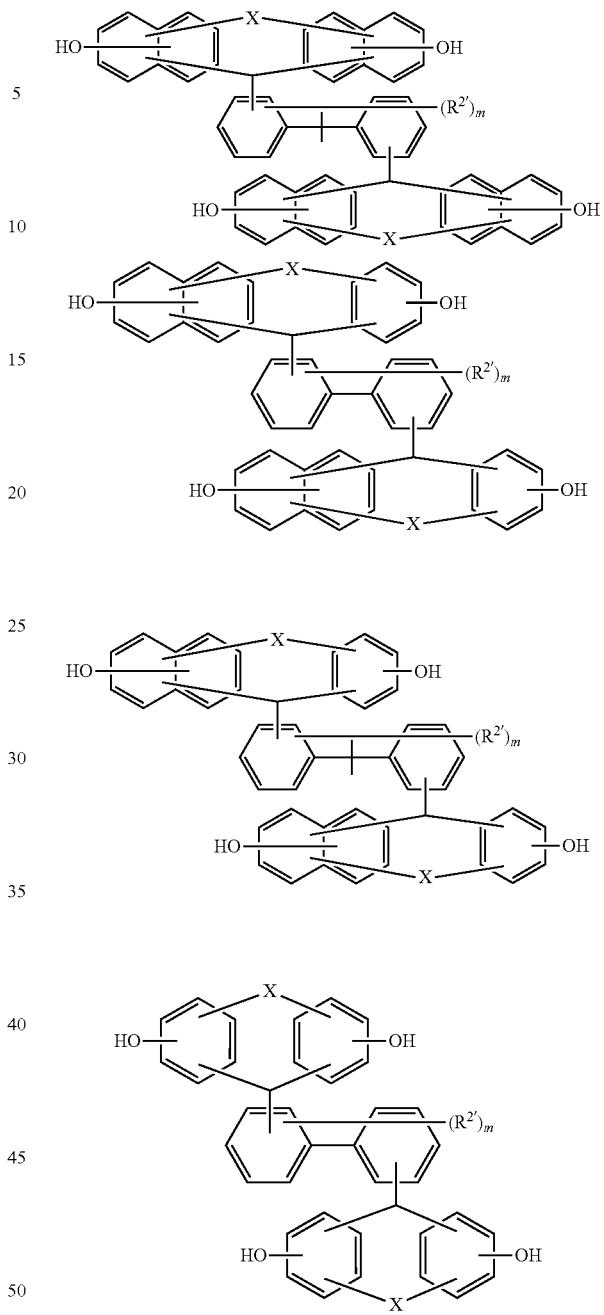

In the above formulae, X is as defined in the description of the above formula (1) and is preferably an oxygen atom from the viewpoint of the suppression of device contamination during resist film exposure; $R^{2'}$ is the same as $R^2$ defined in the description of the above formula (1), provided that at least one $R^{2'}$ is a monovalent group containing an iodine atom; and m is an integer of 1 to 6.

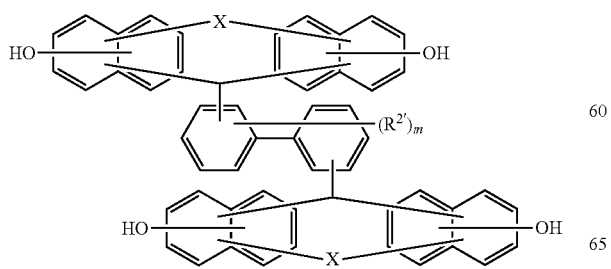

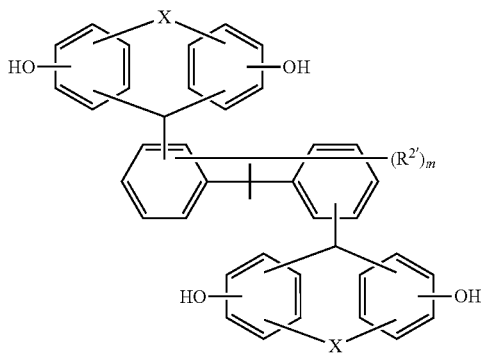

-continued

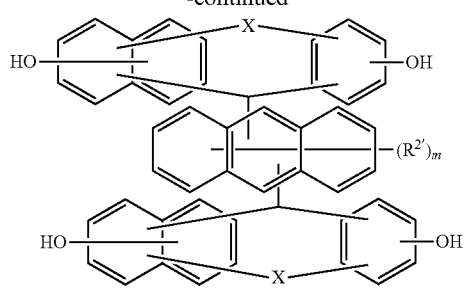

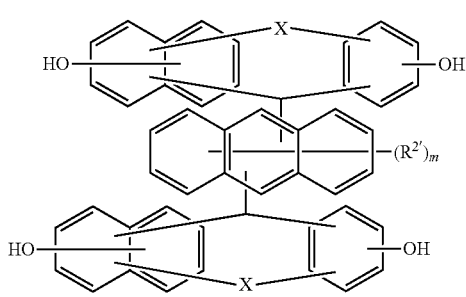

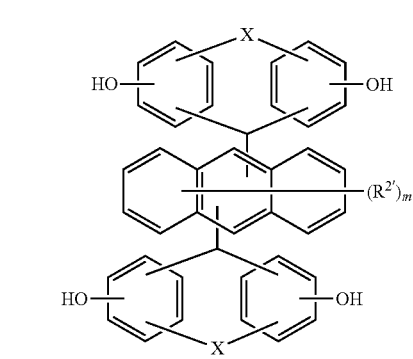

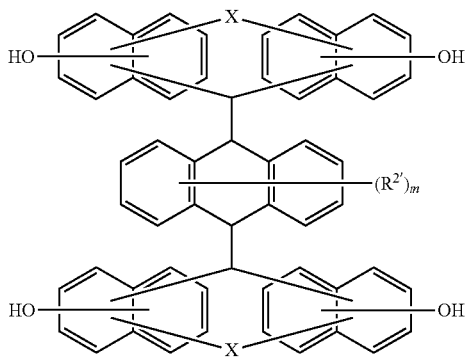

-continued

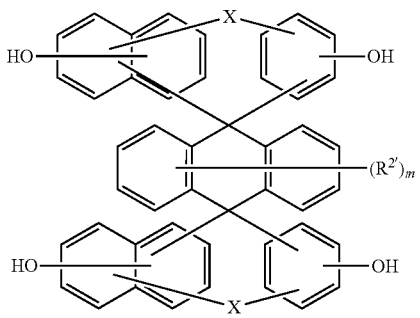

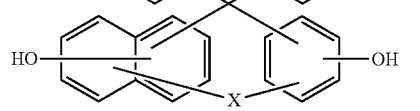

In the above formulae, X is as defined in the description of the above formula (1) and is preferably an oxygen atom from the viewpoint of the suppression of device contamination during resist film exposure; $R^{2'}$ is the same as $R^2$ defined in the description of the above formula (1), provided that at least one $R^{2'}$ is a monovalent group containing an iodine atom; and m is an integer of 1 to 10.

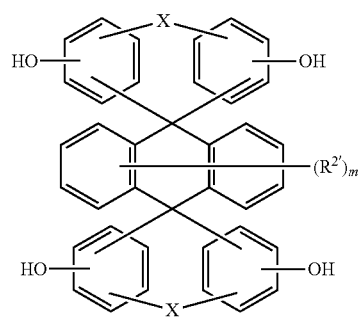

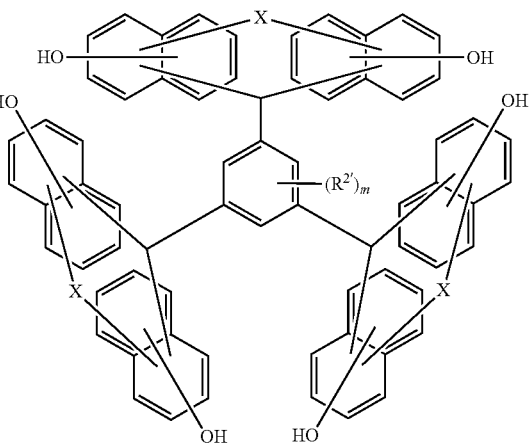

In the above formulae, X is as defined in the description of the above formula (1) and is preferably an oxygen atom from the viewpoint of the suppression of device contamination during resist film exposure; $R^{2'}$ is the same as $R^2$ defined in the description of the above formula (1), provided that at least one $R^{2'}$ is a monovalent group containing an iodine atom; and m is an integer of 1 to 8.

-continued

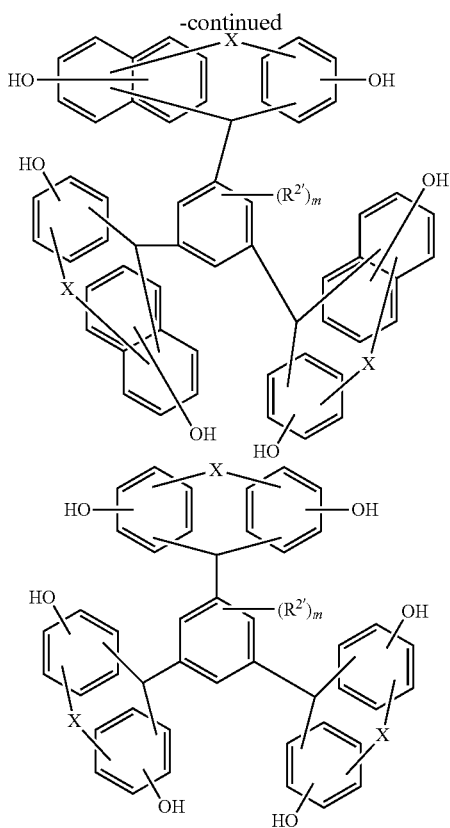

In the above formulae, X is as defined in the description of the above formula (1) and is preferably an oxygen atom from the viewpoint of the suppression of device contamination during resist film exposure; $R^{2'}$ is the same as $R^2$ defined in the description of the above formula (1), provided that at least one $R^{2'}$ is a monovalent group containing an iodine atom; and m is an integer of 1 to 3.

[Method for Producing Compound]

The compound represented by the formula (1) of the present embodiment can be arbitrarily synthesized by applying a publicly known approach, and the synthesis approach is not particularly limited except that at least one selected from the group consisting of $R^1$, $R^2$, and $R^3$ is a group containing an iodine atom. The compound represented by the above formula (1) can be obtained, for example, by subjecting a phenol, a thiophenol, a naphthol, or a thionaphthol, and a corresponding aldehyde compound (A) or ketone having a monovalent group containing an iodine atom, to polycondensation reaction in the presence of an acid catalyst at normal pressure. If necessary, this reaction can also be carried out under increased pressure.

Examples of the phenol include, but not particularly limited to, phenol, methylphenol, methoxybenzene, catechol, resorcinol, hydroquinone, and trimethylhydroquinone. These phenols may be used alone as one kind or may be used in combination of two or more kinds. Among them, hydroquinone and trimethylhydroquinone are more preferably used in terms of enabling a xanthene structure to be easily formed.

Examples of the thiophenol include, but not particularly limited to, benzenethiol, methylbenzenethiol, methoxybenzenethiol, benzenedithiol, and trimethylbenzenedithiol. These thiophenols may be used alone as one kind or may be used in combination of two or more kinds. Among them, benzenedithiol and trimethylbenzenedithiol are more suitably used in terms of enabling a thioxanthene structure to be easily formed.

Examples of the naphthol include, but not particularly limited to, naphthol, methylnaphthol, methoxynaphthol, and naphthalenediol. These naphthols may be used alone as one kind or may be used in combination of two or more kinds. Among them, naphthalenediol is more preferably used in terms of enabling a benzoxanthene structure to be easily formed.

Examples of the thionaphthol include, but not particularly limited to, naphthalenethiol, methylnaphthalenethiol, methoxynaphthalenethiol, and naphthalenedithiol. These thionaphthols may be used alone as one kind or may be used in combination of two or more kinds. Among them, naphthalenedithiol is more suitably used in terms of enabling a thiobenzoxanthene structure to be easily formed.

A compound suitable as the aldehyde compound (A) is a compound of 2 to 59 carbon atoms having 1 to 4 formyl groups and a monovalent group containing an iodine atom.

The suitable aldehyde compound (A) has 2 to 59 carbon atoms, has 1 to 4 formyl groups and a monovalent group containing an iodine atom, and is selected from an aromatic aldehyde compound (A1) and an aliphatic aldehyde compound (A2).

The aromatic aldehyde compound (A1) is preferably a benzaldehyde compound of 7 to 24 carbon atoms, and examples include, but not particularly limited to, iodobenzaldehyde, methyliodobenzaldehyde, dimethyliodobenzaldehyde, ethyliodobenzaldehyde, propyliodobenzaldehyde, butyliodobenzaldehyde, ethylmethyliodobenzaldehyde, isopropylmethyliodobenzaldehyde, diethyliodobenzaldehyde, methoxyiodoaldehyde, iodonaphthaldehyde, iodoanthraldehyde, cyclopropyliodobenzaldehyde, cyclobutyliodobenzaldehyde, cyclopentyliodobenzaldehyde, cyclohexyliodobenzaldehyde, phenyliodobenzaldehyde, naphthyliodobenzaldehyde, adamantyliodobenzaldehyde, norbornyliodobenzaldehyde, lactyliodobenzaldehyde, isopropyliodobenzaldehyde, normalpropyliodobenzaldehyde, bromoiodobenzaldehyde, dimethylaminoiodobenzaldehyde, hydroxyiodobenzaldehyde, dihydroxyiodobenzaldehyde, and trihydroxyiodobenzaldehyde. Iodobenzaldehyde, methyliodobenzaldehyde, dimethyliodobenzaldehyde, and ethyliodobenzaldehyde are more preferable, and iodobenzaldehyde is still more preferable.

The aromatic aldehyde compound (A1) may have a linear or branched alkyl group of 1 to 4 carbon atoms, a cyano group, a hydroxy group, a halogen, or the like, as long as the effects of the present invention are not impaired. The aromatic aldehyde compound (A1) may be used alone or in combination of two or more kinds.

The aliphatic aldehyde compound (A2) is preferably a compound of 3 to 24 carbon atoms, and examples include, but not particularly limited to, iodopropanal, iodoisopropanal, iodobutanal, iodoisobutanal, iodo-t-butanal, iodopentanal, iodoisopentanal, iodoneopentanal, iodohexanal, iodoisohexanal, iodooctanal, iododecanal, iodododecanal, iodoundecenal, iodocyclopropanecarboxyaldehyde, iodocyclobutanecarboxyaldehyde, and iodocyclohexanecarboxyaldehyde. Iodoisobutanal, iodo-t-butanal, iodopentanal, iodoisopentanal, iodoneopentanal, iodohexanal, iodoisohexanal, iodooctanal, iododecanal, iodododecanal, iodocyclopropanecarboxyaldehyde, iodocyclobutanecarboxyaldehyde, and iodocyclohexanecarboxyaldehyde are more preferable, and iodooctanal, iododecanal, iodododecanal, and iodocyclohexanecarboxyaldehyde are still more preferable.

The aliphatic aldehyde compound (A2) may have a cyano group, a hydroxy group, a halogen, or the like, as long as the effects of the present invention are not impaired. The aliphatic aldehyde compound (A2) may be used alone or in combination of two or more kinds.

Examples of the ketone include, but not limited to, acetone, methyl ethyl ketone, cyclobutanone, cyclopentanone, cyclohexanone, norbornanone, tricyclohexanone, tricyclodecanone, adamantanone, fluorenone, benzofluorenone, acenaphthenequinone, acenaphthenone, and anthraquinone. These ketones may be used alone as one kind or may be used in combination of two or more kinds. Among them, cyclopentanone, cyclohexanone, norbornanone, tricyclohexanone, tricyclodecanone, adamantanone, fluorenone, benzofluorenone, acenaphthenequinone, acenaphthenone, or anthraquinone is preferably used in terms of providing high heat resistance.

The acid catalyst used in the above reaction can be arbitrarily selected and used from publicly known catalysts and is not particularly limited. Inorganic acids and organic acids are widely known as such acid catalysts, and examples include, but not particularly limited to, inorganic acids such as hydrochloric acid, sulfuric acid, phosphoric acid, hydrobromic acid, and hydrofluoric acid; organic acids such as oxalic acid, malonic acid, succinic acid, adipic acid, sebacic acid, citric acid, fumaric acid, maleic acid, formic acid, p-toluenesulfonic acid, methanesulfonic acid, trifluoroacetic acid, dichloroacetic acid, trichloroacetic acid, trifluoromethanesulfonic acid, benzenesulfonic acid, naphthalenesulfonic acid, and naphthalenedisulfonic acid; Lewis acids such as zinc chloride, aluminum chloride, iron chloride, and boron trifluoride; and solid acids such as tungstosilicic acid, tungstophosphoric acid, silicomolybdic acid, and phosphomolybdic acid. Among them, organic acids and solid acids are preferable from the viewpoint of production, and hydrochloric acid or sulfuric acid is preferably used from the viewpoint of production such as easy availability and handleability. The acid catalysts can be used alone as one kind, or can be used in combination of two or more kinds. Also, the amount of the acid catalyst used can be arbitrarily set according to, for example, the kind of the raw materials used and the catalyst used and moreover the reaction conditions and is not particularly limited, but is preferably 0.01 to 100 parts by mass based on 100 parts by mass of the reaction raw materials.

Upon the above reaction, a reaction solvent may be used. The reaction solvent is not particularly limited as long as the reaction of the aldehyde compound (A) or the ketone used with the phenol, the thiophenol, the naphthol, or the thionaphthol proceeds, and can be arbitrarily selected and used from those publicly known, and examples include water, methanol, ethanol, propanol, butanol, tetrahydrofuran, dioxane, ethylene glycol dimethyl ether, ethylene glycol diethyl ether, and a mixed solvent thereof. The solvent can be used alone, or in combination of two or more kinds. Also, the amount of these solvents used can be arbitrarily set according to, for example, the kind of the raw materials used and the catalyst used and moreover the reaction conditions and is not particularly limited, but is preferably in the range of 0 to 2000 parts by mass based on 100 parts by mass of the reaction raw materials. Moreover, the reaction temperature in the above reaction can be arbitrarily selected according to the reactivity of the reaction raw materials and is not particularly limited, but is usually within the range of 10 to 200° C.

In order to obtain the compound represented by the general formula (1) of the present embodiment, a higher reaction temperature is more preferable. Specifically, the range of 60 to 200° C. is preferable. The reaction method can be arbitrarily selected and used from publicly known approaches and is not particularly limited, and there are a method of charging the phenol, the thiophenol, the naphthol, or the thionaphthol, the aldehyde compound (A) or the ketone, and the catalyst in one portion, and a method of dropping the phenol, the thiophenol, the naphthol, or the thionaphthol, and the aldehyde compound (A) or the ketone, in the presence of the catalyst. After the polycondensation reaction terminates, isolation of the obtained compound can be carried out according to a conventional method, and is not particularly limited. For example, by adopting a commonly used approach in which the temperature of the reaction vessel is elevated to 130 to 230° C. in order to remove unreacted raw materials, catalyst, etc. present in the system, and volatile portions are removed at about 1 to 50 mmHg, the target compound can be obtained.

As preferable reaction conditions, the reaction proceeds by using 1 mol to an excess of the phenol, the thiophenol, the naphthol, or the thionaphthol and 0.001 to 1 mol of the acid catalyst based on 1 mol of the aldehyde compound (A) or the ketone, and reacting them at 50 to 150° C. at normal pressure for about 20 minutes to 100 hours.

The target component can be isolated by a publicly known method after the reaction terminates. An exemplary method involves concentrating the reaction solution, precipitating the reaction product by the addition of pure water, cooling the reaction solution to room temperature, then separating the precipitates by filtration, filtering and drying the obtained solid matter, then separating and purifying the solid matter from by-products by column chromatography, and distilling off the solvent, followed by filtration and drying, and thus the compound represented by the above general formula (1), which is the target compound, can be obtained.

[Resin]

The resin of the present embodiment is a resin obtained using the compound represented by the above formula (1) as a monomer. Specific examples of the resin include resins having a structure represented by the following general formula (Z).

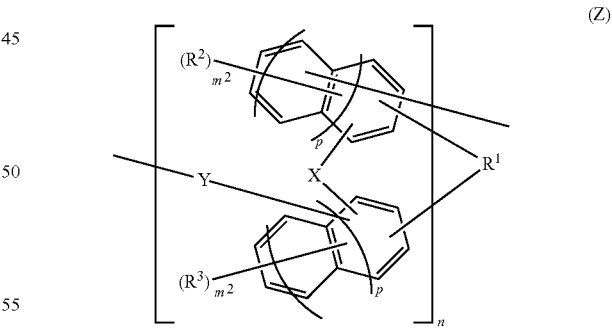

In the above formula (Z), each X is independently an oxygen atom, a sulfur atom, or not a crosslink, and each aromatic ring is bonded to any position via this X. $R^1$ is a single bond or a 2n-valent group of 1 to 30 carbon atoms, and each aromatic ring is bonded via this $R^1$ to any position. Herein, the 2n-valent group may have an alicyclic hydrocarbon group, a double bond, a hetero atom, or an aromatic group of 6 to 30 carbon atoms. $R^2$ and $R^3$ are each independently a monovalent substituent selected from the group consisting of a halogen atom, a linear, branched, or cyclic alkyl group of 1 to 10 carbon atoms, an aryl group of 6 to 10 carbon atoms, an alkenyl group of 2 to 10 carbon atoms, an alkoxy group of 1 to 30 carbon atoms, a thiol group, and a hydroxy group, and $m^2R^2$ and $m^2R^3$ are bonded to any positions of the aromatic rings. Herein, at least one selected from the group consisting of $R^1$, $R^2$, and $R^3$ is a group containing an iodine atom, and at least one $R^2$ and/or at least one $R^3$ is one or more selected from a hydroxy group and a thiol group. Each Y is independently a single bond or a linear or branched alkylene group of 1 to 20 carbon atoms. Also, each $m^2$ is independently an integer of 0 to 6, provided that at least one $m^2$ is an integer of 1 to 6, n is an integer of 1 to 4, and each p is independently 0 or 1. $R^1$ is preferably a 2n-valent hydrocarbon group. The 2n-valent hydrocarbon group is as defined in the description of the above formula (1).

[Method for Producing Resin]

The resin having the structure represented by the above formula (Z) of the present embodiment is obtained by, for example, reacting the compound represented by the above formula (1) with a crosslinking compound (monomer).

As the crosslinking monomer, a publicly known monomer can be used without particular limitations as long as it can oligomerize or polymerize the compound represented by the above formula (1). Specific example thereof include, but not particularly limited to, aldehydes, ketones, carboxylic acids, carboxylic acid halides, halogen-containing compounds, amino compounds, imino compounds, isocyanates, and unsaturated hydrocarbon group-containing compounds.

Specific examples of the resin having the structure represented by the above formula (Z) include, but not particularly limited to, resins that are made novolac by, for example, a condensation reaction between the compound represented by the above formula (1) with an aldehyde that is a crosslinking monomer.

Herein, examples of the aldehyde used when making the compound represented by the above formula (1) novolac include, but not particularly limited to, formaldehyde, trioxane, paraformaldehyde, benzaldehyde, acetaldehyde, propylaldehyde, phenylacetaldehyde, phenylpropylaldehyde, hydroxybenzaldehyde, chlorobenzaldehyde, nitrobenzaldehyde, methylbenzaldehyde, ethylbenzaldehyde, butylbenzaldehyde, biphenylaldehyde, naphthaldehyde, anthracenecarboaldehyde, phenanthrenecarboaldehyde, pyrenecarboaldehyde, and furfural. Among these, formaldehyde is more preferable. These aldehydes can be used alone as one kind or may be used in combination of two or more kinds. The amount of the above aldehydes used is not particularly limited, but is preferably 0.2 to 5 mol and more preferably 0.5 to 2 mol based on 1 mol of the compound represented by the above formula (1).

A catalyst can also be used in the condensation reaction between the compound represented by the above formula (1) and the aldehyde. The acid catalyst used herein can be arbitrarily selected and used from publicly known catalysts and is not particularly limited. Inorganic acids and organic acids are widely known as such acid catalysts, and examples include, but not particularly limited to, inorganic acids such as hydrochloric acid, sulfuric acid, phosphoric acid, hydrobromic acid, and hydrofluoric acid; organic acids such as oxalic acid, malonic acid, succinic acid, adipic acid, sebacic acid, citric acid, fumaric acid, maleic acid, formic acid, p-toluenesulfonic acid, methanesulfonic acid, trifluoroacetic acid, dichloroacetic acid, trichloroacetic acid, trifluoromethanesulfonic acid, benzenesulfonic acid, naphthalenesulfonic acid, and naphthalenedisulfonic acid; Lewis acids such as zinc chloride, aluminum chloride, iron chloride, and boron trifluoride; and solid acids such as tungstosilicic acid, tungstophosphoric acid, silicomolybdic acid, and phosphomolybdic acid. Among them, organic acids and solid acids are preferable from the viewpoint of production, and hydrochloric acid or sulfuric acid is preferable from the viewpoint of production such as easy availability and handleability. The acid catalysts can be used alone as one kind, or can be used in combination of two or more kinds. Also, the amount of the acid catalyst used can be arbitrarily set according to, for example, the kind of the raw materials used and the catalyst used and moreover the reaction conditions and is not particularly limited, but is preferably 0.01 to 100 parts by mass based on 100 parts by mass of the reaction raw materials. The aldehyde is not necessarily needed in the case of a copolymerization reaction with a compound having a non-conjugated double bond, such as indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, 5-vinylnorborn-2-ene, α-pinene, β-pinene, and limonene.

A reaction solvent can also be used in the condensation reaction between the compound represented by the above formula (1) and the aldehyde. The reaction solvent in the polycondensation can be arbitrarily selected and used from publicly known solvents and is not particularly limited, and examples include water, methanol, ethanol, propanol, butanol, tetrahydrofuran, dioxane, or a mixed solvent thereof. The solvents can be used alone as one kind, or can be used in combination of two or more kinds. Also, the amount of these solvents used can be arbitrarily set according to, for example, the kind of the raw materials used and the catalyst used and moreover the reaction conditions and is not particularly limited, but is preferably in the range of 0 to 2000 parts by mass based on 100 parts by mass of the reaction raw materials. Furthermore, the reaction temperature can be arbitrarily selected according to the reactivity of the reaction raw materials and is not particularly limited, but is usually within the range of 10 to 200° C. The reaction method can be arbitrarily selected and used from publicly known approaches and is not particularly limited, and there are a method of charging the compound represented by the above general formula (1), the aldehyde, and the catalyst in one portion, and a method of dropping the compound represented by the above general formula (1) and the aldehyde in the presence of the catalyst. After the polycondensation reaction terminates, isolation of the obtained compound can be carried out according to a conventional method, and is not particularly limited. For example, by adopting a commonly used approach in which the temperature of the reaction vessel is elevated to 130 to 230° C. in order to remove unreacted raw materials, catalyst, etc. present in the system, and volatile portions are removed at about 1 to 50 mmHg, a novolac resin that is the target compound can be obtained.

Herein, the resin having the structure represented by the above formula (Z) may be a homopolymer of a compound represented by the above formula (1), or may be a copolymer with a further phenol. Herein, examples of the copolymerizable phenol include, but not particularly limited to, phenol, cresol, dimethylphenol, trimethylphenol, butylphenol, phenylphenol, diphenylphenol, naphthylphenol, resorcinol, methylresorcinol, catechol, butylcatechol, methoxyphenol, methoxyphenol, propylphenol, pyrogallol, and thymol.

The resin having the structure represented by the above formula (Z) may be a copolymer with a polymerizable monomer other than the above-described further phenols. Examples of such a copolymerization monomer include, but not particularly limited to, naphthol, methylnaphthol, methoxynaphthol, dihydroxynaphthalene, indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, vinylnorbornene, pinene, and limonene. The resin having the structure represented by the above formula (Z) may be a copolymer of two or more components (for example, a binary to quaternary system) composed of the compound represented by the above general formula (1) and the above-described phenol, may be a copolymer of two or more components (for example, a binary to quaternary system) composed of the compound represented by the above general formula (1) and the above-described copolymerization monomer, or may be a copolymer of three or more components (for example, a tertiary to quaternary system) composed of the compound represented by the above general formula (1), the above-described phenol, and the above-described copolymerization monomer.

[Method for Purifying Compound or Resin]

The method for purifying the compound or the resin of the present embodiment comprises the steps of:

obtaining a solution (A) by dissolving the compound represented by the above general formula (1) or the resin having the structure represented by the above general formula (Z) in a solvent; and extracting impurities in the compound or the resin by bringing the obtained solution (A) into contact with an acidic aqueous solution (a first extraction step), wherein the solvent used in the step of obtaining the solution (A) contains an organic solvent that does not inadvertently mix with water.

In the first extraction step, the resin having the structure represented by the above general formula (Z) is preferably a resin obtained by a reaction between the compound represented by the above formula (1) and a crosslinking compound.

Because the purification method of the present embodiment is configured as described above, according to the purification method, the contents of various metals that may be contained as impurities in the compound or the resin having a specific structure described above can be reduced.

More specifically, in the purification method of the present embodiment, the above compound or resin is dissolved in an organic solvent that does not inadvertently mix with water to obtain the solution (A), and further, extraction treatment can be carried out by bringing the solution (A) into contact with an acidic aqueous solution. Thereby, metals contained in the solution (A) containing the compound represented by the above formula (1) or the resin having the structure represented by the above general formula (Z) (for example, a resin obtained by a reaction between the compound represented by the above formula (1) and a crosslinking compound) are transferred to the aqueous phase, then the organic phase and the aqueous phase are separated, and thus the compound represented by the above formula (1) or the resin having the structure represented by the above general formula (Z) (for example, a resin obtained by a reaction between the compound represented by the above formula (1) and a crosslinking compound) having a reduced metal content can be obtained.

The compound represented by the above formula (1) or the resin having the structure represented by the above general formula (Z) (for example, a resin obtained by a reaction between the compound represented by the above formula (1) and a crosslinking compound) used in the purification method of the present embodiment may be alone, or may be a mixture of two or more kinds. Also, the compound represented by the above formula (1) or the resin having the structure represented by the above general formula (Z) (for example, a resin obtained by a reaction between the compound represented by the above formula (1) and a crosslinking compound) may contain various surfactants, various crosslinking agents, various acid generators, various stabilizers, and the like.

The organic solvent that does not inadvertently mix with water used in the purification method of the present embodiment is not particularly limited, but is preferably an organic solvent that is safely applicable to semiconductor manufacturing processes, and specifically it is an organic solvent having a solubility in water at room temperature of less than 30%, and more preferably is an organic solvent having a solubility of less than 20% and particularly preferably less than 10%. The amount of the organic solvent used is preferably 1 to 100 times the mass of the compound represented by the above formula (1) or the resin having the structure represented by the above general formula (Z) (for example, a resin obtained by a reaction between the compound represented by the above formula (1) and a crosslinking compound).

Specific examples of the organic solvent that does not inadvertently mix with water include, but not limited to, ethers such as diethyl ether and diisopropyl ether; esters such as ethyl acetate, n-butyl acetate, and isoamyl acetate; ketones such as methyl ethyl ketone, methyl isobutyl ketone, ethyl isobutyl ketone, cyclohexanone (CHN), cyclopentanone, 2-heptanone, and 2-pentanone; glycol ether acetates such as ethylene glycol monoethyl ether acetate, ethylene glycol monobutyl ether acetate, propylene glycol monomethyl ether acetate (PGMEA), and propylene glycol monoethyl ether acetate; aliphatic hydrocarbons such as n-hexane and n-heptane; aromatic hydrocarbons such as toluene and xylene; and halogenated hydrocarbons such as methylene chloride and chloroform. Among these, toluene, 2-heptanone, cyclohexanone, cyclopentanone, methyl isobutyl ketone, propylene glycol monomethyl ether acetate, ethyl acetate, and the like are preferable, methyl isobutyl ketone, ethyl acetate, cyclohexanone, and propylene glycol monomethyl ether acetate are more preferable, and methyl isobutyl ketone and ethyl acetate are still more preferable. Methyl isobutyl ketone, ethyl acetate, and the like have relatively high saturation solubility for the compound represented by the above formula (1) or the resin having the structure represented by the above general formula (Z) (for example, a resin obtained by a reaction between the compound represented by the above formula (1) and a crosslinking compound) and a relatively low boiling point, and it is thus possible to reduce the load in the case of industrially distilling off the solvent and in the step of removing the solvent by drying.

These organic solvents can be each used alone, and can be used as a mixture of two or more kinds.

The acidic aqueous solution used in the purification method of the present embodiment is arbitrarily selected from aqueous solutions in which generally known organic compounds or inorganic compounds are dissolved in water. Examples include, but not limited to, aqueous mineral acid solutions in which mineral acids such as hydrochloric acid, sulfuric acid, nitric acid, and phosphoric acid are dissolved in water; and aqueous organic acid solutions in which organic acids such as acetic acid, propionic acid, oxalic acid, malonic acid, succinic acid, fumaric acid, maleic acid, tartaric acid, citric acid, methanesulfonic acid, phenolsulfonic acid, p-toluenesulfonic acid, and trifluoroacetic acid are dissolved in water. These acidic aqueous solutions can be each used alone, and can be also used as a combination of two or more kinds. Among these acidic aqueous solutions, aqueous solutions of one or more mineral acids selected from the group consisting of hydrochloric acid, sulfuric acid, nitric acid, and phosphoric acid, or aqueous solutions of one or more organic acids selected from the group consisting of acetic acid, propionic acid, oxalic acid, malonic acid, succinic acid, fumaric acid, maleic acid, tartaric acid, citric acid, methanesulfonic acid, phenolsulfonic acid, p-toluenesulfonic acid, and trifluoroacetic acid are preferable, aqueous solutions of sulfuric acid, nitric acid, and carboxylic acids such as acetic acid, oxalic acid, tartaric acid, and citric acid are more preferable, aqueous solutions of sulfuric acid, oxalic acid, tartaric acid, and citric acid are still more preferable, and an aqueous solution of oxalic acid is further preferable. It is considered that polyvalent carboxylic acids such as oxalic acid, tartaric acid, and citric acid coordinate with metal ions and provide a chelating effect, and thus tend to be capable of more effectively removing metals. As for water used herein, it is preferable to use water, the metal content of which is small, such as ion exchanged water, according to the purpose of the purification method of the present embodiment.

The pH of the acidic aqueous solution used in the purification method of the present embodiment is not particularly limited, but it is preferable to regulate the acidity of the aqueous solution in consideration of an influence on the compound represented by the above formula (1) or the resin having the structure represented by the above general formula (Z) (for example, a resin obtained by a reaction between the compound represented by the above formula (1) and a crosslinking compound). Normally, the pH range is about 0 to 5, and is preferably about pH 0 to 3.

The amount of the acidic aqueous solution used in the purification method of the present embodiment is not particularly limited, but it is preferable to regulate the amount from the viewpoint of reducing the number of extraction operations for removing metals and from the viewpoint of ensuring operability in consideration of the overall amount of fluid. From the above viewpoints, the amount of the acidic aqueous solution used is preferably 10 to 200% by mass, more preferably 20 to 100% by mass, based on 100% by mass of the solution (A).

In the purification method of the present embodiment, by bringing an acidic aqueous solution as described above into contact with the solution (A) containing the compound represented by the above formula (1) or the resin having the structure represented by the above general formula (Z) (for example, a resin obtained by a reaction between the compound represented by the above formula (1) and a crosslinking compound) and the organic solvent that does not inadvertently mix with water, metals can be extracted from the compound or the resin in the solution (A).

In the purification method of the present embodiment, it is preferable that the solution (A) further contains an organic solvent that advertently mixes with water. When an organic solvent that advertently mixes with water is contained, there is a tendency that the amount of the compound represented by the above formula (1) or the resin having the structure represented by the above general formula (Z) (for example, a resin obtained by a reaction between the compound represented by the above formula (1) and a crosslinking compound) charged can be increased, also the fluid separability is improved, and purification can be carried out at a high efficiency of reaction vessel. The method for adding the organic solvent that advertently mixes with water is not particularly limited. For example, any of a method involving adding it to the organic solvent-containing solution in advance, a method involving adding it to water or the acidic aqueous solution in advance, and a method involving adding it after bringing the organic solvent-containing solution into contact with water or the acidic aqueous solution. Among these, the method involving adding it to the organic solvent-containing solution in advance is preferable in terms of the workability of operations and the ease of managing the amount.

The organic solvent that inadvertently mixes with water used in the purification method of the present embodiment is not particularly limited, but is preferably an organic solvent that is safely applicable to semiconductor manufacturing processes. The amount of the organic solvent used that inadvertently mixes with water is not particularly limited as long as the solution phase and the aqueous phase separate, but is preferably 0.1 to 100 times, more preferably 0.1 to 50 times, and further preferably 0.1 to 20 times the mass of the compound represented by the above formula (1) or the resin having the structure represented by the above general formula (Z) (for example, a resin obtained by a reaction between the compound represented by the above formula (1) and a crosslinking compound).

Specific examples of the organic solvent used in the purification method of the present embodiment that inadvertently mixes with water include, but not limited to, ethers such as tetrahydrofuran and 1,3-dioxolane; alcohols such as methanol, ethanol, and isopropanol; ketones such as acetone and N-methylpyrrolidone; aliphatic hydrocarbons such as glycol ethers such as ethylene glycol monoethyl ether, ethylene glycol monobutyl ether, propylene glycol monomethyl ether (PGME), and propylene glycol monoethyl ether. Among these, N-methylpyrrolidone, propylene glycol monomethyl ether, and the like are preferable, and N-methylpyrrolidone and propylene glycol monomethyl ether are more preferable. These solvents can be each used alone, and can be used as a mixture of two or more kinds.

In the purification method of the present embodiment, the temperature when the solution (A) and the acidic aqueous solution are brought into contact, i.e., when extraction treatment is carried out, is preferably in the range of 20 to 90° C., and more preferably 30 to 80° C. The extraction operation is not particularly limited, and is carried out, for example, by thoroughly mixing the solution (A) and the acidic aqueous solution by stirring or the like and then leaving the obtained mixed solution to stand still. Thereby, metals contained in the solution (A) containing the compound represented by the above formula (1) or the resin having the structure represented by the above general formula (Z) (for example, a resin obtained by a reaction between the compound represented by the above formula (1) and a crosslinking compound) and the organic solvents are transferred to the aqueous phase. Also, by this operation, the acidity of the solution (A) is lowered, and the degradation of the compound represented by the above formula (1) or the resin having the structure represented by the above general formula (Z) (for example, a resin obtained by a reaction between the compound represented by the above formula (1) and a crosslinking compound) can be suppressed.

By being left to stand still, the mixed solution is separated into an aqueous phase and a solution phase containing the compound represented by the above formula (1) or the resin having the structure represented by the above general formula (Z) (for example, a resin obtained by a reaction between the compound represented by the above formula (1) and a crosslinking compound) and the organic solvents, and thus the solution phase containing the compound represented by the above formula (1) or the resin having the structure represented by the above general formula (Z) (for example, a resin obtained by a reaction between the compound represented by the above formula (1) and a crosslinking compound) and the organic solvents is recovered by decantation. The time for leaving the mixed solution to stand still is not particularly limited, but it is preferable to regulate the time for leaving the mixed solution to stand still from the viewpoint of attaining good separation of the solution phase containing the organic solvents and the aqueous phase. Normally, the time for leaving the mixed solution to stand still is 1 minute or longer, preferably 10 minutes or longer, and more preferably 30 minutes or longer. While the extraction treatment may be carried out once, it is effective to repeat mixing, leaving-to-stand-still, and separating operations multiple times.

It is preferable that the purification method of the present embodiment includes the step of extracting impurities in the compound or the resin by further bringing the solution phase containing the compound or the resin into contact with water after the first extraction step (the second extraction step).

Specifically, for example, it is preferable that after the above extraction treatment is carried out using an acidic aqueous solution, the solution phase that is extracted and recovered from the aqueous solution and that contains the compound represented by the above formula (1) or the resin having the structure represented by the above general formula (Z) (for example, a resin obtained by a reaction between the compound represented by the above formula (1) and a crosslinking compound) and the organic solvents is further subjected to extraction treatment with water. The above extraction treatment with water is not particularly limited, and can be carried out, for example, by thoroughly mixing the solution phase and water by stirring or the like and then leaving the obtained mixed solution to stand still. The mixed solution after being left to stand still is separated into an aqueous phase and a solution phase containing the compound represented by the above formula (1) or the resin having the structure represented by the above general formula (Z) (for example, a resin obtained by a reaction between the compound represented by the above formula (1) and a crosslinking compound) and the organic solvents, and thus the solution phase containing the compound represented by the above formula (1) or the resin having the structure represented by the above general formula (Z) (for example, a resin obtained by a reaction between the compound represented by the above formula (1) and a crosslinking compound) and the organic solvents can be recovered by decantation.

Water used herein is preferably water, the metal content of which is small, such as ion exchanged water, according to the purpose of the present embodiment. While the extraction treatment may be carried out once, it is effective to repeat mixing, leaving-to-stand-still, and separating operations multiple times. The proportions of both used in the extraction treatment and temperature, time, and other conditions are not particularly limited, and may be the same as those of the previous contact treatment with the acidic aqueous solution.

Water that is possibly present in the thus-obtained solution containing the compound represented by the above formula (1) or the resin having the structure represented by the above general formula (Z) (for example, a resin obtained by a reaction between the compound represented by the above formula (1) and a crosslinking compound) and the organic solvents can be easily removed by performing vacuum distillation or a like operation. Also, if required, the concentration of the compound represented by the above formula (1) or the resin having the structure represented by the above general formula (Z) (for example, a resin obtained by a reaction between the compound represented by the above formula (1) and a crosslinking compound) can be regulated to be any concentration by adding an organic solvent to the solution.

The method for isolating the compound represented by the above formula (1) or the resin having the structure represented by the above general formula (Z) (for example, a resin obtained by a reaction between the compound represented by the above formula (1) and a crosslinking compound) from the obtained solution containing the compound represented by the above formula (1) or the resin having the structure represented by the above general formula (Z) (for example, a resin obtained by a reaction between the compound represented by the above formula (1) and a crosslinking compound) and the organic solvents is not particularly limited, and publicly known methods can be carried out, such as reduced-pressure removal, separation by reprecipitation, and a combination thereof. Publicly known treatments such as concentration operation, filtration operation, centrifugation operation, and drying operation can be carried out if required.

[Physical Properties and the Like of Resist Composition]

The resist composition of the present embodiment contains the compound represented by the above formula (1) and/or the resin having the structure represented by the above general formula (Z).

The resist composition of the present embodiment can form an amorphous film by spin coating. In this case, the dissolution rate of the amorphous film formed by spin coating with the resist composition of the present embodiment in a developing solution at 23° C. is preferably 10 angstrom/sec or more, more preferably 10 to 10000 angstrom/sec, and still more preferably 100 to 1000 angstrom/sec. When the dissolution rate is 10 angstrom/sec or more, the amorphous film more easily dissolves in a developing solution, and is more suitable for a resist. When the amorphous film has a dissolution rate of 10000 angstrom/sec or less, the resolution may improve. It is presumed that this is because due to the change in the solubility before and after exposure of the compound represented by the above formula (1) or the resin having the structure represented by the above general formula (Z), contrast at the interface between the unexposed portion being dissolved in a developing solution and the exposed portion not being dissolved in a developing solution is increased. Also, there are effects of reducing LER and defects. The dissolution rate can be determined by immersing the amorphous film in a developing solution for a predetermined period of time at 23° C. and then measuring the film thickness before and after immersion by a publicly known method such as visual, ellipsometric, or QCM method.

The dissolution rate of the portion exposed by radiation such as KrF excimer laser, extreme ultraviolet, electron beam or X-ray, of the amorphous film formed by spin coating with the resist composition of the present embodiment, in a developing solution at 23° C. is preferably 5 angstrom/sec or less, more preferably 0.05 to 5 angstrom/sec, and still more preferably 0.0005 to 5 angstrom/sec. When the dissolution rate is 5 angstrom/sec or less, the above portion is insoluble in a developing solution, and thus the amorphous film is more suitable for a resist. When the amorphous film has a dissolution rate of 0.0005 angstrom/sec or more, the resolution may improve. It is presumed that this is because the micro surface portion of the compound represented by the above formula (1) or the resin having the structure represented by the above general formula (Z) dissolves, and LER is reduced. Also, there are effects of reducing defects.

[Other Components of Resist Composition]

The resist composition of the present embodiment contains the compound represented by the above formula (1) or the resin having the structure represented by the above general formula (Z) as a solid component. The resist composition of the present embodiment may contain both the compound represented by the above formula (1) and the resin having the structure represented by the above general formula (Z).

It is preferable that the resist composition of the present embodiment further contains a solvent other than the compound represented by the above formula (1) and the resin having the structure represented by the above general formula (Z).

Examples of the solvent used in the resist composition of the present embodiment can include, but not particularly limited to, ethylene glycol monoalkyl ether acetates such as ethylene glycol monomethyl ether acetate, ethylene glycol monoethyl ether acetate, ethylene glycol mono-n-propyl ether acetate, and ethylene glycol mono-n-butyl ether acetate; ethylene glycol monoalkyl ethers such as ethylene glycol monomethyl ether and ethylene glycol monoethyl ether; propylene glycol monoalkyl ether acetates such as propylene glycol monomethyl ether acetate, propylene glycol monoethyl ether acetate (PGMEA), propylene glycol mono-n-propyl ether acetate, and propylene glycol mono-n-butyl ether acetate; propylene glycol monoalkyl ethers such as propylene glycol monomethyl ether (PGME) and propylene glycol monoethyl ether; ester lactates such as methyl lactate, ethyl lactate, n-propyl lactate, n-butyl lactate, and n-amyl lactate; aliphatic carboxylic acid esters such as methyl acetate, ethyl acetate, n-propyl acetate, n-butyl acetate, n-amyl acetate, n-hexyl acetate, methyl propionate, and ethyl propionate; other esters such as methyl 3-methoxypropionate, ethyl 3-methoxypropionate, methyl 3-ethoxypropionate, ethyl 3-ethoxypropionate, methyl 3-methoxy-2-methylpropionate, 3-methoxybutylacetate, 3-methyl-3-methoxybutylacetate, butyl 3-methoxy-3-methylpropionate, butyl 3-methoxy-3-methylbutyrate, methyl acetoacetate, methyl pyruvate, and ethyl pyruvate; aromatic hydrocarbons such as toluene and xylene; ketones such as methyl ethyl ketone, 2-heptanone, 3-heptanone, 4-heptanone, cyclopentanone, and cyclohexanone (CHN); amides such as N,N-dimethylformamide, N-methylacetamide, N,N-dimethylacetamide, and N-methylpyrrolidone; and lactones such as γ-lactone. These solvents can be used alone or in combination of two or more kinds.

The solvent used in the resist composition of the present embodiment is preferably a safe solvent, more preferably at least one selected from PGMEA, PGME, CHN, CPN, 2-heptanone, anisole, butyl acetate, ethyl propionate, and ethyl lactate, and still more preferably at least one selected from PGMEA, PGME, and CHN.

In the resist composition of the present embodiment, the amount of the solid component and the amount of the solvent are not particularly limited, but preferably the solid component is 1 to 80% by mass and the solvent is 20 to 99% by mass, more preferably the solid component is 1 to 50% by mass and the solvent is 50 to 99% by mass, still more preferably the solid component is 2 to 40% by mass and the solvent is 60 to 98% by mass, and particularly preferably the solid component is 2 to 10% by mass and the solvent is 90 to 98% by mass, based on 100% by mass of the total mass of the amount of the solid component and the solvent.

The resist composition of the present embodiment may contain at least one selected from the group consisting of an acid generating agent (C), an acid crosslinking agent (G), an acid diffusion controlling agent (E), and a further component (F), as other solid components.

In the resist composition of the present embodiment, the content of the compound represented by the above formula (1) and/or the resin having the structure represented by the above formula (Z) is not particularly limited, but is preferably 50 to 99.4% by mass of the total mass of the solid components (summation of the compound represented by the above formula (1), the resin having the structure represented by the above formula (Z), and optionally used solid components such as acid generating agent (C), acid crosslinking agent (G), acid diffusion controlling agent (E), and further component (F), hereinafter the same), more preferably 55 to 90% by mass, still more preferably 60 to 80% by mass, and particularly preferably 60 to 70% by mass. In the case of the above content, resolution is further improved, and line edge roughness (LER) is further decreased.

When both the compound represented by the above formula (1) and the resin having the structure represented by the above formula (Z) are contained, the content refers to the total amount of the compound represented by the above formula (1) and the resin having the structure represented by the above formula (Z).

The resist composition of the present embodiment preferably contains one or more acid generating agents (C) generating an acid directly or indirectly by irradiation of any radiation selected from visible light, ultraviolet, excimer laser, electron beam, extreme ultraviolet (EUV), X-ray, and ion beam.

In this case, in the resist composition of the present embodiment, the content of the acid generating agent (C) is preferably 0.001 to 49% by mass of the total mass of the solid components, more preferably 1 to 40% by mass, still more preferably 3 to 30% by mass, and particularly preferably 10 to 25% by mass. By using the acid generating agent (C) within the above content range, a pattern profile with even higher sensitivity and even lower edge roughness is obtained.

Concerning the resist composition of the present embodiment, the acid generation method is not particularly limited as long as an acid is generated in the system. By using excimer laser instead of ultraviolet such as g-ray and i-ray, finer processing is possible, and also by using electron beam, extreme ultraviolet, X-ray or ion beam as a high energy ray, further finer processing is possible.

The acid generating agent (C) is not particularly limited, and is preferably at least one kind selected from the group consisting of compounds represented by the following formulae (10-1) to (10-8):

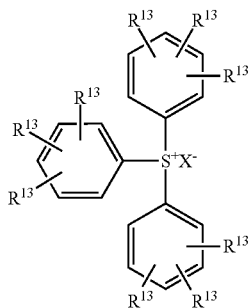

(10-1)

(In the formula (10-1), $R^{13}$ may be the same or different, and are each independently a hydrogen atom, a linear, branched or cyclic alkyl group, a linear, branched or cyclic alkoxy group, a hydroxyl group, or a halogen atom, $X^-$ is an alkyl group, an aryl group, a sulfonic acid ion having a halogen substituted alkyl group or a halogen substituted aryl group, or a halide ion.)

The compound represented by the above formula (10-1) is preferably at least one kind selected from the group consisting of triphenylsulfonium trifluoromethanesulfonate, triphenylsulfonium nonafluoro-n-butanesulfonate, diphenyltolylsulfonium nonafluoro-n-butanesulfonate, triphenylsulfonium perfluoro-n-octanesulfonate, diphenyl-4-methylphenylsulfonium trifluoromethanesulfonate, di-2,4,6-trimethylphenylsulfonium trifluoromethanesulfonate, diphenyl-4-t-butoxyphenylsulfonium trifluoromethanesulfonate, diphenyl-4-t-butoxyphenylsulfonium nonafluoro-n-butanesulfonate, diphenyl-4-hydroxyphenylsulfonium trifluoromethanesulfonate, bis(4-fluorophenyl)-4-hydroxyphenylsulfonium trifluoromethanesulfonate, diphenyl-4-hydroxyphenylsulfonium nonafluoro-n-butanesulfonate, bis(4-hydroxyphenyl)-phenylsulfonium trifluoromethanesulfonate, tri(4-methoxyphenyl)sulfonium trifluoromethanesulfonate, tri(4-fluorophenyl)sulfonium trifluoromethanesulfonate, triphenylsulfonium p-toluenesulfonate, triphenylsulfonium benzenesulfonate, diphenyl-2,4,6-trimethylphenyl-p-toluenesulfonate, diphenyl-2,4,6-trimethylphenylsulfonium-2-trifluoromethylbenzenesulfonate, diphenyl-2,4,6-trimethylphenylsulfonium-4-trifluoromethylbenzenesulfonate, diphenyl-2,4,6-trimethylphenylsulfonium-2,4-difluorobenzenesulfonate, diphenyl-2,4,6-trimethylphenylsulfonium hexafluorobenzenesulfonate, diphenylnaphthylsulfonium trifluoromethanesulfonate, diphenyl-4-hydroxyphenylsulfonium-p-toluenesulfonate, triphenylsulfonium 10-camphorsulfonate, diphenyl-4-hydroxyphenylsulfonium 10-camphorsulfonate, and cyclo(1,3-perfluoropropanedisulfone)imidate.

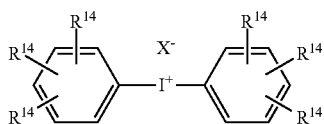

(10-2)

(In the formula (10-2), $R^{14}$ may be the same or different, and each independently represents a hydrogen atom, a linear, branched or cyclic alkyl group, a linear, branched or cyclic alkoxy group, a hydroxyl group, or a halogen atom. $X^-$ is the same as above.)

The compound represented by the above formula (10-2) is preferably at least one kind selected from the group consisting of bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium p-toluenesulfonate, bis(4-t-butylphenyl)iodonium benzenesulfonate, bis(4-t-butylphenyl)iodonium-2-trifluoromethylbenzenesulfonate, bis(4-t-butylphenyl)iodonium-4-trifluoromethylbenzenesulfonate, bis(4-t-butylphenyl)iodonium-2,4-difluorobenzenesulfonate, bis(4-t-butylphenyl)iodonium hexafluorobenzenesulfonate, bis(4-t-butylphenyl)iodonium 10-camphorsulfonate, diphenyliodonium trifluoromethanesulfonate, diphenyliodonium nonafluoro-n-butanesulfonate, diphenyliodonium perfluoro-n-octanesulfonate, diphenyliodonium p-toluenesulfonate, diphenyliodonium benzenesulfonate, diphenyliodonium 10-camphorsulfonate, diphenyliodonium-2-trifluoromethylbenzenesulfonate, diphenyliodonium-4-trifluoromethylbenzenesulfonate, diphenyliodonium-2,4-difluorobenzenesulfonate, diphenyliodonium hexafluorobenzenesulfonate, di(4-trifluoromethylphenyl)iodonium trifluoromethanesulfonate, di(4-trifluoromethylphenyl)iodonium nonafluoro-n-butanesulfonate, di(4-trifluoromethylphenyl)iodonium perfluoro-n-octanesulfonate, di(4-trifluoromethylphenyl)iodonium p-toluenesulfonate, di(4-trifluoromethylphenyl)iodonium benzenesulfonate, and di(4-trifluoromethylphenyl)iodonium 10-camphersulfonate.

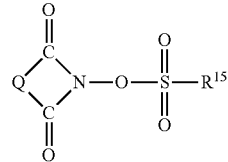

(10-3)

(In the formula (10-3), Q is an alkylene group, an arylene group, or an alkoxylene group, and $R^{15}$ is an alkyl group, an aryl group, a halogen substituted alkyl group, or a halogen substituted aryl group.)

The compound represented by the above formula (10-3) is preferably at least one kind selected from the group consisting of N-(trifluoromethylsulfonyloxy)succinimide, N-(trifluoromethylsulfonyloxy)phthalimide, N-(trifluoromethylsulfonyloxy)diphenylmaleimide, N-(trifluoromethylsulfonyloxy)bicyclo[2.2.1]hept-5-en-2,3-dicarboxyimide, N-(trifluoromethylsulfonyloxy)naphthylimide, N-(10-camphorsulfonyloxy)succinimide, N-(10-camphorsulfonyloxy)phthalimide, N-(10-camphorsulfonyloxy)diphenylmaleimide, N-(10-camphorsulfonyloxy)bicyclo[2.2.1]hept-5-en-2,3-dicarboxyimide, N-(10-camphorsulfonyloxy)naphthylimide, N-(n-octanesulfonyloxy)bicyclo[2.2.1]hept-5-en-2,3-dicarboxyimide, N-(n-octanesulfonyloxy)naphthylimide, N-(p-toluenesulfonyloxy)bicyclo[2.2.1]hept-5-en-2,3-dicarboxyimide, N-(p-toluenesulfonyloxy)naphthylimide, N-(2-trifluoromethylbenzenesulfonyloxy)bicyclo[2.2.1]hept-5-en-2,3-dicarboxyimide, N-(2-trifluoromethylbenzenesulfonyloxy)naphthylimide, N-(4-trifluoromethylbenzenesulfonyloxy)bicyclo[2.2.1]hept-5-en-2,3-dicarboxyimide, N-(4-trifluoromethylbenzenesulfonyloxy)naphthylimide, N-(perfluorobenzenesulfonyloxy)bicyclo[2.2.1]hept-5-en-2,3-dicarboxyimide, N-(perfluorobenzenesulfonyloxy)naphthylimide, N-(1-naphthalenesulfonyloxy)bicyclo[2.2.1]

hept-5-en-2,3-dicarboxyimide, N-(1-naphthalenesulfonyloxy)naphthylimide, N-(nonafluoro-n-butanesulfonyloxy)bicyclo[2.2.1]hept-5-en-2,3-dicarboxyimide, N-(nonafluoro-n-butanesulfonyloxy)naphthylimide, N-(perfluoro-n-octanesulfonyloxy)bicyclo[2.2.1]hept-5-en-2,3-dicarboxyimide, and N-(perfluoro-n-octanesulfonyloxy)naphthylimide.

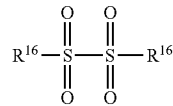

(10-4)

(In the formula (10-4), $R^{16}$ may be the same or different, and are each independently an optionally substituted linear, branched or cyclic alkyl group, an optionally substituted aryl group, an optionally substituted heteroaryl group, or an optionally substituted aralkyl group.)

The compound represented by the above formula (10-4) is preferably at least one kind selected from the group consisting of diphenyldisulfone, di(4-methylphenyl)disulfone, dinaphthyldisulfone, di(4-tert-butylphenyl)disulfone, di(4-hydroxyphenyl)disulfone, di(3-hydroxynaphthyl)disulfone, di(4-fluorophenyl)disulfone, di(2-fluorophenyl)disulfone, and di(4-trifluoromethylphenyl)disulfone.

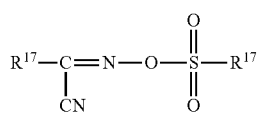

(10-5)

(In the formula (10-5), $R^{17}$ may be the same or different, and are each independently an optionally substituted linear, branched or cyclic alkyl group, an optionally substituted aryl group, an optionally substituted heteroaryl group, or an optionally substituted aralkyl group.)

The compound represented by the above formula (10-5) is preferably at least one kind selected from the group consisting of α-(methylsulfonyloxyimino)-phenylacetonitrile, α-(methylsulfonyloxyimino)-4-methoxyphenylacetonitrile, α-(trifluoromethylsulfonyloxyimino)-phenylacetonitrile, α-(trifluoromethylsulfonyloxyimino)-4-methoxyphenylacetonitrile, α-(ethylsulfonyloxyimino)-4-methoxyphenylacetonitrile, α-(propylsulfonyloxyimino)-4-methylphenylacetonitrile, and α-(methylsulfonyloxyimino)-4-bromophenylacetonitrile.

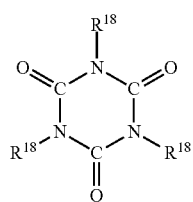

(10-6)

In the formula (10-6), $R^{18}$ may be the same or different, and are each independently a halogenated alkyl group having one or more chlorine atoms and one or more bromine atoms. The number of carbons in the halogenated alkyl group is preferably 1 to 5.

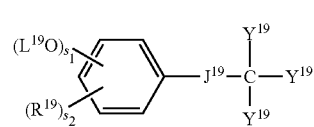

(10-7)

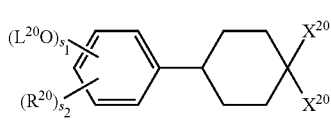

(10-8)

In the formulae (10-7) and (10-8), $R^{19}$ and $R^{20}$ are each independently a C1-3 alkyl group such as a methyl group, an ethyl group, an n-propyl group, and an isopropyl group; a cycloalkyl group such as a cyclopentyl group and a cyclohexyl group; a C1-3 alkoxyl group such as a methoxy group, an ethoxy group, and a propoxy group; or an aryl group such as a phenyl group, a toluoyl group, and a naphthyl group, and preferably a C6-10 aryl group. $L^{19}$ and $L^{20}$ are each independently an organic group having a 1,2-naphthoquinonediazide group. Specifically, preferable examples of the organic group having a 1,2-naphthoquinonediazide group include a 1,2-quinonediazidesulfonyl group such as a 1,2-naphthoquinonediazide-4-sulfonyl group, a 1,2-naphthoquinonediazide-5-sulfonyl group, and a 1,2-naphthoquinonediazide-6-sulfonyl group. Particularly, a 1,2-naphthoquinonediazide-4-sulfonyl group and a 1,2-naphthoquinonediazide-5-sulfonyl group are preferable. $S_1$ is an integer of 1 to 3; $S_2$ is an integer of 0 to 4; and $1 \leq S_1+S_2 \leq 5$. $J^{19}$ is a single bond, a C1-4 polymethylene group, a cycloalkylene group, a phenylene group, a group represented by the following formula (10-7-1), a carbonyl group, an ester group, an amide group, or an ether group. $Y^{19}$ is a hydrogen atom, an alkyl group, or an aryl group, and $X^{20}$ are each independently a group represented by the following formula (10-8-1):

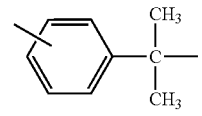

(10-7-1)

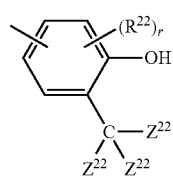

(10-8-1)

(In the above formula (10-8-1), $Z^{22}$ are each independently an alkyl group, a cycloalkyl group, or an aryl group; $R^{22}$ is an alkyl group, a cycloalkyl group, or an alkoxyl group; and r is an integer of 0 to 3.)

Examples of the other acid generating agent include bissulfonyldiazomethanes such as bis(p-toluenesulfonyl)diazomethane, bis(2,4-dimethylphenylsulfonyl)diazomethane, bis(tert-butylsulfonyl)diazomethane, bis(n-butylsulfonyl)diazomethane, bis(isobutylsulfonyl)diazomethane, bis(isopropylsulfonyl)diazomethane, bis(n-propylsulfonyl)diazomethane, bis(cyclohexylsulfonyl)diazomethane, bis(isopropylsulfonyl)diazomethane, 1,3-bis(cyclohexylsulfonylazomethylsulfonyl)propane, 1,4-bis (phenylsulfonylazomethylsulfonyl)butane, 1,6-bis(phenylsulfonylazomethylsulfonyl)hexane, and 1,10-bis(cyclohexylsulfonylazomethylsulfonyl)decane; and halogen-containing triazine derivatives such as 2-(4-methoxyphenyl)-4,6-(bistrichloromethyl)-1,3,5-triazine, 2-(4-methoxynaphthyl)-4,6-(bistrichloromethyl)-1,3,5-triazine, tris(2,3-dibromopropyl)-1,3,5-triazine, and tris(2,3-dibromopropyl)isocyanurate.

Among the acid generating agents, an acid generating agent having an aromatic ring is preferable, and an acid generating agent represented by the formula (10-1) or (10-2) is more preferable. An acid generating agent having a sulfonate ion wherein X⁻ of the formula (10-1) or (10-2) has an aryl group or a halogen-substituted aryl group is more preferable; an acid generating agent having a sulfonate ion wherein X⁻ of the formula (10-1) or (10-2) has an aryl group is particularly preferable; and diphenyltrimethylphenylsulfonium p-toluenesulfonate, triphenylsulfonium p-toluenesulfonate, triphenylsulfonium trifluoromethanesulfonate, and triphenylsulfonium nonafluoromethanesulfonate are particularly preferable. By using the acid generating agent, LER can be reduced.

The acid generating agent (C) can be used alone or in combination of two or more kinds.

The resist composition of the present embodiment preferably contains one or more acid crosslinking agents (G). The acid crosslinking agent (G) is a compound capable of intramolecular or intermolecular crosslinking the compound represented by the formula (1) in the presence of the acid generated from the acid generating agent (C). Examples of such an acid crosslinking agent (G) include, but not particularly limited to, a compound having one or more groups (hereinafter, referred to as "crosslinkable group") capable of crosslinking the compound represented by the formula (1).

Specific examples of such a crosslinkable group are not particularly limited, and examples include (i) a hydroxyalkyl group such as a hydroxy (C1-C6 alkyl group), a C1-C6 alkoxy (C1-C6 alkyl group), and an acetoxy (C1-C6 alkyl group), or a group derived therefrom; (ii) a carbonyl group such as a formyl group and a carboxy (C1-C6 alkyl group), or a group derived therefrom; (iii) a nitrogenous group-containing group such as a dimethylaminomethyl group, a diethylaminomethyl group, a dimethylolaminomethyl group, a diethylolaminomethyl group, and a morpholinomethyl group; (iv) a glycidyl group-containing group such as a glycidyl ether group, a glycidyl ester group, and a glycidylamino group; (v) a group derived from an aromatic group such as a C1-C6 allyloxy (C1-C6 alkyl group) and a C1-C6 aralkyloxy (C1-C6 alkyl group) such as a benzyloxymethyl group and a benzoyloxymethyl group; and (vi) a polymerizable multiple bond-containing group such as a vinyl group and a isopropenyl group. As the crosslinkable group of the acid crosslinking agent (G), a hydroxyalkyl group and an alkoxyalkyl group or the like are preferable, and an alkoxymethyl group is particularly preferable.

Examples of the acid crosslinking agent (G) having the above crosslinkable group include, but not particularly limited to, (i) a methylol group-containing compound such as a methylol group-containing melamine compound, a methylol group-containing benzoguanamine compound, a methylol group-containing urea compound, a methylol group-containing glycoluryl compound, and a methylol group-containing phenolic compound; (ii) an alkoxyalkyl group-containing compound such as an alkoxyalkyl group-containing melamine compound, an alkoxyalkyl group-containing benzoguanamine compound, an alkoxyalkyl group-containing urea compound, an alkoxyalkyl group-containing glycoluryl compound, and an alkoxyalkyl group-containing phenolic compound; (iii) a carboxymethyl group-containing compound such as a carboxymethyl group-containing melamine compound, a carboxymethyl group-containing benzoguanamine compound, a carboxymethyl group-containing urea compound, a carboxymethyl group-containing glycoluryl compound, and a carboxymethyl group-containing phenolic compound; (iv) an epoxy compound such as a bisphenol A based epoxy compound, a bisphenol F based epoxy compound, a bisphenol S based epoxy compound, a novolac resin based epoxy compound, a resol resin based epoxy compound, and a poly(hydroxystyrene) based epoxy compound.

As the acid crosslinking agent (G), a compound having a phenolic hydroxyl group, and a compound and resin where the above crosslinkable group is introduced into an acid functional group in an alkali soluble resin to impart crosslinkability can be further used. The introduction rate of the crosslinkable group in that case is not particularly limited, and is adjusted to be, for example, 5 to 100 mol %, preferably 10 to 60 mol %, and more preferably 15 to 40 mol % based on the total acid functional groups in the compound having a phenolic hydroxy group, and the alkali soluble resin. Within the above range, the crosslinking reaction occurs sufficiently, and a decrease in the film remaining rate, and swelling phenomena and meandering or the like of a pattern are avoided, which is preferable.

In the resist composition of the present embodiment, as the acid crosslinking agent (G), an alkoxyalkylated urea compound or resin thereof, or an alkoxyalkylated glycoluryl compound or resin thereof is preferable. Particularly preferable examples of the acid crosslinking agent (G) include compounds represented by the following formulae (11-1) to (11-3) and an alkoxymethylated melamine compound (acid crosslinking agent (G1)).

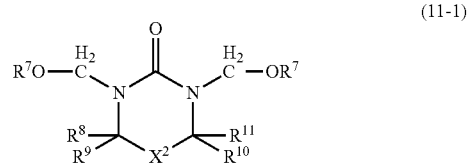

(11-1)

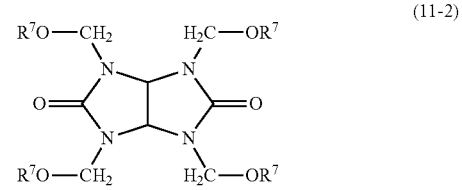

(11-2)

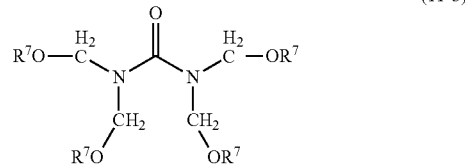

(11-3)

(In the above formulae (11-1) to (11-3), $R^7$ each independently represents a hydrogen atom, an alkyl group, or an acyl group; $R^8$ to $R^{11}$ each independently represents a hydrogen atom, a hydroxyl group, an alkyl group, or an alkoxyl group; and $X^2$ represents a single bond, a methylene group, or an oxygen atom.)

The alkyl group represented by $R^7$ is not particularly limited, and is preferably C1-6, and more preferably C1-3.

Examples thereof include a methyl group, an ethyl group, and a propyl group. The acyl group represented by $R^7$ is not particularly limited, and is preferably C2-6, and more preferably C2-4. Examples thereof include an acetyl group and a propionyl group. The alkyl group represented by $R^8$ to $R^{11}$ is not particularly limited, and is preferably C1-6, and more preferably C1-3. Examples thereof include a methyl group, an ethyl group, and a propyl group. The alkoxy group represented by $R^8$ to $R^{11}$ is not particularly limited, and is preferably C1-6, and more preferably C1-3. Examples thereof include a methoxy group, an ethoxy group, and a propoxy group. $X^2$ is preferably a single bond or a methylene group. $R^7$ to $R^{11}$ and $X^2$ may be substituted with an alkyl group such as a methyl group and an ethyl group, an alkoxy group such as a methoxy group and an ethoxy group, a hydroxyl group, and a halogen atom or the like. A plurality of $R^7$ and $R^8$ to $R^{11}$ may be each the same or different.

Specific examples of the compound represented by the formula (11-1) include compounds represented below.

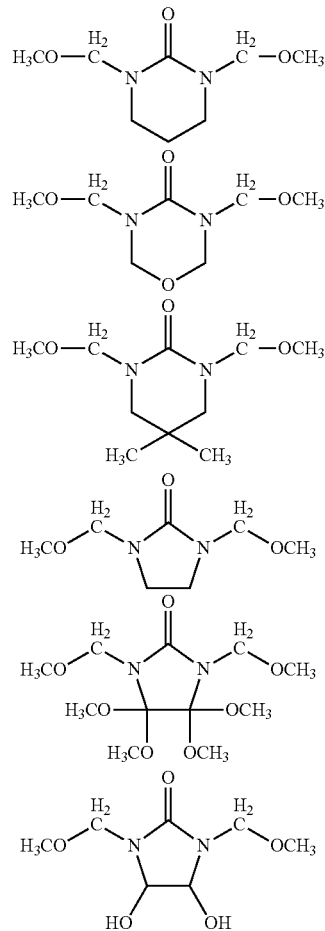

The compound represented by the formula (11-2) is not particularly limited, and specific examples include N,N,N,N-tetra(methoxymethyl)glycoluryl, N,N,N,N-tetra(ethoxymethyl)glycoluryl, N,N,N,N-tetra(n-propoxymethyl)glycoluryl, N,N,N,N-tetra(isopropoxymethyl)glycoluryl, N,N,N,N-tetra(n-butoxymethyl)glycoluryl, and N,N,N,N-tetra(t-butoxymethyl)glycoluryl. Among these, N,N,N,N-tetra(methoxymethyl)glycoluryl is particularly preferable.

The compound represented by the formula (11-3) is not particularly limited, and specific examples include compounds represented below.

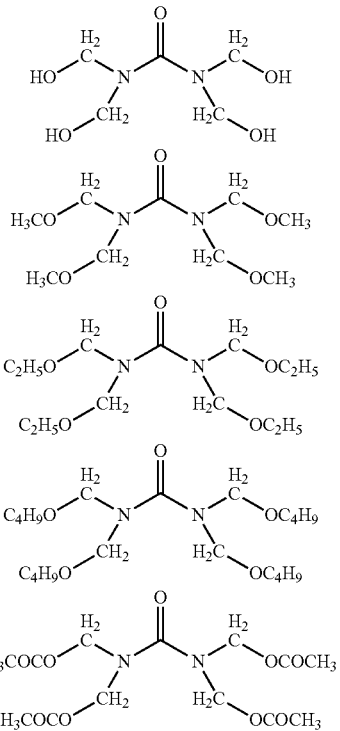

The alkoxymethylated melamine compound is not particularly limited, and specific examples include N,N,N,N,N,N-hexa(methoxymethyl)melamine, N,N,N,N,N,N-hexa(ethoxymethyl)melamine, N,N,N,N,N,N-hexa(n-propoxymethyl)melamine, N,N,N,N,N,N-hexa(isopropoxymethyl)melamine, N,N,N,N,N,N-hexa(n-butoxymethyl)melamine, and N,N,N,N,N,N-hexa(t-butoxymethyl)melamine. Among these, N,N,N,N,N,N-hexa(methoxymethyl)melamine is particularly preferable.

The above acid crosslinking agent (G1) can be obtained by, for example, conducting a condensation reaction of a urea compound or a glycoluryl compound with formalin to introduce an methylol group, etherifying the product with lower alcohols such as methyl alcohol, ethyl alcohol, propyl alcohol, and butyl alcohol, and then cooling the reaction solution to collect a precipitated compound or resin thereof. The above acid crosslinking agent (G1) can be obtained as a commercially available product such as CYMEL (trade name, manufactured by MT AquaPolymer) and NIKALAC (manufactured by Sanwa Chemical).

Other particularly preferable examples of the acid crosslinking agent (G) include a phenol derivative having 1 to 6 benzene rings within a molecule and two or more hydroxyalkyl groups and/or alkoxyalkyl groups within the entire molecule, the hydroxyalkyl groups and/or alkoxyalkyl groups being bonded to any of the above benzene rings (acid crosslinking agent (G2)). Preferable examples thereof include a phenol derivative having a molecular weight of 1500 or less, 1 to 6 benzene rings and a total of two or more hydroxyalkyl groups and/or alkoxyalkyl groups within a molecule, the hydroxyalkyl groups and/or alkoxyalkyl groups being bonded to any one of the above benzene rings, or a plurality of benzene rings.

The hydroxyalkyl group bonded to a benzene ring is not particularly limited to, and is the one of C1-6 such as a hydroxymethyl group, a 2-hydroxyethyl group, and a 2-hydroxy-1-propyl group is preferable. As the alkoxyalkyl group bonded to a benzene ring, the one of C2-6 is preferable. Specifically, a methoxymethyl group, an ethoxymethyl group, an n-propoxymethyl group, an isopropoxymethyl group, an n-butoxymethyl group, an isobutoxymethyl group, a sec-butoxymethyl group, a t-butoxymethyl group, a 2-methoxyethyl group, or a 2-methoxy-1-propyl group is preferable.

Among these phenol derivatives, particularly preferable ones are shown below:

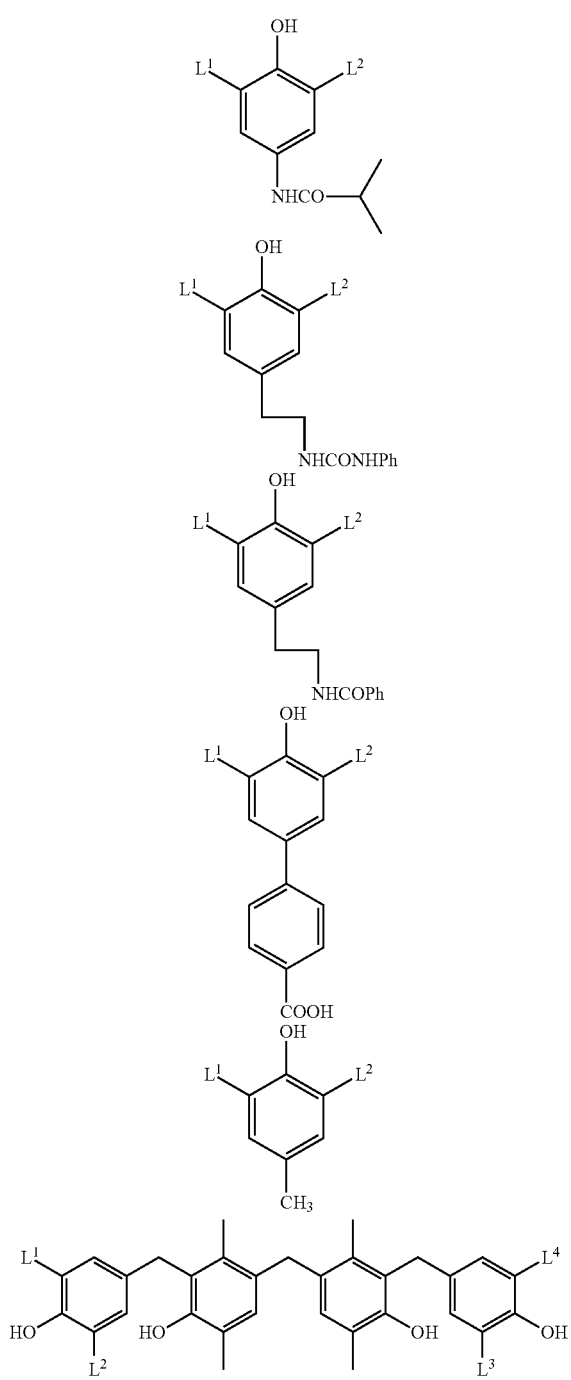

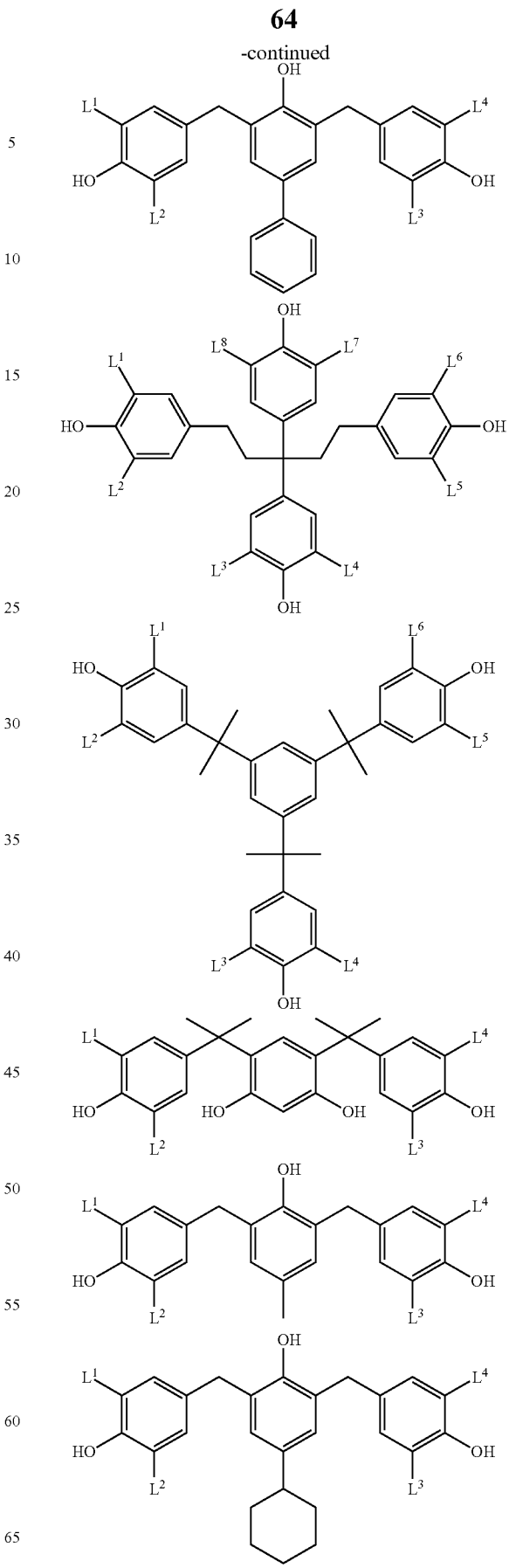

-continued
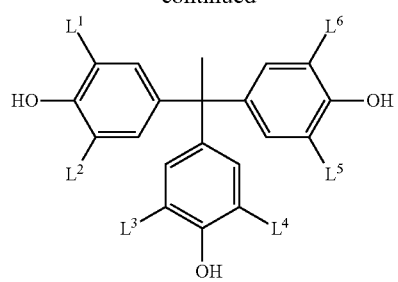
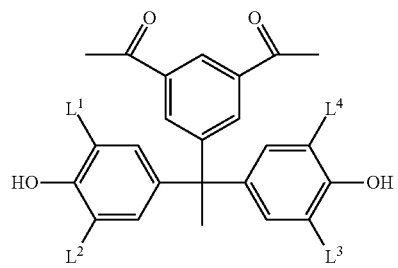
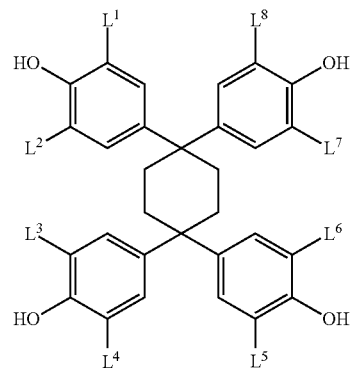
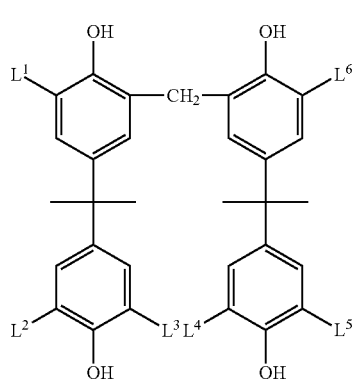
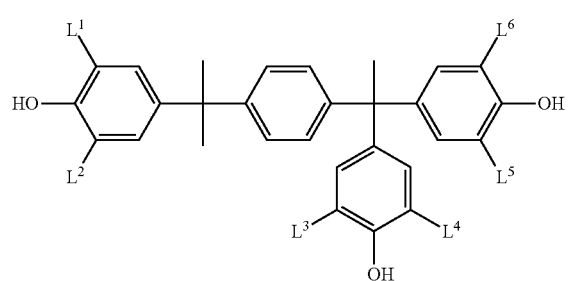
-continued
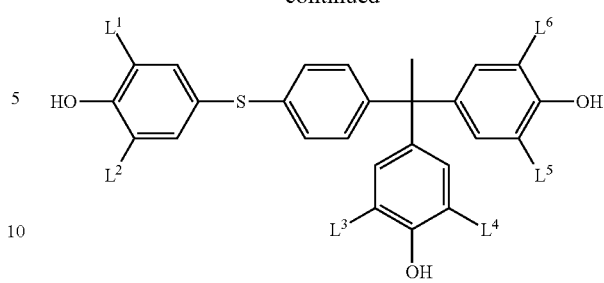
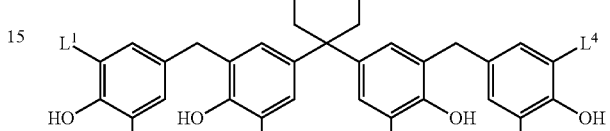
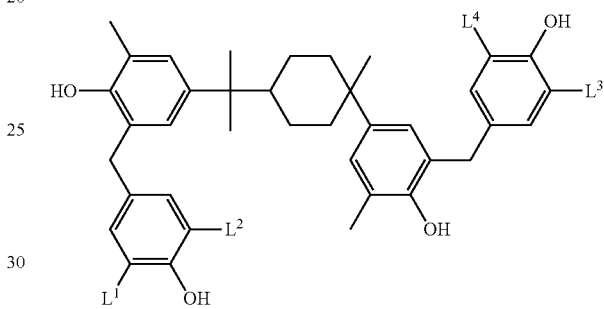
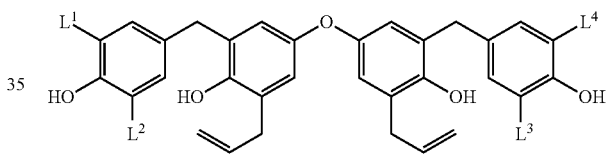
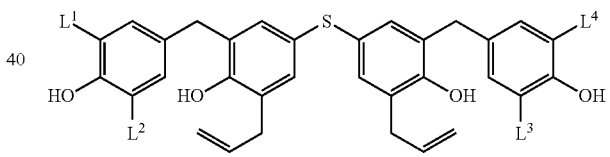
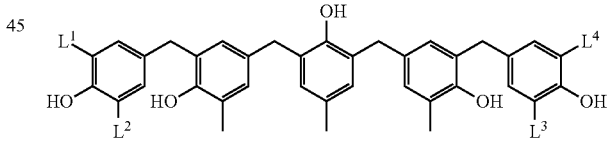
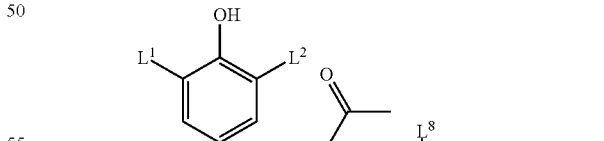
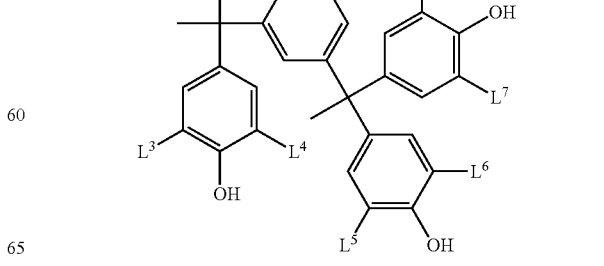

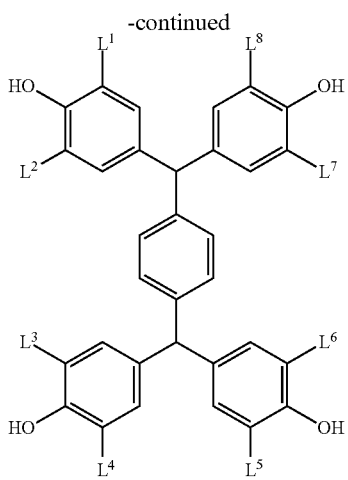

In the above formulae, $L^1$ to $L^8$ may be the same or different, and each independently represents a hydroxymethyl group, a methoxymethyl group, or an ethoxymethyl group. A phenol derivative having a hydroxymethyl group can be obtained by reacting the corresponding phenolic compound having no hydroxymethyl group (a compound where $L^1$ to $L^8$ in the above formulae are a hydrogen atom) with formaldehyde in the presence of a basic catalyst. In this case, in order to prevent resinification and gelation, the reaction temperature is preferably 60° C. or less. Specifically, it can be synthesized by methods described in Japanese Patent Application Laid-Open Nos. 6-282067 and 7-64285 or the like.

A phenol derivative having an alkoxymethyl group can be obtained by reacting the corresponding phenol derivative having a hydroxymethyl group with an alcohol in the presence of an acid catalyst. In this case, in order to prevent resinification and gelation, the reaction temperature is preferably 100° C. or less. Specifically, it can be synthesized by methods described in EP632003A1 or the like.

While the phenol derivative having a hydroxymethyl group and/or an alkoxymethyl group thus synthesized is preferable in terms of stability upon storage, the phenol derivative having an alkoxymethyl group is particularly preferable in terms of stability upon storage. The acid crosslinking agent (G2) may be used alone, or may be used in combination of two or more kinds.

Other particularly preferable examples of the acid crosslinking agent (G) include a compound having at least one α-hydroxyisopropyl group (acid crosslinking agent (G3)). The compound is not particularly limited in the structure, as long as it has an α-hydroxyisopropyl group. A hydrogen atom of a hydroxyl group in the above α-hydroxyisopropyl group may be substituted with one or more acid dissociation groups (R—COO— group, R—SO₂— group or the like, wherein R represents a substituent group selected from the group consisting of a C1-12 linear hydrocarbon group, a C3-12 cyclic hydrocarbon group, a C1-12 alkoxy group, a C3-12 1-branched alkyl group, and a C6-12 aromatic hydrocarbon group). Examples of a compound having the above α-hydroxyisopropyl group include one kind or two kinds or more of a substituted or non-substituted aromatic based compound, a diphenyl compound, a naphthalene compound, a furan compound or the like containing at least one α-hydroxyisopropyl group. Specific examples thereof include a compound represented by the following general formula (12-1) (hereinafter, referred to as "benzene based compound (1)"), a compound represented by the following general formula (12-2) (hereinafter, referred to as "diphenyl based compound (2)"), a compound represented by the following general formula (12-3) (hereinafter, referred to as "naphthalene based compound (3)"), and a compound represented by the following general formula (12-4) (hereinafter, referred to as "furan based compound (4)").

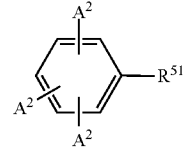
(12-1)

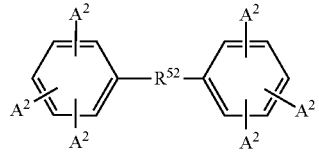
(12-2)

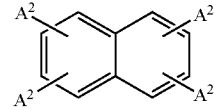
(12-3)

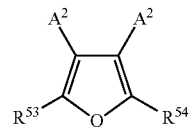
(12-4)

In the above general formulae (12-1) to (12-4), each $A^2$ independently represents an α-hydroxyisopropyl group or a hydrogen atom, and at least one $A^2$ is an α-hydroxyisopropyl group. In the general formula (12-1), $R^{51}$ represents a hydrogen atom, a hydroxyl group, a C2-6 linear or branched alkylcarbonyl group, or a C2-6 linear or branched alkoxycarbonyl group. Furthermore, in the general formula (10-2), $R^{52}$ represents a single bond, a C1-5 linear or branched alkylene group, —O—, —CO—, or —COO—. Also, in the general formula (12-4), $R^{53}$ and $R^{54}$ represent a hydrogen atom or a C1-6 linear or branched alkyl group independently from each other.

Specific examples of the above benzene based compound (1) are not particularly limited, and examples include α-hydroxyisopropylbenzenes such as α-hydroxyisopropylbenzene, 1,3-bis(α-hydroxyisopropyl)benzene, 1,4-bis(α-hydroxyisopropyl)benzene, 1,2,4-tris(α-hydroxyisopropyl)benzene, and 1,3,5-tris(α-hydroxyisopropyl)benzene; α-hydroxyisopropylphenols such as 3-α-hydroxyisopropylphenol, 4-α-hydroxyisopropylphenol, 3,5-bis(α-hydroxyisopropyl)phenol, and 2,4,6-tris(α-hydroxyisopropyl)phenol; α-hydroxyisopropylphenyl alkyl ketones such as 3-α-hydroxyisopropylphenyl methyl ketone, 4-α-hydroxyisopropylphenyl methyl ketone, 4-α-hydroxyisopropylphenyl ethyl ketone, 4-α-hydroxyisopropylphenyl-n-propyl ketone, 4-α-hydroxyisopropylphenyl isopropyl ketone, 4-α-hydroxyisopropylphenyl-n-butyl ketone, 4-α-hydroxyisopropylphenyl-t-butyl ketone, 4-α-hydroxyisopropylphenyl-n-pentyl ketone, 3,5-bis(α-hydroxyisopropyl)phenyl methyl ketone, 3,5-bis(α-hydroxyisopropyl)phenyl ethyl ketone, and 2,4,6-tris(α-hydroxyisopropyl)phenyl methyl ketone; alkyl 4-α- hydroxyisopropylbenzoates such as methyl 3-α-hydroxyisopropylbenzoate, methyl 4-α-hydroxyisopropylbenzoate, ethyl 4-α-hydroxyisopropylbenzoate, n-propyl 4-α-hydroxyisopropylbenzoate, isopropyl 4-α-hydroxyisopropylbenzoate, n-butyl 4-α-hydroxyisopropylbenzoate, t-butyl 4-α-hydroxyisopropylbenzoate, n-pentyl 4-α-hydroxyisopropylbenzoate, methyl 3,5-bis(α-hydroxyisopropyl)benzoate, ethyl 3,5-bis(α-hydroxyisopropyl)benzoate, and methyl 2,4,6-tris(α-hydroxyisopropyl)benzoate.

Specific examples of the above diphenyl based compound (2) are not particularly limited, and examples include α-hydroxyisopropylbiphenyls such as 3-α-hydroxyisopropylbiphenyl, 4-α-hydroxyisopropylbiphenyl, 3,5-bis(α-hydroxyisopropyl)biphenyl, 3,3'-bis(α-hydroxyisopropyl)biphenyl, 3,4'-bis(α-hydroxyisopropyl)biphenyl, 4,4'-bis(α-hydroxyisopropyl)biphenyl, 2,4,6-tris(α-hydroxyisopropyl)biphenyl, 3,3',5-tris(α-hydroxyisopropyl)biphenyl, 3,4',5-tris(α-hydroxyisopropyl)biphenyl, 2,3',4,6-tetrakis(α-hydroxyisopropyl)biphenyl, 2,4,4',6-tetrakis(α-hydroxyisopropyl)biphenyl, 3,3',5,5'-tetrakis(α-hydroxyisopropyl)biphenyl, 2,3',4,5',6-pentakis(α-hydroxyisopropyl)biphenyl, and 2,2',4,4',6,6'-hexakis(α-hydroxyisopropyl)biphenyl;

α-hydroxyisopropyldiphenylalkanes such as 3-α-hydroxyisopropyldiphenylmethane, 4-α-hydroxyisopropyldiphenylmethane, 1-(4-α-hydroxyisopropylphenyl)-2-phenylethane, 1-(4-α-hydroxyisopropylphenyl)-2-phenylpropane, 2-(4-α-hydroxyisopropylphenyl)-2-phenylpropane, 1-(4-α-hydroxyisopropylphenyl)-3-phenylpropane, 1-(4-α-hydroxyisopropylphenyl)-4-phenylbutane, 1-(4-α-hydroxyisopropylphenyl)-5-phenylpentane, 3,5-bis(α-hydroxyisopropyldiphenylmethane, 3,3'-bis(α-hydroxyisopropyl)diphenylmethane, 3,4'-bis(α-hydroxyisopropyl)diphenylmethane, 4,4'-bis(α-hydroxyisopropyl)diphenylmethane, 1,2-bis(4-α-hydroxyisopropylphenyl)ethane, 1,2-bis(4-α-hydroxypropylphenyl)propane, 2,2-bis(4-α-hydroxypropylphenyl)propane, 1,3-bis(4-α-hydroxypropylphenyl)propane, 2,4,6-tris(α-hydroxyisopropyl)diphenylmethane, 3,3',5-tris(α-hydroxyisopropyl)diphenylmethane, 3,4',5-tris(α-hydroxyisopropyl)diphenylmethane, 2,3',4,6-tetrakis(α-hydroxyisopropyl)diphenylmethane, 2,4,4',6-tetrakis(α-hydroxyisopropyl)diphenylmethane, 3,3',5,5'-tetrakis(α-hydroxyisopropyl)diphenylmethane, 2,3',4,5',6-pentakis(α-hydroxyisopropyl)diphenylmethane, and 2,2',4,4',6,6'-hexakis(α-hydroxyisopropyl)diphenylmethane;

α-hydroxyisopropyldiphenyl ethers such as 3-α-hydroxyisopropyldiphenyl ether, 4-α-hydroxyisopropyldiphenyl ether, 3,5-bis(α-hydroxyisopropyl)diphenyl ether, 3,3'-bis(α-hydroxyisopropyl)diphenyl ether, 3,4'-bis(α-hydroxyisopropyl)diphenyl ether, 4,4'-bis(α-hydroxyisopropyl)diphenyl ether, 2,4,6-tris(α-hydroxyisopropyl)diphenyl ether, 3,3',5-tris(α-hydroxyisopropyl)diphenyl ether, 3,4',5-tris(α-hydroxyisopropyl)diphenyl ether, 2,3',4,6-tetrakis(α-hydroxyisopropyl)diphenyl ether, 2,4,4',6-tetrakis(α-hydroxyisopropyl)diphenyl ether, 3,3',5,5'-tetrakis(α-hydroxyisopropyl)diphenyl ether, 2,3',4,5',6-pentakis(α-hydroxyisopropyl)diphenyl ether, and 2,2',4,4',6,6'-hexakis(α-hydroxyisopropyl)diphenyl ether;

α-hydroxyisopropyldiphenyl ketones such as 3-α-hydroxyisopropyldiphenyl ketone, 4-α-hydroxyisopropyldiphenyl ketone, 3,5-bis(α-hydroxyisopropyl)diphenyl ketone, 3,3'-bis(α-hydroxyisopropyl)diphenyl ketone, 3,4'-bis(α-hydroxyisopropyl)diphenyl ketone, 4,4'-bis(α-hydroxyisopropyl)diphenyl ketone, 2,4,6-tris(α-hydroxyisopropyl)diphenyl ketone, 3,3',5-tris(α-hydroxyisopropyl)diphenyl ketone, 3,4',5-tris(α-hydroxyisopropyl)diphenyl ketone, 2,3',4,6-tetrakis(α-hydroxyisopropyl)diphenyl ketone, 2,4,4',6-tetrakis(α-hydroxyisopropyl)diphenyl ketone, 3,3',5,5'-tetrakis(α-hydroxyisopropyl)diphenyl ketone, 2,3',4,5',6-pentakis(α-hydroxyisopropyl)diphenyl ketone, and 2,2',4,4',6,6'-hexakis(α-hydroxyisopropyl)diphenyl ketone; phenyl α-hydroxyisopropylbenzoates such as phenyl 3-α-hydroxyisopropylbenzoate, phenyl 4-α-hydroxyisopropylbenzoate, 3-α-hydroxyisopropylphenyl benzoate, 4-α-hydroxyisopropylphenyl benzoate, phenyl 3,5-bis(α-hydroxyisopropyl)benzoate, 3-α-hydroxyisopropylphenyl 3-α-hydroxyisopropylbenzoate, 4-α-hydroxyisopropylphenyl 3-α-hydroxyisopropylbenzoate, 3-α-hydroxyisopropylphenyl 4-α-hydroxyisopropylbenzoate, 4-α-hydroxyisopropylphenyl 4-α-hydroxyisopropylbenzoate, 3,5-bis(α-hydroxyisopropyl)phenyl benzoate, phenyl 2,4,6-tris(α-hydroxyisopropyl)benzoate, 3-α-hydroxyisopropylphenyl 3,5-bis(α-hydroxyisopropyl)benzoate, 4-α-hydroxyisopropylphenyl 3,5-bis(α-hydroxyisopropyl)benzoate, 3,5-bis(α-hydroxyisopropyl)phenyl 3-α-hydroxyisopropylbenzoate, 3,5-bis(α-hydroxyisopropyl)phenyl 4-α-hydroxyisopropylbenzoate, 2,4,6-tris(α-hydroxyisopropyl)phenyl benzoate, 3-α-hydroxyisopropylphenyl 2,4,6-tris(α-hydroxyisopropyl)benzoate, 4-α-hydroxyisopropylphenyl 2,4,6-tris(α-hydroxyisopropyl)benzoate, 3,5-bis(α-hydroxyisopropyl)phenyl 3,5-bis(α-hydroxyisopropyl)benzoate, 2,4,6-tris(α-hydroxyisopropyl)phenyl 3-α-hydroxyisopropylbenzoate, 2,4,6-tris(α-hydroxyisopropyl)phenyl 4-α-hydroxyisopropylbenzoate, 3,5-bis(α-hydroxyisopropyl)phenyl 2,4,6-tris(α-hydroxyisopropyl)benzoate, 2,4,6-tris(α-hydroxyisopropyl)phenyl 3,5-bis(α-hydroxyisopropyl)benzoate, and 2,4,6-tris(α-hydroxyisopropyl)phenyl 2,4,6-tris(α-hydroxyisopropyl)benzoate.

Furthermore, specific examples of the above naphthalene based compound (3) are not particularly limited, and examples include 1-(α-hydroxyisopropyl)naphthalene, 2-(α-hydroxyisopropyl)naphthalene, 1,3-bis(α-hydroxyisopropyl)naphthalene, 1,4-bis(α-hydroxyisopropyl)naphthalene, 1,5-bis(α-hydroxyisopropyl)naphthalene, 1,6-bis(α-hydroxyisopropyl)naphthalene, 1,7-bis(α-hydroxyisopropyl)naphthalene, 2,6-bis(α-hydroxyisopropyl)naphthalene, 2,7-bis(α-hydroxyisopropyl)naphthalene, 1,3,5-tris(α-hydroxyisopropyl)naphthalene, 1,3,6-tris(α-hydroxyisopropyl)naphthalene, 1,3,7-tris(α-hydroxyisopropyl)naphthalene, 1,4,6-tris(α-hydroxyisopropyl)naphthalene, 1,4,7-tris(α-hydroxyisopropyl)naphthalene, and 1,3,5,7-tetrakis(α-hydroxyisopropyl)naphthalene.

Specific examples of the above furan based compound (4) include, but not limited to, 3-(α-hydroxyisopropyl)furan, 2-methyl-3-(α-hydroxyisopropyl)furan, 2-methyl-4-(α-hydroxyisopropyl)furan, 2-ethyl-4-(α-hydroxyisopropyl)furan, 2-n-propyl-4-(α-hydroxyisopropyl)furan, 2-isopropyl-4-(α-hydroxyisopropyl)furan, 2-n-butyl-4-(α-hydroxyisopropyl)furan, 2-t-butyl-4-(α-hydroxyisopropyl)furan, 2-n-pentyl-4-(α-hydroxyisopropyl)furan, 2,5-dimethyl-3-(α-hydroxyisopropyl)furan, 2,5-diethyl-3-(α-hydroxyisopropyl)furan, 3,4-bis(α-hydroxyisopropyl)furan, 2,5-dimethyl-3,4-bis(α-hydroxyisopropyl)furan, and 2,5-diethyl-3,4-bis(α-hydroxyisopropyl)furan.

As the above acid crosslinking agent (G3), a compound having two or more free α-hydroxyisopropyl groups is preferable; the above benzene based compound (1) having two or more α-hydroxyisopropyl groups, the above diphenyl based compound (2) having two or more α-hydroxyisopropyl groups, and the above naphthalene based compound (3) having two or more α-hydroxyisopropyl groups are further preferable; and α-hydroxyisopropylbiphenyls having two or more α-hydroxyisopropyl groups and the above naphthalene based compound (3) having two or more α-hydroxyisopropyl groups are particularly preferable.

The above acid crosslinking agent (G3) can normally be obtained by a method for reacting an acetyl group-containing compound such as 1,3-diacetylbenzene with Grignard reagent such as CH₃MgBr to methylate and then hydrolyzing, or a method for oxidizing an isopropyl group-containing compound such as 1,3-diisopropylbenzene with oxygen or the like to produce a peroxide and then reducing.

In the resist composition of the present embodiment, the content of the acid crosslinking agent (G) is preferably 0.5 to 49% by mass of the total mass of the solid components, more preferably 0.5 to 40% by mass, still more preferably 1 to 30% by mass, and particularly preferably 2 to 20% by mass. When the content ratio of the above acid crosslinking agent (G) is 0.5% by mass or more, the inhibiting effect of the solubility of a resist film in an alkaline developing solution is improved, and a decrease in the film remaining rate, and occurrence of swelling and meandering of a pattern can be inhibited, which is preferable. On the other hand, when the content is 49% by mass or less, a decrease in heat resistance as a resist can be inhibited, which is preferable.

The content of at least one kind of compound selected from the above acid crosslinking agent (G1), acid crosslinking agent (G2), and acid crosslinking agent (G3) in the above acid crosslinking agent (G) is also not particularly limited, and can be within various ranges according to the kind of substrates or the like used upon forming a resist pattern.

In all acid crosslinking agent components, the content of the alkoxymethylated melamine compound and/or the compounds represented by formula (12-1) to formula (12-3) is not particularly limited, but is preferably 50 to 99% by mass, more preferably 60 to 99% by mass, still more preferably 70 to 98% by mass, and particularly preferably 80 to 97% by mass. By having the alkoxymethylated melamine compound and/or the compounds represented by formula (12-1) to formula (12-3) of 50% by mass or more of all acid crosslinking agent components, the resolution can be further improved, which is preferable. By having the compounds of 99% by mass or less, the pattern cross section is likely to have a rectangular shape, which is preferable.

The resist composition of the present embodiment may contain an acid diffusion controlling agent (E) having a function of controlling diffusion of an acid generated from an acid generating agent by radiation irradiation in a resist film to inhibit any unpreferable chemical reaction in an unexposed region or the like. By using such an acid diffusion controlling agent (E), the storage stability of a resist composition is improved. Also, along with the further improvement of the resolution, the line width change of a resist pattern due to variation in the post exposure delay time before radiation irradiation and the post exposure delay time after radiation irradiation can be inhibited, and the composition has extremely excellent process stability.

Such an acid diffusion controlling agent (E) is not particularly limited, and examples include a radiation degradable basic compound such as a nitrogen atom-containing basic compound, a basic sulfonium compound, and a basic iodonium compound. The acid diffusion controlling agent (E) can be used alone or in combination of two or more kinds.

The above acid diffusion controlling agent is not particularly limited, and examples include a nitrogen-containing organic compound, and a basic compound degradable by exposure. The above nitrogen-containing organic compound is not particularly limited, and examples include a compound represented by the following formula (13):

(hereinafter, referred to as a "nitrogen-containing compound (I)"), a diamino compound having two nitrogen atoms within the same molecule (hereinafter, referred to as a "nitrogen-containing compound (II)"), a polyamino compound or polymer having three or more nitrogen atoms (hereinafter, referred to as a "nitrogen-containing compound (III)"), an amide group-containing compound, a urea compound, and a nitrogen-containing heterocyclic compound. The acid diffusion controlling agent (E) may be used alone as one kind or may be used in combination of two or more kinds.

In the above formula (13), $R^{61}$, $R^{62}$, and $R^{63}$ represent a hydrogen atom, a linear, branched or cyclic alkyl group, an aryl group, or an aralkyl group independently from each other. The above alkyl group, aryl group, or aralkyl group may be non-substituted or may be substituted with a hydroxyl group or the like. Herein, the above linear, branched or cyclic alkyl group is not particularly limited, and examples include the one of C1-15, and preferably C1-10. Specific examples thereof include a methyl group, an ethyl group, an n-propyl group, an isopropyl group, an n-butyl group, an isobutyl group, a sec-butyl group, a t-butyl group, an n-pentyl group, a neopentyl group, an n-hexyl group, a texyl group, an n-heptyl group, an n-octyl group, an n-ethylhexyl group, an n-nonyl group, and an n-decyl group. Examples of the above aryl group include the one of C6-12. Specific examples thereof include a phenyl group, a tolyl group, a xylyl group, a cumenyl group, and a 1-naphthyl group. Furthermore, the above aralkyl group is not particularly limited, and examples include the one of C7-19, and preferably C7-13. Specific examples thereof include a benzyl group, an α-methylbenzyl group, a phenethyl group, and a naphthylmethyl group.

The above nitrogen-containing compound (I) is not particularly limited, and specific examples include particularly mono(cyclo)alkylamines such as n-hexylamine, n-heptylamine, n-octylamine, n-nonylamine, n-decylamine, n-dodecylamine, and cyclohexylamine; di(cyclo)alkylamines such as di-n-butylamine, di-n-pentylamine, di-n-hexylamine, di-n-heptylamine, di-n-octylamine, di-n-nonylamine, di-n-decylamine, methyl-n-dodecylamine, di-n-dodecylmethyl, cyclohexylmethylamine, and dicyclohexylamine; tri(cyclo)alkylamines such as triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, dimethyl-n-dodecylamine, di-n-dodecylmethylamine, dicyclohexylmethylamine, and tricyclohexylamine; alkanolamines such as monoethanolamine, diethanolamine, and triethanolamine; and aromatic amines such as aniline, N-methylaniline, N,N-dimethylaniline, 2-methylaniline, 3-methylaniline, 4-methylaniline, 4-nitroaniline, diphenylamine, triphenylamine, and 1-naphthylamine.

The above nitrogen-containing compound (II) is not particularly limited, and specific examples include particularly ethylenediamine, N,N,N',N'-tetramethylethylenediamine, N,N,N',N'-tetrakis(2-hydroxypropyl)ethylenediamine, tetramethylenediamine, hexamethylenediamine, 4,4'-diaminodiphenylmethane, 4,4'-diaminodiphenyl ether, 4,4'-diaminobenzophenone, 4,4'-diaminodiphenylamine, 2,2-bis(4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis[1-(4-aminophenyl)-1-methylethyl]benzene, and 1,3-bis[1-(4-aminophenyl)-1-methylethyl]benzene.

The above nitrogen-containing compound (III) is not particularly limited, and specific examples include particularly polymers of polyethyleneimine, polyarylamine, and N-(2-dimethylaminoethyl)acrylamide.

The above amide group-containing compound is not particularly limited, and specific examples include particularly formamide, N-methylformamide, N,N-dimethylformamide, acetamide, N-methylacetamide, N,N-dimethylacetamide, propioneamide, benzamide, pyrrolidone, and N-methylpyrrolidone.

The above urea compound is not particularly limited, and specific examples include particularly urea, methylurea, 1,1-dimethylurea, 1,3-dimethylurea, 1,1,3,3-tetramethylurea, 1,3-diphenylurea, and tri-n-butylthiourea.

The above nitrogen-containing heterocyclic compound is not particularly limited, and specific examples include particularly imidazoles such as imidazole, benzimidazole, 4-methylimidazole, 4-methyl-2-phenylimidazole, and 2-phenylbenzimidazole; pyridines such as pyridine, 2-methylpyridine, 4-methylpyridine, 2-ethylpyridine, 4-ethylpyridine, 2-phenylpyridine, 4-phenylpyridine, 2-methyl-4-phenylpyridine, nicotine, nicotinic acid, amide nicotinate, quinoline, 8-oxyquinoline, and acridine; and pyrazine, pyrazole, pyridazine, quinozaline, purine, pyrrolidine, piperidine, morpholine, 4-methylmorpholine, piperazine, 1,4-dimethylpiperazine, and 1,4-diazabicyclo[2.2.2]octane.

The radiation degradable basic compound is not particularly limited, and examples can include a sulfonium compound represented by the general formula (14-1):

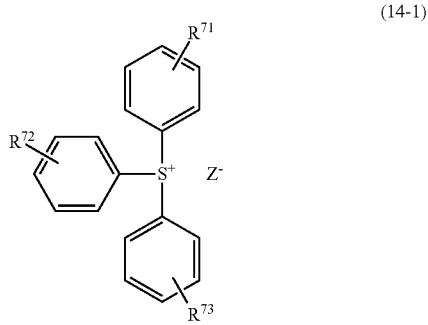

(14-1)

and an iodonium compound represented by the following formula (14-2):

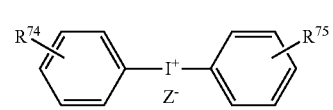

(14-2)

In the general formulae (14-1) and (14-2), $R^{71}$, $R^{72}$, $R^{73}$, $R^{74}$, and $R^{75}$ represent a hydrogen atom, a C1-6 alkyl group, a C1-6 alkoxyl group, a hydroxyl group, or a halogen atom independently from each other. $Z^-$ represents $HO^-$, $R\!-\!\!OO^-$ (R represents a C1-6 alkyl group, a C6-11 aryl group, or a C7-12 alkaryl group), or an anion represented by the following general formula (14-3):

(14-3)

Specific examples of the above radiation degradable basic compound are not particularly limited, and examples include triphenylsulfonium hydroxide, triphenylsulfonium acetate, triphenylsulfonium salicylate, diphenyl-4-hydroxyphenylsulfonium hydroxide, diphenyl-4-hydroxyphenylsulfonium acetate, diphenyl-4-hydroxyphenylsulfonium salicylate, bis(4-t-butylphenyl)iodonium hydroxide, bis(4-t-butylphenyl)iodonium acetate, bis(4-t-butylphenyl) iodonium salicylate, 4-t-butylphenyl-4-hydroxyphenyliodonium hydroxide, 4-t-butylphenyl-4-hydroxyphenyliodonium acetate, and 4-t-butylphenyl-4-hydroxyphenyliodonium salicylate.

The content of the acid diffusion controlling agent (E) is preferably 0.001 to 49% by mass of the total mass of the solid component, more preferably 0.01 to 10% by mass, still more preferably 0.01 to 5% by mass, and particularly preferably 0.01 to 3% by mass. When the content of the acid diffusion controlling agent (E) is within the above range, a decrease in resolution, and deterioration of the pattern shape and the dimension fidelity or the like can be further inhibited. Moreover, even though the post exposure delay time from electron beam irradiation to heating after radiation irradiation becomes longer, the shape of the pattern upper layer portion does not deteriorate. When the content of the acid diffusion controlling agent (E) is 10% by mass or less, a decrease in sensitivity, and developability of the unexposed portion or the like can be prevented. By using such an acid diffusion controlling agent, the storage stability of a resist composition improves, also along with improvement of the resolution, the line width change of a resist pattern due to variation in the post exposure delay time before radiation irradiation and the post exposure delay time after radiation irradiation can be inhibited, and the composition is extremely excellent process stability.

To the resist composition of the present embodiment, within the range of not inhibiting the purpose of the present embodiment, if required, as the other component (F), one kind or two kinds or more of various additive agents such as a dissolution promoting agent, a dissolution controlling agent, a sensitizing agent, a surfactant and an organic carboxylic acid or an oxo acid of phosphor, or derivative thereof can be added.

(Dissolution Promoting Agent)

A low molecular weight dissolution promoting agent is a component having a function of increasing the solubility of a compound represented by the above formula (1) in a developing solution to moderately increase the dissolution rate of the compound upon developing, when the solubility of the compound is too low. The low molecular weight dissolution promoting agent can be used, within the range of not deteriorating the effect of the present invention. The above dissolution promoting agent is not particularly limited, and examples can include low molecular weight phenolic compounds, such as bisphenols and tris(hydroxyphenyl)methane. These dissolution promoting agents can be used alone or in mixture of two or more kinds. The content of the dissolution promoting agent, which is arbitrarily adjusted according to the kind of the compound to be used, is preferably 0 to 49% by mass of the total mass of the solid component, more preferably 0 to 5% by mass, still more preferably 0 to 1% by mass, and particularly preferably 0% by mass.

(Dissolution Controlling Agent)

The dissolution controlling agent is a component having a function of controlling the solubility of the compound represented by the above formula (1) in a developing solution to moderately decrease the dissolution rate upon developing, when the solubility of the compound is too high. As such a dissolution controlling agent, the one which does not chemically change in steps such as calcination of resist coating, radiation irradiation, and development is preferable.

The dissolution controlling agent is not particularly limited, and examples include aromatic hydrocarbons such as phenanthrene, anthracene, and acenaphthene; ketones such as acetophenone, benzophenone, and phenyl naphtyl ketone; and sulfones such as methyl phenyl sulfone, diphenyl sulfone, and dinaphthyl sulfone. These dissolution controlling agents can be used alone or in two or more kinds.

The content of the dissolution controlling agent is not particularly limited and is arbitrarily adjusted according to the kind of the compound to be used, but is preferably 0 to 49% by mass of the total mass of the solid component, more preferably 0 to 5% by mass, still more preferably 0 to 1% by mass, and particularly preferably 0% by mass.

(Sensitizing Agent)

The sensitizing agent is a component having a function of absorbing irradiated radiation energy, transmitting the energy to the acid generating agent (C), and thereby increasing the acid production amount, and improving the apparent sensitivity of a resist. Such a sensitizing agent is not particularly limited, and examples include benzophenones, biacetyls, pyrenes, phenothiazines, and fluorenes. These sensitizing agents can be used alone or in two or more kinds. The content of the sensitizing agent, which is arbitrarily adjusted according to the kind of the compound to be used, is preferably 0 to 49% by mass of the total mass of the solid component, more preferably 0 to 5% by mass, still more preferably 0 to 1% by mass, and particularly preferably 0% by mass.

(Surfactant)

The surfactant is a component having a function of improving coatability and striation of the resist composition of the present embodiment, and developability of a resist or the like. Such a surfactant is not particularly limited, and may be any of anionic, cationic, nonionic or amphoteric. A preferable surfactant is a nonionic surfactant. The nonionic surfactant has a good affinity with a solvent used in production of resist compositions and more effects. Examples of the nonionic surfactant include, but not particularly limited to, a polyoxyethylene higher alkyl ethers, polyoxyethylene higher alkyl phenyl ethers, and higher fatty acid diesters of polyethylene glycol. Examples of commercially available products include, hereinafter by trade name, EFTOP (manufactured by Jemco Inc.), MEGAFAC (manufactured by DIC Corporation), Fluorad (manufactured by Sumitomo 3M Limited), AsahiGuard, Surflon (hereinbefore, manufactured by Asahi Glass Co., Ltd.), Pepole (manufactured by Toho Chemical Industry Co., Ltd.), KP (manufactured by Shin-Etsu Chemical Co., Ltd.), and Polyflow (manufactured by Kyoeisha Chemical Co., Ltd.). The content of the surfactant is not particularly limited, and is arbitrarily adjusted according to the kind of the compound to be used, is preferably 0 to 49% by mass of the total mass of the solid component, more preferably 0 to 5% by mass, further more preferably 0 to 1% by mass, and particularly preferably 0% by mass.

(Organic Carboxylic Acid or Oxo Acid of Phosphor or Derivative Thereof)

For the purpose of prevention of sensitivity deterioration or improvement of a resist pattern shape and post exposure delay stability or the like, and as an additional optional component, the resist composition of the present embodiment may contain an organic carboxylic acid or an oxo acid of phosphor or derivative thereof. The composition can be used in combination with the acid diffusion controlling agent, or may be used alone. The organic carboxylic acid is not particularly limited, and, for example, is suitably malonic acid, citric acid, malic acid, succinic acid, benzoic acid, salicylic acid, or the like. Examples of the oxo acid of phosphor or derivative thereof include phosphoric acid or derivative thereof such as ester including phosphoric acid, di-n-butyl ester phosphate, and diphenyl ester phosphate; phosphonic acid or derivative thereof such as ester including phosphonic acid, dimethyl ester phosphonate, di-n-butyl ester phosphonate, phenylphosphonic acid, diphenyl ester phosphonate, and dibenzyl ester phosphonate; and phosphinic acid and derivative thereof such as ester including phosphinic acid and phenylphosphinic acid. Among these, phosphonic acid is particularly preferable.

The organic carboxylic acid or the oxo acid of phosphor or derivative thereof can be used alone or in combination of two or more kinds. The content of the organic carboxylic acid or the oxo acid of phosphor or derivative thereof, which is arbitrarily adjusted according to the kind of the compound to be used, is preferably 0 to 49% by mass of the total mass of the solid component, more preferably 0 to 5% by mass, still more preferably 0 to 1% by mass, and particularly preferably 0% by mass.

(Other Additive Agent)

Furthermore, the resist composition of the present embodiment can contain one kind or two kinds or more of additive agents other than the above dissolution controlling agent, sensitizing agent, and surfactant, within the range of not inhibiting the purpose of the present invention, if required. Examples of such an additive agent include, but not particularly limited to, a dye, a pigment, and an adhesion aid. For example, the composition contains the dye or the pigment, and thereby a latent image of the exposed portion is visualized and influence of halation upon exposure can be alleviated, which is preferable. The composition contains the adhesion aid, and thereby adhesiveness to a substrate can be improved, which is preferable. Furthermore, examples of other additive agent can include, but not particularly limited to, a halation preventing agent, a storage stabilizing agent, a defoaming agent, and a shape improving agent. Specific examples thereof can include 4-hydroxy-4'-methylchalkone.

The total content of the optional component (F) is preferably 0 to 49% by mass of the total mass of the solid component, more preferably 0 to 5% by mass, still more preferably 0 to 1% by mass, and particularly preferably 0% by mass.

In the resist composition of the present embodiment, the content of the compound represented by the above formula (1) and/or the resin having the structure represented by the above formula (Z), the acid generating agent (C), the acid crosslinking agent (G), the acid diffusion controlling agent (E), the optional component (F) (the compound represented by the above formula (1) and/or the resin having the structure represented by the above formula (Z)/the acid generating agent (C)/the acid crosslinking agent (G)/the acid diffusion controlling agent (E)/the optional component (F)) is preferably 50 to 99.4/0.001 to 49/0.5 to 49/0.001 to 49/0 to 49 in % by mass based on the solid content, more preferably 55 to 90/1 to 40/0.5 to 40/0.01 to 10/0 to 5, still more preferably 60 to 80/3 to 30/1 to 30/0.01 to 5/0 to 1, and particularly preferably 60 to 70/10 to 25/2 to 20/0.01 to 3/0.

The content ratio of each component is selected from each range so that the summation thereof is 100% by mass. By the above content ratio, performance such as sensitivity, resolution, and developability is even better.

The method for purifying the resist composition of the present embodiment is not particularly limited, and, examples include a method involving dissolving each component in a solvent upon use into a homogenous solution, and then if required, filtering through a filter or the like with a pore diameter of about 0.2 μm, for example.

Examples of the solvent used in the preparation of the resist composition of the present embodiment can include, but not particularly limited to, ethylene glycol monoalkyl ether acetates such as ethylene glycol monomethyl ether acetate, ethylene glycol monoethyl ether acetate, ethylene glycol mono-n-propyl ether acetate, and ethylene glycol mono-n-butyl ether acetate; ethylene glycol monoalkyl ethers such as ethylene glycol monomethyl ether and ethylene glycol monoethyl ether; propylene glycol monoalkyl ether acetates such as propylene glycol monomethyl ether acetate, propylene glycol monoethyl ether acetate, propylene glycol mono-n-propyl ether acetate, and propylene glycol mono-n-butyl ether acetate; propylene glycol monoalkyl ethers such as propylene glycol monomethyl ether and propylene glycol monoethyl ether; ester lactates such as methyl lactate, ethyl lactate, n-propyl lactate, n-butyl lactate, and n-amyl lactate; aliphatic carboxylic acid esters such as methyl acetate, ethyl acetate, n-propyl acetate, n-butyl acetate, n-amyl acetate, n-hexyl acetate, methyl propionate, and ethyl propionate; other esters such as methyl 3-methoxypropionate, ethyl 3-methoxypropionate, methyl 3-ethoxypropionate, ethyl 3-ethoxypropionate, methyl 3-methoxy-2-methylpropionate, 3-methoxybutylacetate, 3-methyl-3-methoxybutylacetate, butyl 3-methoxy-3-methylpropionate, butyl 3-methoxy-3-methylbutyrate, methyl acetoacetate, methyl pyruvate, and ethyl pyruvate; aromatic hydrocarbon atoms such as toluene and xylene; ketones such as 2-heptanone, 3-heptanone, 4-heptanone, cyclopentanone, and cyclohexanone; amides such as N,N-dimethylformamide, N-methylacetamide, N,N-dimethylacetamide, and N-methylpyrrolidone; and lactones such as γ-lactone. These solvents can be used alone or in combination of two or more kinds.

The resist composition of the present embodiment can contain a resin within the range of not inhibiting the purpose of the present invention. Examples of the resin include, but not particularly limited to, a novolac resin, polyvinyl phenols, polyacrylic acid, polyvinyl alcohol, a styrene-maleic anhydride resin, an acrylic acid, vinyl alcohol or vinylphenol as a monomeric unit, or derivative thereof. The content of the resin is not particularly limited and is arbitrarily adjusted according to the kind of the compound represented by the above formula (1) and/or the resin having the structure represented by the above formula (Z) to be used, and is preferably 30 parts by mass or less per 100 parts by mass of the compound represented by the above formula (1) and/or the resin having the structure represented by the above formula (Z), more preferably 10 parts by mass or less, still more preferably 5 parts by mass or less, and particularly preferably 0 part by mass.

[Resist Pattern Formation Method]

A resist pattern formation method according to the present embodiment is not particularly limited, and a suitable method may be a method including steps of forming a resist film by coating a substrate with the above resist composition, exposing the formed resist film, and developing the exposed resist film to form a resist pattern.

The resist pattern of the present embodiment can also be formed as an upper layer resist in a multilayer process.

Specific examples of the resist pattern formation method include, but not particularly limited to, the following methods. A resist film is formed by coating a conventionally publically known substrate with the above resist composition using a coating means such as spin coating, flow casting coating, and roll coating. The conventionally publically known substrate is not particularly limited. For example, a substrate for electronic components, and the one having a predetermined wiring pattern formed thereon, or the like can be exemplified. More specific examples are not particularly limited, and examples include a substrate made of a metal such as a silicon wafer, copper, chromium, iron and aluminum, and a glass substrate. Examples of a wiring pattern material include, but not particularly limited to, copper, aluminum, nickel, and gold. Also if required, the substrate may be a substrate having an inorganic film and/or organic film provided thereon. Examples of the inorganic film include, but not particularly limited to, an inorganic antireflection film (inorganic BARC). Examples of the organic film include, but not particularly limited to, an organic antireflection film (organic BARC). Surface treatment with hexamethylene disilazane or the like may be conducted.

Next, the coated substrate is heated if required. The heating conditions vary according to the compounding composition of the resist composition, or the like, but are preferably 20 to 250° C., and more preferably 20 to 150° C. By heating, the adhesiveness of a resist to a substrate may improve, which is preferable. Then, the resist film is exposed to a desired pattern by any radiation selected from the group consisting of visible light, ultraviolet, excimer laser, electron beam, extreme ultraviolet (EUV), X-ray, and ion beam. The exposure conditions or the like are arbitrarily selected according to the compounding composition of the resist composition, or the like.

In the resist pattern formation method of the present embodiment, in order to stably form a fine pattern with a high degree of accuracy in exposure, the resist film is preferably heated after radiation irradiation. The heating conditions vary according to the compounding composition of the resist composition, or the like, but are preferably 20 to 250° C., and more preferably 20 to 150° C.

Next, by developing the exposed resist film in a developing solution, a predetermined resist pattern can be formed. As the developing solution, a solvent having a solubility parameter (SP value) close to that of the compound represented by the above formula (1) and/or the resin having the structure represented by the above formula (Z) to be used is preferably selected. A polar solvent such as a ketone-based solvent, an ester-based solvent, an alcohol-based solvent, an amide-based solvent, and an ether-based solvent; and a hydrocarbon-based solvent, or an alkaline aqueous solution can be used.

The ketone-based solvent is not particularly limited, and examples include 1-octanone, 2-octanone, 1-nonanone, 2-nonanone, acetone, 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonyl alcohol, acetyl carbinol, acetophenone, methyl naphthyl ketone, isophorone, and propylene carbonate.

The ester-based solvent is not particularly limited, and examples include methyl acetate, butyl acetate, ethyl acetate, isopropyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate, and propyl lactate.

The alcohol-based solvent is not particularly limited, and examples include an alcohol such as methyl alcohol, ethyl alcohol, n-propyl alcohol, isopropyl alcohol (2-propanol), n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; and a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol.

The ether-based solvent is not particularly limited, and examples include dioxane and tetrahydrofuran in addition to the glycol ether-based solvents.

The amide-based solvent is not particularly limited, and examples can be used include N-methyl-2-pyrrolidone, N,N-dimethylacetamide, N,N-dimethylformamide, phosphoric hexamethyltriamide, and 1,3-dimethyl-2-imidazolidinone.

The hydrocarbon-based solvent is not particularly limited, and examples include an aromatic hydrocarbon-based solvent such as toluene and xylene; and an aliphatic hydrocarbon-based solvent such as pentane, hexane, octane, and decane.

A plurality of above solvents may be mixed, or the solvent may be used by mixing the solvent with a solvent other than those described above or water within the range having performance. In order to sufficiently exhibit the effect of the present invention, the water content ratio as the whole developing solution is preferably less than 70% by mass and even less than 50% by mass, more preferably less than 30% by mass, and further preferably less than 10% by mass. Particularly preferably, the developing solution is substantially moisture free. That is, the content of the organic solvent in the developing solution is not particularly limited, and is preferably 30% by mass or more and 100% by mass or less based on the total amount of the developing solution, preferably even 50% by mass or more and 100% by mass or less, more preferably 70% by mass or more and 100% by mass or less, further more preferably 90% by mass or more and 100% by mass or less, and particularly preferably 95% by mass or more and 100% by mass or less.

The alkaline aqueous solution is not particularly limited, and examples include an alkaline compound such as mono-, di- or tri-alkylamines, mono-, di- or tri-alkanolamines, heterocyclic amines, tetramethyl ammonium hydroxide (TMAH), and choline.

Particularly, the developing solution containing at least one kind of solvent selected from a ketone-based solvent, an ester-based solvent, an alcohol-based solvent, an amide-based solvent, and an ether-based solvent improves resist performance such as resolution and roughness of the resist pattern, which is preferable.

The vapor pressure of the developing solution is preferably 5 kPa or less at 20° C., more preferably 3 kPa or less, and particularly preferably 2 kPa or less. The evaporation of the developing solution on the substrate or in a developing cup is inhibited by setting the vapor pressure of the developing solution to 5 kPa or less, to improve temperature uniformity within a wafer surface, thereby resulting in improvement in size uniformity within the wafer surface.

Specific examples having a vapor pressure of 5 kPa or less are not particularly limited, and examples include a ketone-based solvent such as 1-octanone, 2-octanone, 1-nonanone, 2-nonanone, 4-heptanone, 2-hexanone, diisobutyl ketone, cyclohexanone, methylcyclohexanone, phenylacetone, and methyl isobutyl ketone; an ester-based solvent such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxy propionate, 3-methoxy butyl acetate, 3-methyl-3-methoxy butyl acetate, butyl formate, propyl formate, ethyl lactate, butyl lactate, and propyl lactate; an alcohol-based solvent such as n-propyl alcohol, isopropyl alcohol, n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol; an ether-based solvent such as tetrahydrofuran; an amide-based solvent such as N-methyl-2-pyrrolidone, N,N-dimethylacetamide, and N,N-dimethylformamide; an aromatic hydrocarbon-based solvent such as toluene and xylene; and an aliphatic hydrocarbon-based solvent such as octane and decane.

Specific examples having a vapor pressure of 2 kPa or less which is a particularly preferable range include a ketone-based solvent such as 1-octanone, 2-octanone, 1-nonanone, 2-nonanone, 4-heptanone, 2-hexanone, diisobutyl ketone, cyclohexanone, methylcyclohexanone, and phenylacetone; an ester-based solvent such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxy propionate, 3-methoxy butyl acetate, 3-methyl-3-methoxy butyl acetate, ethyl lactate, butyl lactate, and propyl lactate; an alcohol-based solvent such as n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol; an amide-based solvent such as N-methyl-2-pyrrolidone, N,N-dimethylacetamide, and N,N-dimethylformamide; an aromatic hydrocarbon-based solvent such as xylene; and an aliphatic hydrocarbon-based solvent such as octane and decane.

To the developing solution, a surfactant can be added in an appropriate amount, if required. The surfactant is not particularly limited but, for example, an ionic or nonionic fluorine-based and/or silicon-based surfactant can be used. Examples of the fluorine-based and/or silicon-based surfactant include the surfactants described in Japanese Patent Application Laid-Open Nos. 62-36663, 61-226746, 61-226745, 62-170950, 63-34540, 7-230165, 8-62834, 9-54432, and 9-5988, and U.S. Pat. Nos. 5,405,720, 5,360, 692, 5,529,881, 5,296,330, 5,436,098, 5,576,143, 5,294,511, and 5,824,451. The surfactant is preferably a nonionic surfactant. The nonionic surfactant is not particularly limited, but a fluorine-based surfactant or a silicon-based surfactant is further preferably used.

The amount of the surfactant used is usually 0.001 to 5% by mass based on the total amount of the developing solution, preferably 0.005 to 2% by mass, and further preferably 0.01 to 0.5% by mass.

The development method is, for example, a method for dipping a substrate in a bath filled with a developing solution for a fixed time (dipping method), a method for raising a developing solution on a substrate surface by the effect of a surface tension and keeping it still for a fixed time, thereby conducting the development (puddle method), a method for spraying a developing solution on a substrate surface (spraying method), and a method for continuously ejecting a developing solution on a substrate rotating at a constant speed while scanning a developing solution ejecting nozzle at a constant rate (dynamic dispense method), or the like may be applied. The time for conducting the pattern development is not particularly limited, but is preferably 10 seconds to 90 seconds.

After the step of conducting development, a step of stopping the development by the replacement with another solvent may be practiced.

A step of rinsing the resist film with a rinsing solution containing an organic solvent is preferably provided after the development.

The rinsing solution used in the rinsing step after development is not particularly limited as long as the rinsing solution does not dissolve the resist pattern cured by crosslinking. A solution containing a general organic solvent or water may be used as the rinsing solution. As the rinsing solution, a rinsing solution containing at least one kind of organic solvent selected from a hydrocarbon-based solvent, a ketone-based solvent, an ester-based solvent, an alcohol-based solvent, an amide-based solvent, and an ether-based solvent is preferably used. More preferably, after development, a step of rinsing the film by using a rinsing solution containing at least one kind of organic solvent selected from the group consisting of a ketone-based solvent, an ester-based solvent, an alcohol-based solvent and an amide-based solvent is conducted. Still more preferably, after development, a step of rinsing the film by using a rinsing solution containing an alcohol-based solvent or an ester-based solvent is conducted. Further more preferably, after development, a step of rinsing the film by using a rinsing solution containing a monohydric alcohol is conducted. Particularly preferably, after development, a step of rinsing the film by using a rinsing solution containing a monohydric alcohol having 5 or more carbon atoms is conducted. The time for rinsing the pattern is not particularly limited, but is preferably 10 seconds to 90 seconds.

Herein, examples of the monohydric alcohol used in the rinsing step after development are not particularly limited, and specific examples include a linear, branched or cyclic monohydric alcohol. Specific examples include 1-butanol, 2-butanol, 3-methyl-1-butanol, tert-butyl alcohol, 1-pentanol, 2-pentanol, 1-hexanol, 4-methyl-2-pentanol, 1-heptanol, 1-octanol, 2-hexanol, cyclopentanol, 2-heptanol, 2-octanol, 3-hexanol, 3-heptanol, 3-octanol, and 4-octanol or the like can be used. Particularly preferable examples of monohydric alcohol having 5 or more carbon atoms include, but not limited to, 1-hexanol, 2-hexanol, 4-methyl-2-pentanol, 1-pentanol, and 3-methyl-1-butanol or the like can be used.

A plurality of these components may be mixed, or the component may be used by mixing the component with an organic solvent other than those described above.

The water content ratio in the rinsing solution is not particularly limited, and is preferably 10% by mass or less, more preferably 5% by mass or less, and particularly preferably 3% by mass or less. By setting the water content ratio to 10% by mass or less, better development characteristics can be obtained.

The vapor pressure at 20° C. of the rinsing solution used after development is preferably 0.05 kPa or more and 5 kPa or less, more preferably 0.1 kPa or more and 5 kPa or less, and much more preferably 0.12 kPa or more and 3 kPa or less. By setting the vapor pressure of the rinsing solution to 0.05 kPa or more and 5 kPa or less, the temperature uniformity in the wafer surface is enhanced and moreover, swelling due to permeation of the rinsing solution is further inhibited. As a result, the dimensional uniformity in the wafer surface is further improved.

The rinsing solution may also be used after adding an appropriate amount of a surfactant to the rinsing solution.

In the rinsing step, the wafer after development is rinsed using the organic solvent-containing rinsing solution. The method for rinsing treatment is not particularly limited. However, for example, a method for continuously ejecting a rinsing solution on a substrate spinning at a constant speed (spin coating method), a method for dipping a substrate in a bath filled with a rinsing solution for a fixed time (dipping method), and a method for spraying a rinsing solution on a substrate surface (spraying method), or the like can be applied. Above all, it is preferable to conduct the rinsing treatment by the spin coating method and after the rinsing, spin the substrate at a rotational speed of 2,000 rpm to 4,000 rpm, to remove the rinsing solution from the substrate surface.

After forming the resist pattern, a pattern wiring substrate is obtained by etching. Etching can be conducted by a publicly known method such as dry etching using plasma gas, and wet etching with an alkaline solution, a cupric chloride solution, and a ferric chloride solution or the like.

After forming the resist pattern, plating can also be conducted. Examples of the above plating method include, but not particularly limited to, copper plating, solder plating, nickel plating, and gold plating.

The remaining resist pattern after etching can be peeled by an organic solvent. Examples of the above organic solvent are not particularly limited, and examples include PGMEA (propylene glycol monomethyl ether acetate), PGME (propylene glycol monomethyl ether), and EL (ethyl lactate). Examples of the above peeling method are not particularly limited, and examples include a dipping method and a spraying method. A wiring substrate having a resist pattern formed thereon may be a multilayer wiring substrate, and may have a small diameter through hole.

In the present embodiment, the wiring substrate can also be formed by a method for forming a resist pattern, then depositing a metal in vacuum, and subsequently dissolving the resist pattern in a solution, i.e., a liftoff method.

[Polyphenol Compound]

The polyphenol compound represented by the above formula (1-4) can be produced by a publicly known method. The production method is not limited, and examples include a method including the step of reacting the compound represented by the following general formula (4) with an aldehyde of 1 to 19 carbon atoms in the presence of an acid catalyst, wherein at least one selected from the group consisting of $R^7$ in the following general formula (4) and the aldehyde contains an iodine atom. Such a production method is preferable because especially the amount of by-product is small, and the polyphenol compound represented by the above formula (1-4) can be efficiently produced.

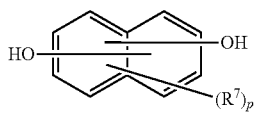

(4)

In the general formula (4), each $R^7$ is independently a halogen atom or an alkyl group of 1 to 4 carbon atoms, and p is an integer of 0 to 5.

The compound represented by the above general formula (4) is used without particular limitations as long as it is a compound having a dihydroxynaphthalene skeleton, and examples include 2,6-naphthalenediol, methyl-2,6-naphthalenediol, ethyl-2,6-naphthalenediol, propyl-2,6-naphthalenediol, butyl-2,6-naphthalenediol, fluoro-2,6-naphthalenediol, chloro-2,6-naphthalenediol, bromo-2,6-naphthalenediol, iodo-2,6-naphthalenediol, such compounds having diol at 1,5-positions, such compounds having diol at 1,6-positions, such compounds having diol at 1,7-positions, such compounds having diol at 2,3-positions, and such compounds having diol at 2,7-positions, and one kind or two or more kinds of these can be used. Having a naphthalene skeleton, the polyphenol compound represented by the above general formula (1-4) is expected to have better performance in terms of heat resistance than a polyphenol produced using a dihydroxy compound having a benzene ring skeleton. Also, having one hydroxy group per naphthalene ring, the polyphenol compound represented by the above general formula (1-4) exhibits the effect of having excellent solubility in safe solvents in addition to heat resistance.

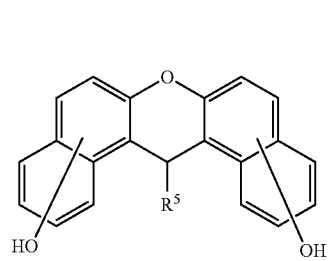

(2)

In the above formula (2), $R^5$ is a halogen atom, a linear, branched, or cyclic alkyl group of 1 to 10 carbon atoms, an aryl group of 6 to 10 carbon atoms, an alkenyl group of 2 to 10 carbon atoms, and an alkoxy group of 1 to 30 carbon atoms, provided that $R^5$ is a monovalent group containing an iodine atom.

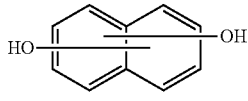

(5)

The compound of the present embodiment is preferably a benzoxanthene compound represented by the above formula (2) (Hereinafter sometimes referred to as a "xanthene compound"). Such a xanthene compound has excellent heat resistance.

In the present embodiment, the method for producing the xanthene compound represented by the above general formula (2) is not particularly limited and is the same as the synthesis method described for the above general formula (1), and examples include a method including the step of reacting the compound represented by the above formula (5) with an aldehyde of 1 to 19 carbon atoms in the presence of an acid catalyst, wherein the aldehyde contains an iodine atom.

In the present embodiment, $R^5$ is a monovalent group containing an iodine atom in the above formula (2).

In particular, because $R^5$ in the above formula (2) is a monovalent group containing an iodine atom, the xanthene compound of the present embodiment, in cooperation with other structural features of the above formula (2), increases the absorbability of radiation such as electron beam, extreme ultraviolet (EUV), and X-ray. As a result, it can be expected that the sensitivity and the resolution of a resist in which the xanthene compound of the present embodiment is used are increased. In extreme ultraviolet (EUV) lithography in particular, a high-sensitivity resist is considered essential for improving semiconductor device productivity, and the xanthene compound of the present embodiment is thus extremely useful.

Because $R^5$ is a monovalent group containing an iodine atom in the above formula (2), it is expected that from the xanthene compound of the present embodiment, a good resist pattern shape can be formed with which the sensitivity and the resolution of a resist is high and moreover the roughness of which is small.

Also, because $R^5$ in the above formula (2) is a monovalent group containing an iodine atom, in cooperation with other structural features of the above formula (2), the xanthene compound of the present embodiment provides even the effect of improving solubility in safe solvents.

The monovalent group containing an iodine atom is not particularly limited, and examples include an iodine atom, a linear aliphatic hydrocarbon group of 1 to 6 carbon atoms substituted with at least one iodine atom, a branched aliphatic hydrocarbon group of 3 to 6 carbon atoms substituted with at least one iodine atom, a cyclic aliphatic hydrocarbon group of 3 to 6 carbon atoms substituted with at least one iodine atom, and an aryl group of 6 carbon atoms substituted with at least one iodine atom.

The positions of hydroxy groups in naphthalenediol used in the present embodiment are not particularly limited as indicated in the above general formula (5), but are preferably 1,5-positions, 1,6-positions, 1,7-positions, 2,3-positions, 2,7-positions, and 2,6-positions from the viewpoint of the industrial applicability of raw materials, and more preferably 2,6-positions in terms of even higher solubility in safe solvents and low crystallinity.

For example, when producing a xanthene compound as represented by the following general formula (7), the use of naphthalenediol having hydroxy groups at 2,6-positions, i.e., a compound represented by the following general formula (6), enables a highly selective reaction and makes it possible to obtain the target compound in a high yield.

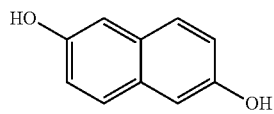
(6)

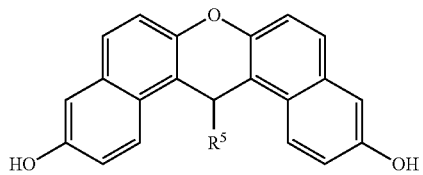
(7)

In the above formula (2), $R^5$ is a halogen atom, a linear, branched, or cyclic alkyl group of 1 to 10 carbon atoms, an aryl group of 6 to 10 carbon atoms, an alkenyl group of 2 to 10 carbon atoms, and an alkoxy group of 1 to 30 carbon atoms, provided that $R^5$ is a monovalent group containing an iodine atom.

Also, the use of naphthalenediol having hydroxy groups at 2,7-positions, i.e., a compound represented by the following general formula (8), makes it possible to obtain a xanthene compound as represented by the following general formula (9).

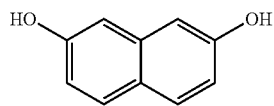
(8)

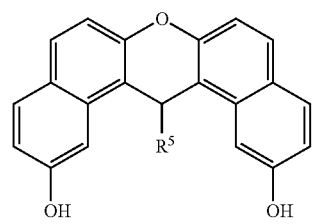
(9)

Examples of the method for producing the xanthene compound of the present embodiment include a method involving reacting naphthalenediol with benzaldehyde containing an iodine atom in the presence of a sulfuric acid catalyst to produce a compound represented by the following general formula (3).

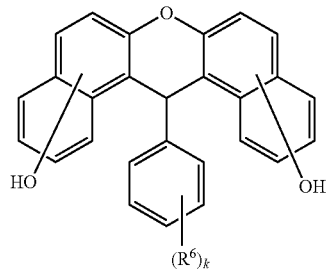
(3)

In the above formula (3), each $R^6$ is independently a hydrogen atom, a halogen atom, a linear, branched, or cyclic alkyl group of 1 to 10 carbon atoms, an aryl group of 6 to 10 carbon atoms, an alkenyl group of 2 to 10 carbon atoms, an alkoxy group of 1 to 30 carbon atoms, a thiol group, or a hydroxy group, and each k is independently an integer of 1 to 5, provided that at least one $R^6$ is a monovalent group containing an iodine atom.

EXAMPLES

The present embodiment will be more specifically described with reference to examples below. However, the present invention is not limited to these examples.

Below, methods for measuring a compound and methods for evaluating resist performance and the like in examples are presented.

[Measurement Method]
(1) Structure of Compound

The structure of the compound was verified by carrying out $^1$H-NMR measurement under the following conditions using an Advance 600 II spectrometer manufactured by Bruker.

Frequency: 400 MHz
Solvent: d6-DMSO
Internal standard: TMS
Measurement temperature: 23° C.

(2) Molecular Weight of Compound

The molecular weight of the compound was measured by FD-MS analysis using JMS-T100GCV manufactured by JEOL. Alternatively, the weight average molecular weight (Mw) and the number average molecular weight (Mn) in terms of polystyrene were determined by gel permeation chromatography (GPC) analysis to determine dispersibility (Mw/Mn).

Apparatus: Shodex Model GPC-101 (manufactured by Showa Denko K.K.)
Columns: KF-80M×3
Eluant: THF 1 ml/min
Temperature: 40° C.

(3) Metal Content of Compound

The metal content of the compound was measured by ICP-MS analysis using ELAN DRC II manufactured by PerkinElmer.

[Evaluation Method]
(1) Safe Solvent Solubility Test of Compound

The solubilities of the compound in PGME, PGMEA, and CHN were evaluated according to the following criteria utilizing the amount of dissolution in each solvent. The amount of dissolution was measured at 23° C. by precisely weighing the compound into a test tube, adding a subject solvent so as to attain a predetermined concentration, applying ultrasonic waves for 30 minutes in an ultrasonic cleaner, and visually observing the subsequent state of the fluid.

A: 5.0% by mass≤Amount of dissolution
B: 2.0% by mass≤Amount of dissolution<5.0% by mass
C: Amount of dissolution<2.0% by mass (2) Storage Stability and Thin Film Formability of Resist Composition The storage stability of a resist composition containing the compound was evaluated by leaving the resist composition to stand still for three days at 23° C. after preparation and then visually observing the resist composition for the presence and absence of precipitates. A clean silicon wafer was spin coated with the resist composition, and then prebaked (PB) before exposure in an oven of 110° C. to form a resist film with a thickness of 40 nm. The prepared resist composition was evaluated as ○ when it was a homogeneous solution and the thin film formability was good, Δ when it was a homogeneous solution but the thin film had defects, and × when there were precipitates.

(3) Pattern Evaluation of Resist Pattern (Pattern Formation)

The resist film obtained in (2) above was irradiated with electron beams of 1:1 line and space setting with a 500 nm interval and a 50 nm interval using an electron beam lithography system (ELS-7500 manufactured by ELIONIX INC.).

After irradiation, the resist film was heated at each predetermined temperature for 90 seconds, and immersed in 2.38% by mass TMAH alkaline developing solution for 60 seconds for development. Subsequently, the resist film was washed with ultrapure water for 30 seconds, and dried to form a negative type resist pattern. Concerning the formed resist pattern, the line and space were observed by a scanning electron microscope (S-4800 manufactured by Hitachi High-Technologies Corporation) to evaluate the reactivity by electron beam irradiation of the resist composition.

Synthesis Example 1

Synthesis of A-1 (Xanthene Compound)

To a container (internal capacity: 300 ml) equipped with a stirrer, a condenser tube, and a burette, 7.0 g (40 mmol) of 2,6-naphthalenediol (a reagent manufactured by Sigma-Aldrich), 4.6 g (20 mmol) of 3-iodobenzaldehyde (a reagent manufactured by Tokyo Kasei Kogyo Co., Ltd.), and 100 ml of γ-butyrolactone were fed, 0.5 g of p-toluenesulfonic acid was added, and the mixture was reacted by being stirred at 90° C. for 23 hours to obtain a reaction solution. Next, 1000 g of pure water was added to the reaction solution, then extracted by ethyl acetate, and concentrated to obtain a solution.

The obtained solution was separated by column chromatography and then washed with chloroform to obtain 4.2 g of the objective compound (A-1) represented by the following formula (A-1). As a result of measuring the molecular weight of the obtained compound (A-1) by the above method, it was 516.

The following peaks were found by NMR measurement performed on the obtained compound (A-1) under the above measurement conditions, and the compound was confirmed to have a chemical structure of the following formula (A-1).

δ (ppm) 9.7 (2H, O—H), 7.0-8.5 (14H, Ph-H), 6.5 (1H, C—H)

That the substituted position of 2,6-naphthalenediol was 1-position in the obtained compound (A-1) was confirmed from the signals of the protons at 3-position and 4-position being doublet.

Moreover, the solubilities of the obtained compound (A-1) in safe solvents were evaluated by the above method. The results are shown in Table 1.

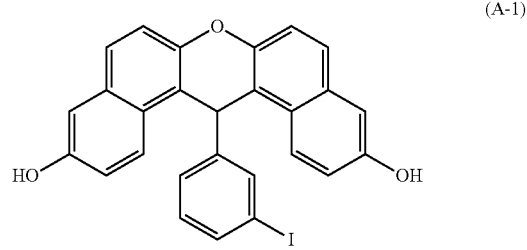 [SMILES: Oc1ccc2c3c(ccc2c1)Oc1ccc2cc(O)ccc2c1C3c1cccc(I)c1]

(A-1)

Synthesis Example 2

Synthesis of A-2 (Xanthene Compound)

To a container (internal capacity: 100 ml) equipped with a stirrer, a condenser tube, and a burette, 3.5 g (20 mmol) of 2,6-naphthalenediol (a reagent manufactured by Sigma-Aldrich), 2.3 g (20 mmol) of 4-iodobenzaldehyde (a reagent manufactured by Tokyo Kasei Kogyo Co., Ltd.), and 50 ml of γ-butyrolactone were fed, 0.3 g of p-toluenesulfonic acid was added, and the mixture was reacted by being stirred at 90° C. for 28 hours to obtain a reaction solution. Next, 500 g of pure water was added to the reaction solution, then extracted by ethyl acetate, and concentrated to obtain a solution.

The obtained solution was separated by column chromatography and then washed with chloroform to obtain 1.2 g of the objective compound (A-2) represented by the following formula (A-2). As a result of measuring the molecular weight of the obtained compound (A-2) by the above method, it was 516.

The following peaks were found by NMR measurement performed on the obtained compound (A-2) under the above measurement conditions, and the compound was confirmed to have a chemical structure of the following formula (A-2).

δ (ppm) 9.7 (2H, O—H), 7.2-8.5 (14H, Ph-H), 6.5 (1H, C—H)

That the substituted position of 2,6-naphthalenediol was 1-position in the obtained compound (A-2) was confirmed from the signals of the protons at 3-position and 4-position being doublet.

Moreover, the solubilities of the obtained compound (A-2) in safe solvents were evaluated by the above method. The results are shown in Table 1.

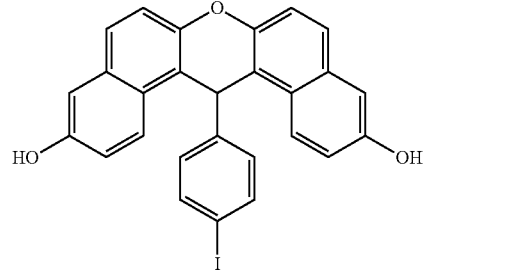

(A-2)

Synthesis Example 3

Synthesis of A-3 (Xanthene Compound)

To a container (internal capacity: 300 ml) equipped with a stirrer, a condenser tube, and a burette, 7.0 g (40 mmol) of 2,6-naphthalenediol (a reagent manufactured by Sigma-Aldrich), 5.6 g (20 mmol) of 5-iodovanillin (a reagent manufactured by Tokyo Kasei Kogyo Co., Ltd.), and 100 ml of γ-butyrolactone were fed, 0.5 g of p-toluenesulfonic acid was added, and the mixture was reacted by being stirred at 90° C. for 87 hours to obtain a reaction solution. Next, 1000 g of pure water was added to the reaction solution, then extracted by ethyl acetate, and concentrated to obtain a solution.

The obtained solution was separated by column chromatography and then washed with chloroform to obtain 2.0 g of the objective compound (A-3) represented by the following formula (A-3). As a result of measuring the molecular weight of the obtained compound (A-3) by the above method, it was 562.

The following peaks were found by NMR measurement performed on the obtained compound (A-3) under the above measurement conditions, and the compound was confirmed to have a chemical structure of the following formula (A-3).

δ (ppm) 9.7, 9.3 (3H, O—H), 7.2-8.5 (12H, Ph-H), 6.4 (1H, C—H), 3.7 (3H, O—C—H)

That the substituted position of 2,6-naphthalenediol was 1-position in the obtained compound (A-3) was confirmed from the signals of the protons at 3-position and 4-position being doublet.

Moreover, the solubilities of the obtained compound (A-3) in safe solvents were evaluated by the above method. The results are shown in Table 1.

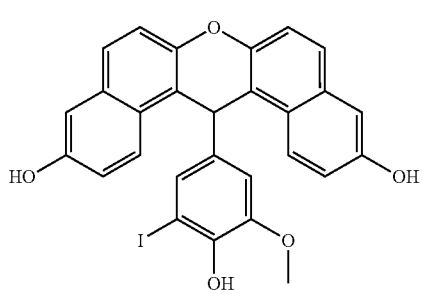

(A-3)

Synthesis Example 4

Synthesis of B-1 (Xanthene Compound)

4.0 g of the objective compound (B-1) represented by the following formula (B-1) was obtained in the same manner as in Synthesis Example 1 except that 7.0 g (40 mmol) of 2,6-naphthalenediol was replaced with 7.0 g (40 mmol) of 2,7-naphthalenediol (a reagent manufactured by Sigma-Aldrich), and the reaction time was changed from 23 hours to 10 hours. As a result of measuring the molecular weight of the obtained compound (B-1) by the above method, it was 516.

The following peaks were found by NMR measurement performed on the obtained compound (B-1) under the above measurement conditions, and the compound was confirmed to have a chemical structure of the following formula (B-1).

δ (ppm) 10.0 (2H, O—H), 7.0-7.8 (14H, Ph-H), 6.1 (1H, C—H)

Moreover, the solubilities of the obtained compound (B-1) in safe solvents were evaluated by the above method. The results are shown in Table 1.

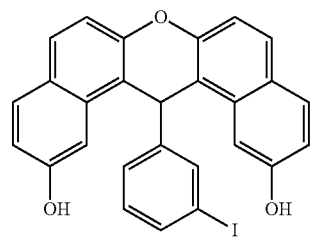

(B-1)

Synthesis Example 5

Synthesis of B-2 (Xanthene Compound)

1.8 g of the objective compound (B-2) represented by the following formula (B-2) was obtained in the same manner as in Synthesis Example 2 except that 3.5 g (20 mmol) of 2,6-naphthalenediol was replaced with 3.5 g (20 mmol) of 2,7-naphthalenediol (a reagent manufactured by Sigma-Aldrich), and the reaction time was changed from 28 hours to 8 hours.

As a result of measuring the molecular weight of the obtained compound (B-2) by the above method, it was 516.

The following peaks were found by NMR measurement performed on the obtained compound (B-2) under the above measurement conditions, and the compound was confirmed to have a chemical structure of the following formula (B-2).

δ (ppm) 9.9 (2H, O—H), 7.0-8.3 (14H, Ph-H), 6.1 (1H, C—H)

Moreover, the solubilities of the obtained compound (B-2) in safe solvents were evaluated by the above method. The results are shown in Table 1.

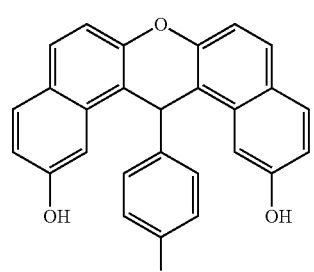

(B-2)

Synthesis Example 6

Synthesis of B-3 (Xanthene Compound)

2.0 g of the objective compound (B-3) represented by the following formula (B-3) was obtained in the same manner as in Synthesis Example 3 except that 7.0 g (40 mmol) of 2,6-naphthalenediol was replaced with 7.0 g (40 mmol) of 2,7-naphthalenediol (a reagent manufactured by Sigma-Aldrich), and the reaction time was changed from 87 hours to 10 hours. As a result of measuring the molecular weight of the obtained compound (B-3) by the above method, it was 562.

The following peaks were found by NMR measurement performed on the obtained compound (B-3) under the above measurement conditions, and the compound was confirmed to have a chemical structure of the following formula (B-3).

δ (ppm) 9.9, 9.4 (3H, O—H), 7.0-8.3 (12H, Ph-H), 6.0 (1H, C—H), 3.8 (3H, O—C—H)

Moreover, the solubilities of the obtained compound (B-3) in safe solvents were evaluated by the above method. The results are shown in Table 1.

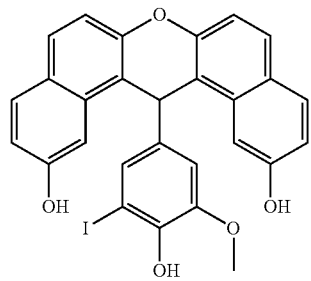

(B-3)

Synthesis Example 7

Synthesis of R1A-1

To a container (internal capacity: 100 ml) equipped with a stirrer, a condenser tube, and a burette, 10.8 g (21 mmol) of A-1, 0.7 g (42 mmol) of paraformaldehyde, 50 ml of glacial acetic acid, and 50 ml of PGME were fed, 8 ml of 95% sulfuric acid was added, and the reaction solution was stirred at 100° C. for 6 hours and reacted. Next, the reaction solution was concentrated. The reaction product was precipitated by the addition of 1000 ml of methanol. After cooling to room temperature, the precipitates were separated by filtration. The obtained solid matter was subjected to filtration, dried, and then separated and purified by column chromatography to obtain 7.2 g of the objective resin (R1A-1) having a structure represented by the following formula (R1A-1).

As a result of measuring the molecular weight in terms of polystyrene of the obtained resin (R1A-1) by the above method, it was Mn: 831, Mw: 1846, Mw/Mn: 2.30.

The following peaks were found by NMR measurement performed on the obtained resin (R1A-1) under the above measurement conditions, and the resin was confirmed to have a chemical structure of the following formula (R1A-1).

δ (ppm) 9.7 (2H, O—H), 7.0-8.5 (12H, Ph-H), 6.5 (1H, C—H), 4.1 (2H, —CH$_2$)

Moreover, the solubilities of the obtained resin (R1A-1) in safe solvents were evaluated by the above method. The results are shown in Table 1.

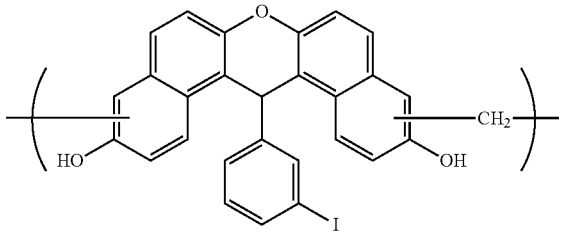

(R1A-1)

Synthesis Example 8

Synthesis of R2A-1

The same operations as in Synthesis Example 7 were performed except that 7.6 g (42 mmol) of 4-biphenylcarboxyaldehyde (manufactured by Mitsubishi Gas Chemical Company Inc.) was used in place of 0.7 g (42 mmol) of paraformaldehyde, to obtain 7.6 g of the objective resin (R2A-1) having a structure represented by the following formula (R2A-1).

As a result of measuring the molecular weight in terms of polystyrene of the obtained resin (R2A-1) by the above method, it was Mn: 614, Mw: 1208, Mw/Mn: 2.08.

The following peaks were found by NMR measurement performed on the obtained resin (R2A-1) under the above measurement conditions, and the resin was confirmed to have a chemical structure of the following formula (R2A-1).

δ (ppm) 9.7 (2H, O—H), 7.0-8.8 (21H, Ph-H), 6.6 (1H, C—H), 4.5 (1H, —CH)

Moreover, the solubilities of the obtained resin (R2A-1) in safe solvents were evaluated by the above method. The results are shown in Table 1.

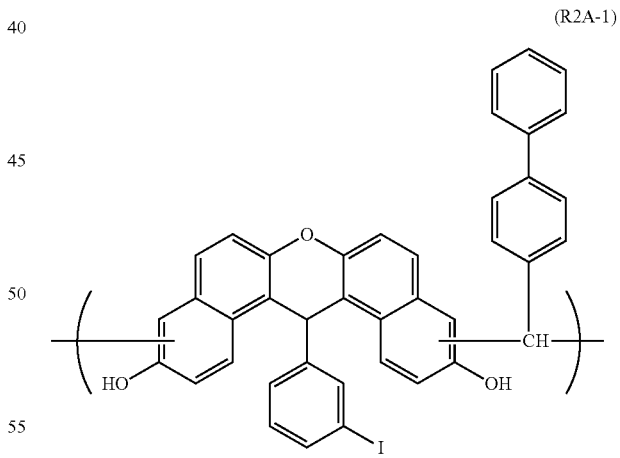

(R2A-1)

Production Example 1

Synthesis of BisN-1

To a container (internal capacity: 100 ml) equipped with a stirrer, a condenser tube, and a burette, 1.60 g (10 mmol) of 2,6-naphthalenediol (a reagent manufactured by Sigma-Aldrich), 1.82 g (10 mmol) of 4-biphenylaldehyde (manufactured by Mitsubishi Gas Chemical Company Inc.), and 30 ml of methyl isobutyl ketone were fed, 5 ml of 95% sulfuric acid was added, and the mixture was reacted by being stirred at 100° C. for 6 hours. Next, the reaction solution was concentrated. The reaction product was precipitated by the addition of 50 g of pure water. After cooling to room temperature, the precipitates were separated by filtration. The obtained solid matter was subjected to filtration, dried, and then separated and purified by column chromatography to obtain 3.05 g of the objective compound (BisN-1) represented by the following formula.

The following peaks were found by NMR measurement performed on the obtained compound (BisN-1) under the above measurement conditions, and the compound was confirmed to have a chemical structure of the following formula (BisN-1). That the substituted position of 2,6-naphthalenediol was 1-position was confirmed from the signals of protons at 3-position and 4-position being doublets.

δ (ppm) 9.7 (2H, O—H), 7.2-8.5 (19H, Ph-H), 6.6 (1H, C—H)

Moreover, the solubilities of the obtained compound (BisN-1) in safe solvents were evaluated by the above method. The results are shown in Table 1.

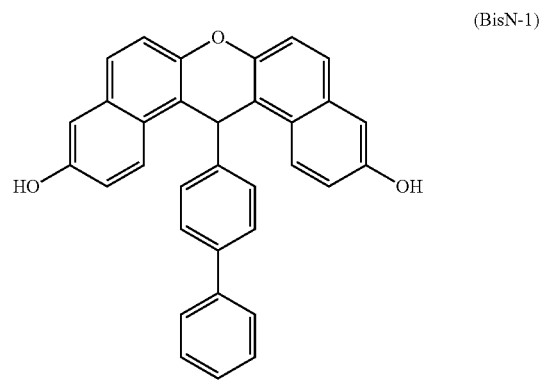 [SMILES: Oc1ccc2c3c(ccc2c1)Oc1ccc2cc(O)ccc2c1C3c1ccc(-c2ccccc2)cc1]

(BisN-1)

The solubilities in safe solvents of the compounds obtained in Synthesis Examples 1 to 8 and Production Example 1 were evaluated by the above method. The results are shown in Table 1.

TABLE 1

|  | Synthesis Example 1 | Synthesis Example 2 | Synthesis Example 3 | Synthesis Example 4 | Synthesis Example 5 | Synthesis Example 6 | Synthesis Example 7 | Synthesis Example 8 | Production Example 1 |
|---|---|---|---|---|---|---|---|---|---|
| PGME | A | A | A | A | A | A | A | A | A |
| PGMEA | A | A | A | A | C | A | A | A | A |
| CHN | A | A | A | B | A | A | A | A | A |

\* A: 5.0% by mass ≤ Amount of dissolution
B: 2.0% by mass ≤ Amount of dissolution <5.0% by mass
C: Amount of dissolution <2.0% by mass Examples 1-8 and Comparative Example 1

Concerning the compounds obtained in Synthesis Examples 1 to 8 and Production Example 1, the components set forth in Table 2 were prepared and formed into homogeneous solutions, and the obtained solutions were filtered through a Teflon (R) membrane filter with a pore diameter of 0.1 μm to prepare resist (radiation-sensitive) compositions. The obtained resist (radiation-sensitive) compositions each contained about 3 parts by mass of solid components and about 97 parts by mass of a solvent based on total 100 parts by mass of the solid components and the solvent, and had a content of the compound (any of the compounds obtained in Synthesis Examples 1 to 8 and Production Example 1) of 52.6% by mass, a content of the acid generator of 22.6% by mass, a content of the acid crosslinking agent of 22.6% by mass, and a content of the acid diffusion controlling agent of 2.2% by mass.

The storage stabilities and the thin film formabilities of the resist compositions of Examples 1 to 8 and Comparative Example 1 were evaluated by the above methods. The results are shown in Table 2.

TABLE 2

|  | Compound (g) | Acid generator (C) (g) | Acid crosslinking agent (G) (g) | Acid diffusion controlling agent (E) (g) | Solvent (g) | Storage stability and film formability |
|---|---|---|---|---|---|---|
| Example 1 | A-1 0.7 | P-1 0.3 | C-1 0.3 | Q-1 0.03 | S-1 40 | ○ |
| Example 2 | A-2 0.7 | P-1 0.3 | C-1 0.3 | Q-1 0.03 | S-1 40 | ○ |

TABLE 2-continued

| | Compound (g) | Acid generator (C) (g) | Acid crosslinking agent (G) (g) | Acid diffusion controlling agent (E) (g) | Solvent (g) | Storage stability and film formability |
|---|---|---|---|---|---|---|
| Example 3 | A-3 0.7 | P-1 0.3 | C-1 0.3 | Q-1 0.03 | S-1 40 | ○ |
| Example 4 | B-1 0.7 | P-1 0.3 | C-1 0.3 | Q-1 0.03 | S-1 40 | ○ |
| Example 5 | B-2 0.7 | P-1 0.3 | C-1 0.3 | Q-1 0.03 | S-1 40 | ○ |
| Example 6 | B-3 0.7 | P-1 0.3 | C-1 0.3 | Q-1 0.03 | S-1 40 | ○ |
| Example 7 | R1A-1 0.7 | P-1 0.3 | C-1 0.3 | Q-1 0.03 | S-1 40 | ○ |
| Example 8 | R2A-1 0.7 | P-1 0.3 | C-1 0.3 | Q-1 0.03 | S-1 40 | ○ |
| Comparative Example 1 | BisN-1 0.7 | P-1 0.3 | C-1 0.3 | Q-1 0.03 | S-1 40 | x |

"P-1", "C-1", "Q-1", and "S-1" in Table 2 are as follows.
Acid Generating Agent (C)
P-1: triphenylbenzenesulfonium trifluoromethanesulfonate (Midori Kagaku Co., Ltd.)
Acid Crosslinking Agent (G)
C-1: NIKALAC MW-100LM (Sanwa Chemical Co., Ltd.)
Acid Diffusion Controlling Agent (E)
Q-1: trioctylamine (Tokyo Kasei Kogyo Co., Ltd.) Solvent
S-1: propylene glycol monomethyl ether (Tokyo Kasei Kogyo Co., Ltd.)
S-4: Cyclohexanone (Tokyo Kasei Kogyo Co., Ltd.)

As can be understood from Table 2, all of the films formed from the resist compositions were confirmed to be good films having no defect and have good solubility and thin film formability (evaluation: o).

The resist compositions of Example 3, Example 6, and Example 7 showed reactivity due to irradiation with electron beams of 1:1 line and space setting with a 50 nm interval.

From the above results, it was found that the compounds (A-1, A-2, A-3, B-1, B-2, B-3, R1A-1, R2A-1) obtained in Synthesis Examples 1 to 8 meeting the requirements of the present invention have high solubility in safe solvents, and, also, resist compositions containing the compounds have good storage stability and thin film formability and can form a resist pattern. As long as the above requirements of the present invention are met, compounds other than those described in Examples also exhibit the same effects.

EXAMPLES

Production of PGMEA Solution of Compound Represented by Above General Formula (1) Having Reduced Metal Content Example 9

To a 4-neck flask (bottom-less type) having a volume of 1000 mL, 150 g of a solution (2.5% by mass) containing A-1 dissolved in PGMEA was fed, and heated to 80° C. while being stirred. Next, 37.5 g of an aqueous oxalic acid solution (pH 1.3) was added, and the mixture was stirred for 5 minutes and then left to stand still for 30 minutes. Accordingly, the mixture was separated into an oil phase and an aqueous phase, and the aqueous phase was removed. After this operation was repeated once, 37.5 g of ultrapure water was fed to the obtained oil phase, and the mixture was stirred for 5 minutes and then left to stand still for 30 minutes to remove the aqueous phase. By repeating this operation 3 times, a PGMEA solution of A-1 having a reduced metal content was obtained.

Example 10

A PGMEA solution of A-1 was obtained in the same manner as in Example 9 except that 135 g of PGMEA (120 g)/PGME (15 g) (10% by mass) was fed in place of 150 g of PGMEA (2.5% by mass).

Example 11

A PGMEA solution of A-1 was obtained in the same manner as in Example 10 except that 130 g of an aqueous citric acid solution (pH 1.8) was fed in place of 37.5 g of an aqueous oxalic acid solution (pH 1.3).

Reference Example 1

Production of Compound Having Reduced Metal Content with Ion Exchange Resin

After 25 g of an ion exchange resin (Mitsubishi Chemical Corporation Diaion: SMT100-mixed resin) was swollen by cyclohexanone, a Teflon (R) column was filled with the ion exchange resin, and 500 mL of 1,3-dioxolane was passed through for solvent displacement. Next, 500 g of a solution (1.7% by mass) containing A-1 dissolved in 1,3-dioxolane was passed through to obtain a dioxolane solution of A-1.

The contents of various metals in the 10% by mass PGMEA solution of A-1 that was before treatment and in the solutions of the compound represented by formula (1) or formula (2) obtained in Examples 9 to 11 and Reference Example 1 were measured by ICP-MS. The measurement results are shown in Table 3.

TABLE 3

| | Metal content (ppb) | | | | | |
|---|---|---|---|---|---|---|
| | Na | Mg | K | Fe | Cu | Zn |
| A-1 before treatment | 34 | 1.3 | 1.2 | >99 | 2.9 | 13.7 |
| Example 9 | ≤0.2 | ≤0.2 | ≤0.2 | ≤0.2 | ≤0.2 | ≤0.2 |
| Example 10 | ≤0.2 | ≤0.2 | ≤0.2 | ≤0.2 | ≤0.2 | ≤0.2 |

TABLE 3-continued

| | Metal content (ppb) | | | | | |
|---|---|---|---|---|---|---|
| | Na | Mg | K | Fe | Cu | Zn |
| Example 11 | ≤0.2 | ≤0.2 | ≤0.2 | ≤0.2 | ≤0.2 | ≤0.2 |
| Reference Example 1 | ≤0.2 | 0.5 | 1.1 | >99 | 1.2 | 0.6 |

The compound of the present invention has high solubility in safe solvents, and with the compound of the present invention, it is thus possible to provide a resist composition which has good storage stability and thin film formability and can impart a good shape to a resist pattern, and a method for forming a resist pattern using it. Accordingly, the compound of the present invention, the production method therefor, the composition containing the compound of the present invention, the method for forming a resist pattern using the composition are useful in the semiconductor field, the display field, photomasks, thin film magnetic heads, compound semiconductors, research and development, and the like where resist compositions such as acid-amplified non-polymeric resist materials are used.

Moreover, according to the present invention, a polyphenol compound having high solubility in safe solvents and good thin film formability can be provided. Accordingly, the present invention is suitably used for a base material of photosensitive materials such as photoresists for semiconductors, a raw material or a curing agent of an epoxy resin used for, for example, encapsulating materials of integrated circuits, a color developer or a discoloration inhibitor used for heat-sensitive recording materials, and, in addition, an additive for germicides and antimicrobial/antifungal agents, etc.

Moreover, the present invention can produce a compound represented by the above general formula (1) or a resin having a structure represented by the above general formula (Z) having a reduced metal content in an industrially advantageous manner.

The invention claimed is:

1. A compound represented by the following general formula (1):

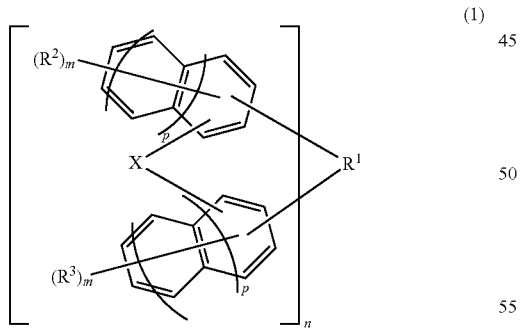

(1)

wherein each X is independently an oxygen atom, or a sulfur atom; $R^1$ is a 2n-valent group of 1 to 30 carbon atoms; $R^2$ and $R^3$ are each independently a halogen atom, a linear, branched, or cyclic alkyl group of 1 to 10 carbon atoms, an aryl group of 6 to 10 carbon atoms, an alkenyl group of 2 to 10 carbon atoms, an alkoxy group of 1 to 30 carbon atoms, a thiol group, or a hydroxy group; each m is independently an integer of 0 to 7, provided that at least one m is an integer of 1 to 7; each p is 1; and n is an integer of 1 to 4; provided that $R^1$ is a group comprising an iodine atom, and at least one $R^2$ and/or at least one $R^3$ is one or more selected from a hydroxy group and a thiol group.

2. The compound according to claim 1, wherein X is an oxygen atom in the above general formula (1).

3. The compound according to claim 1, wherein at least one $R^2$ is a hydroxy group, and at least one $R^3$ is a hydroxy group, in the above general formula (1).

4. The compound according to claim 1, wherein one $R^2$ is a hydroxy group, and one $R^3$ is a hydroxy group, in the above general formula (1).

5. The compound according to claim 1 wherein p is 1, and n is 1, in the above general formula (1).

6. The compound according to claim 1, wherein the compound represented by the above general formula (1) is a xanthene compound represented by the following general formula (2):

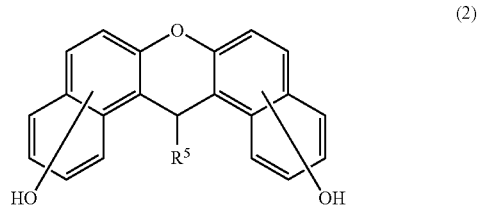

(2)

wherein $R^5$ is a halogen atom, a linear, branched, or cyclic alkyl group of 1 to 10 carbon atoms, an aryl group of 6 to 10 carbon atoms, an alkenyl group of 2 to 10 carbon atoms, and an alkoxy group of 1 to 30 carbon atoms, provided that $R^5$ is a monovalent group comprising an iodine atom.

7. The compound according to claim 1, wherein the compound represented by the above general formula (1) is a xanthene compound represented by the following general formula (3):

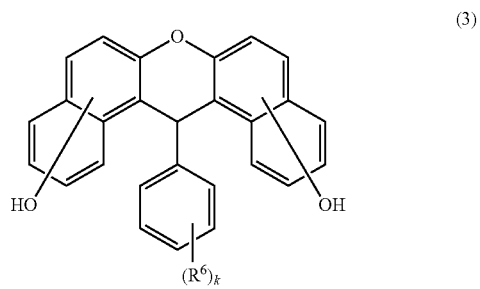

(3)

wherein each $R^6$ is independently a halogen atom, a linear, branched, or cyclic alkyl group of 1 to 10 carbon atoms, an aryl group of 6 to 10 carbon atoms, an alkenyl group of 2 to 10 carbon atoms, an alkoxy group of 1 to 30 carbon atoms, a thiol group, or a hydroxy group, and k is an integer of 1 to 5, provided that at least one $R^6$ is a monovalent group comprising an iodine atom.

8. The compound according to claim 1, wherein the compound represented by the above general formula (1) is a xanthene compound represented by the following formula (3-1):

(3-1)

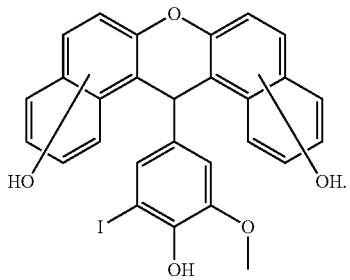

9. A resin obtained by reacting the compound according to claim 1 with a crosslinking compound.

10. The resin according to claim 9, wherein the crosslinking compound is an aldehyde, a ketone, a carboxylic acid, a carboxylic acid halide, a halogen-containing compound, an amino compound, an imino compound, an isocyanate, or an unsaturated hydrocarbon group-containing compound.

11. A resin having a structure represented by the following general formula (Z):

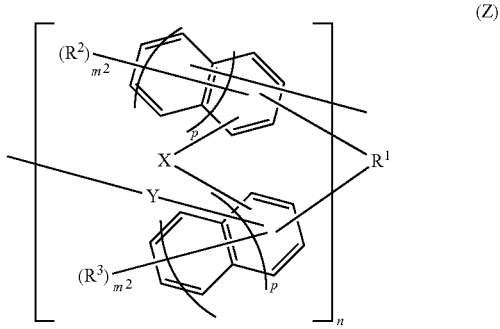

wherein each X is independently an oxygen atom, or a sulfur atom; $R^1$ is a 2n-valent group of 1 to 30 carbon atoms; $R^2$ and $R^3$ are each independently a halogen atom, a linear, branched, or cyclic alkyl group of 1 to 10 carbon atoms, an aryl group of 6 to 10 carbon atoms, an alkenyl group of 2 to 10 carbon atoms, an alkoxy group of 1 to 30 carbon atoms, a thiol group, or a hydroxy group; each Y is independently a single bond or a linear or branched alkylene group of 1 to 20 carbon atoms; each $m^2$ is independently an integer of 0 to 6, provided that at least one $m^2$ is an integer of 1 to 6; each p is 1; and n is an integer of 1 to 4; provided that $R^1$ is a group comprising an iodine atom, and at least one $R^2$ and/or at least one $R^3$ is one or more selected from a hydroxy group and a thiol group.

12. A resist composition comprising the compound according to claim 1, and further comprising a solvent, an acid generating agent, and an acid crosslinking agent.

13. A method for forming a resist pattern, comprising the steps of coating a substrate with the resist composition according to claim 12, thereby forming a resist film; exposing the formed resist film; and developing the exposed resist film.

14. A method for producing the compound according to claim 1, comprising the step of reacting a compound represented by the following general formula (4) with an aldehyde of 1 to 19 carbon atoms in the presence of an acid catalyst, wherein the aldehyde comprises an iodine atom:

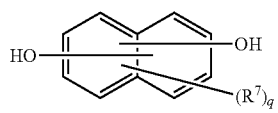

wherein each $R^7$ is independently a halogen atom or an alkyl group of 1 to 4 carbon atoms, and q is an integer of 0 to 5.

15. A method for producing the xanthene compound according to claim 6, comprising the step of reacting a compound represented by the following general formula (5) with an aldehyde of 1 to 19 carbon atoms in the presence of an acid catalyst, wherein the aldehyde comprises an iodine atom:

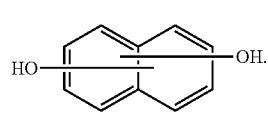

16. A purification method comprising the steps of:
obtaining a solution (A) by dissolving the compound according to claim 1 or the resin according to claim 9 in a solvent; and
extracting impurities in the compound or the resin by bringing the obtained solution (A) into contact with an acidic aqueous solution (a first extraction step), wherein
the solvent used in the step of obtaining the solution (A) comprises an organic solvent that does not inadvertently mix with water.

17. The purification method according to claim 16, wherein the acidic aqueous solution is an aqueous mineral acid solution or an aqueous organic acid solution;
the aqueous mineral acid solution is one or more aqueous mineral acid solutions selected from the group consisting of hydrochloric acid, sulfuric acid, nitric acid, and phosphoric acid; and
the aqueous organic acid solution is one or more aqueous organic acid solutions selected from the group consisting of acetic acid, propionic acid, oxalic acid, malonic acid, succinic acid, fumaric acid, maleic acid, tartaric acid, citric acid, methanesulfonic acid, phenolsulfonic acid, p-toluenesulfonic acid, and trifluoroacetic acid.

18. The purification method according to claim 16, wherein the organic solvent that does not inadvertently mix with water is one or more organic solvents selected from the group consisting of toluene, 2-heptanone, cyclohexanone, cyclopentanone, methyl isobutyl ketone, propylene glycol monomethyl ether acetate, and ethyl acetate.

19. The purification method according to claim 16, comprising the step of extracting impurities in the compound or the resin by further bringing a solution phase comprising the compound or the resin into contact with water after the first extraction step (a second extraction step).

20. A resist composition comprising a resin formed using the compound of claim 1, and further comprising a solvent, an acid generating agent, and an acid crosslinking agent.

21. A method for forming a resist pattern, comprising the steps of coating a substrate with the resist composition according to claim 20, thereby forming a resist film; exposing the formed resist film; and developing the exposed resist film.

\* \* \* \* \*